United States Patent
Ogura et al.

[11] Patent Number: 5,891,897
[45] Date of Patent: Apr. 6, 1999

[54] OXOPROPIONITRILE DERIVATIVE AND VERMIN CONTROLLING AGENT

[75] Inventors: Tomoyuki Ogura; Hiroshi Murakami; Rika Miyachi; Takeshi Nagaoka, all of Funabashi; Toshiro Miyake, Saitama-ken; Norihiko Mimori, Saitama-ken; Shinji Takii, Saitama-ken; Youichi Inoue, Saitama-ken, all of Japan

[73] Assignee: Nissan Chemical Industries, Ltd., Tokyo, Japan

[21] Appl. No.: 952,321

[22] PCT Filed: Apr. 26, 1996

[86] PCT No.: PCT/JP96/01164

§ 371 Date: Oct. 27, 1997

§ 102(e) Date: Oct. 27, 1997

[87] PCT Pub. No.: WO96/33995

PCT Pub. Date: Oct. 31, 1996

[30] Foreign Application Priority Data

Apr. 27, 1995  [JP]  Japan ..................... 7-104097
Apr. 17, 1996  [JP]  Japan ..................... 8-95096

[51] Int. Cl.[6] .................. C07D 417/06; A01N 43/78
[52] U.S. Cl. .................. 514/365; 514/342; 546/280; 548/200
[58] Field of Search .................. 514/342, 365; 548/200; 546/280

[56] References Cited

FOREIGN PATENT DOCUMENTS

| A-53-92769 | 8/1978 | Japan . |
|---|---|---|
| A-60-11401 | 1/1985 | Japan . |
| A-60-11452 | 1/1985 | Japan . |

OTHER PUBLICATIONS

Farm Chemicals Handbook, Pesticide Dictionary, 1994, pp. A4, A6, A8, C6, C10, C21, C31, C44, C51, C66, C78, C79, C81, C88, C98, C103–C105, C113, C119, C121, C124, C144, C157–C160, C162, C189, C192, C195, C196, C198 C204, C206, C209, C242, C244, C262, C265, C266, C272, C273, C276, C277, C283, C 295, C314, C318, C348, C356, C363 and C366.

Babichev Khim.–Fram. Zh. 23(6) pp. 695–696 Abstract Only, 1989.

Zaragoza Tet. Lett. 37(34) 6213–6, 1996.

*Primary Examiner*—Robert Gerstl
*Attorney, Agent, or Firm*—Oliff & Berridge, PLC

[57] ABSTRACT

Oxopropionitrile derivatives represented by general formula (1), and insect pest control agents containing the same as the active ingredient and having reduced toxicity and persistence. In said formula $R^1$ represents $C_2$–$C_8$ alkyl, etc., $R^2$ represents hydrogen, etc.; $R^3$ represents a heterocyclic group; and $R^4$ represents hydrogen, etc.

15 Claims, No Drawings

OXOPROPIONITRILE DERIVATIVE AND VERMIN CONTROLLING AGENT

This is a 371 of PCT/JP96/01164 filed Apr. 26, 1996.

TECHNICAL FIELD

The present invention relates to a novel oxopropionitrile derivative and a vermin controlling agent characterized by containing said derivative as an active ingredient.

1. Background Art

With respect to oxopropionitrile derivatives, for example, Japanese Unexamined Patent Publication No. Sho 53-92769 describes 2'-chloro-3-hydroxy-2-(4-phenyl-2-thiazolyl) cinnamonitrile. Additionally, Japanese Unexamined Patent Publication No. Sho 60-11452 describes 2-(4-chlorophenyl)-3-pyridinyl)-3-oxopropionitrile as an herbicide, and Japanese Unexamined Patent Publication No. Sho 60-11401 describes the compound as an bactericide.

Long-term use of insecticides has led vermin to acquire the resistance in recent years and the control by conventional insecticides difficult. Additionally, part of the insecticides have high toxicity, and some have disorganized the ecosystem by their persistence. Accordingly, novel insecticides of low toxicity and low persistence have always been desired.

2. Disclosure of the Invention

In view of such situations, the present inventors have been studied to develop a vermin controlling agent of which the low dose exhibits a great insecticidal activity and which hardly exerts any adverse effects upon mammals, fishes and beneficial insects, to find

[1] an oxopropionitrile derivative of the formula (1)

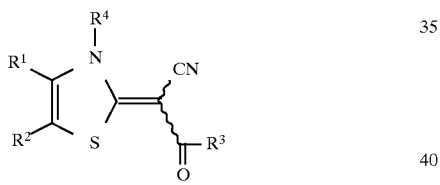

wherein $R^1$ represents a hydrogen or halogen atom, an alkyl group of 2 to 8 carbon atoms, a haloalkyl group of 1 to 6 carbon atoms, an alkenyl group of 2 to 4 carbon atoms, a cycloalkyl group of 3 to 10 carbon atoms optionally substituted with an alkyl group of 1 to 3 carbon atoms, an alkyl group of 1 to 4 carbon atoms substituted with an alkoxycarbony group of which the alkoxyl moiety comprises from 1 to 4 carbon atoms, a pyridyl, naphthyl or thienyl group, or a phenyl group optionally substituted with X;

$R^2$ represents a hydrogen atom, halogen atom, an alkyl group of 1 to 8 carbon atoms, a haloalkyl group of 1 to 6 carbon atoms, a cycloalkyl group of 3 to 10 carbon atoms optionally substituted with an alkyl group of 1 to 3 carbon atoms, or a phenyl group optionally substituted with X;

X represents one or more substituent groups optionally selected from a halogen atom, an alkyl group of 1 to 4 carbon atoms, an alkoxyl group of 1 to 4 carbon atoms, an alkylsulfenyl group of 1 to 4 carbon atoms, an alkylsulfinyl group of 1 to 4 carbon atoms, an alkylsulfonyl group of 1 to 4 carbon atoms, a haloalkyl group of 1 to 4 carbon atoms, a $NO_2$, CN, an alkylcarbonyloxy group of which the alkyl moiety comprises from 1 to 4 carbon atoms, or a dialkylamino group of which the alkyl moieties independently comprise from 1 to 4 carbon atoms, where X may be same or different when the number of X is two or more;

$R^3$ represents a heterocyclic group containing from 1 to 4 heteroatoms as the cyclic members optionally selected from a oxygen, sulfur or nitrogen atom besides the carbon atoms, which is optionally substituted with Y and which is selected from a furan-2-yl, furan-3-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, imidazol-1-yl, imidazol-2-yl, imidazol-4-yl, imidazol-5-yl, isoxazol-3-yl, isoxazol-4-yl, isoxazol-5-yl, isothiazol-3-yl, isothiazol-4-yl, isothiazol-5-yl, pyrazol-1-yl, pyrazol-3-yl, pyrazol-4-yl, pyrazol-5-yl, 1,3,4-oxadiazol-2-yl, 1,3,4-thiadiazol-2-yl, 1,3,4-triazol-1-yl, 1,3,4-triazol-2-yl, 1,2,4-oxadiazol-3-yl, 1,2,4-oxadiazol-5-yl, 1,2,4-thiadiazol-3-yl, 1,2,4-thiadiazol-5-yl, 1,2,4-triazol-1-yl, 1,2,4-triazol-3-yl, 1,2,4-triazol-5-yl, 1,2,3-oxadiazol-4-yl, 1,2,3-oxadiazol-5-yl, 1,2,3-thiadiazol-4-yl, 1,2,3-thiadiazol-5-yl, 1,2,3-triazol-1-yl, 1,2,3-triazol-4-yl, 1,2,3-triazol-5-yl, 1,2,3,4-tetrazol-1-yl, 1,2,3,4-tetrazol-5-yl, 1,2,3,5-tetrazol-1-yl, 1,2,3,5-tetrazol-4-yl, pyridin-2-yl, pyridin-3-yl, pyridin-4-yl, pyrazin-2-yl, pyridazin-3-yl, pyridazin-4-yl, 1,3,5-triazin-2-yl, 1,2,4-triazin-3-yl, 1,2,4-triazin-5-yl, 1,2,4-triazin-6-yl, pyrazolin-1-yl, pyrazolin-3-yl, pyrazolin-4-yl, pyrazolin-5-yl, imidazolin-1-yl, imidazolin-2-yl, imidazolin-4-yl, imidazolin-5-yl, oxazolin-2-yl, oxazolin-4-yl, oxazolin-5-yl, isoxazolin-3-yl, isoxazolin-4-yl, isoxazolin-5-yl, thiazolin-2-yl, thiazolin-4-yl, thiazolin-5-yl, 3(2H)-pyridazinon-2-yl, 3(2H)-pyridazinon-4-yl, 3(2H)-pyridazinon-5-yl or 3(2H)-pyridazinon-6-yl group, a thiophen-2-yl group substituted with Z, or a thiophen-3-yl group substituted with Z;

Y represents one or more substituent groups optionally selected from a halogen atom, an alkyl group of 1 to 4 carbon atoms, an alkoxyl group of 1 to 4 carbon atoms, a haloalkyl group of 1 to 4 carbon atoms, an alkylsulfenyl group of 1 to 4 carbon atoms, an alkylsulfinyl group of 1 to 4 carbon atoms, an alkylsulfonyl group of 1 to 4 carbon atoms, a phenyl, benzyl, phenoxy, nitro, cyano, hydroxyl group, an alkoxyalkyl group of 2 to 4 carbon atoms, an alkylcarbonyl group of 2 to 4 carbon atoms, an alkoxycarbonyl group of which the alkoxyl moiety comprises from 1 to 4 carbon atoms, or a dialkylamino group of which the alkyl moieties independently comprise from 1 to 4 carbon atoms, where Y may be same or different when the number of Y is two or more;

Z represents one or more substituent groups optionally selected from a halogen atom, an alkyl group of 1 to 4 carbon atoms, an alkoxyl group of 1 to 4 carbon atoms, a haloalkyl group of 1 to 4 carbon atoms, an alkylsulfenyl group of 1 to 4 carbon atoms, an alkylsulfinyl group of 1 to 4 carbon atoms, an alkylsulfonyl group of 1 to 4 carbon atoms, a phenyl, benzyl, phenoxy, nitro, cyano, an alkoxycarbonyl group of which the alkoxyl moiety comprises from 1 to 4 carbon atoms, or a dialkylamino group of which the alkyl moieties independently comprise from 1 to 4 carbon atoms, where Z may be same or different when the number of Z is two or more; and R[4] represents a hydrogen atom, an alkyl group of 1 to 4 carbon atoms, a haloalkyl group of 1 to 4 carbon atoms, an alkoxyalkyl group of 2 to 4 carbon atoms, an alkylcarbonyl of 2 to 4 carbon atoms, an alkoxycarbonyl of which the alkoxyl moiety comprises from 1 to 4 carbon atoms, or a phenyl or benzyl group;

[2] the oxopropionitrile derivative of the formula (1) as described in the above [1], wherein R[2] represents a hydrogen atom or an alkyl group of 1 to 8 carbon atoms;

R[3] represents a furan-3-yl group optionally substituted with Y, a pyrrol-2-yl group optionally substituted with Y, a pyrazol-1-yl group optionally substituted with Y, a pyrazol-3-yl group optionally substituted with Y, a pyrazol-4-yl group optionally substituted with Y, a pyrazol-5-yl group optionally substituted with Y, an imidazol-5-yl group optionally substituted with Y, a thiazol-5-yl group optionally substituted with Y, an oxazol-5-yl group optionally substituted with Y, an isoxazol-4-yl group optionally substituted with Y, a 1,2,3-triazol-5-yl group optionally substituted with Y, a 1,2,3-thiadiazol-5-yl group optionally substituted with Y, a pyridin-3-yl group optionally substituted with Y, a pyridin-4-yl group optionally substituted with Y, a pyrazin-2-yl group optionally substituted with Y, a thiophen-2-yl group substituted with Z, or a thiophen-3-yl group substituted with Z;

Y represents one, two or three substituent groups optionally selected from a halogen atom, an alkyl group of 1 to 4 carbon atoms, an alkoxyl group of 1 to 4 carbon atoms, a haloalkyl group of 1 to 4 carbon atoms, an alkylsulfenyl group of 1 to 4 carbon atoms, an alkylsulfinyl group of 1 to 4 carbon atoms, an alkylsulfonyl group of 1 to 4 carbon atoms, a phenyl, benzyl, phenoxy, nitro, cyano, hydroxyl, an alkoxycarbonyl group of which the alkoxyl moiety comprises from 1 to 4 carbon atoms, or a dialkylamino group of which the alkyl moieties independently comprise from 1 to 4 carbon atoms, where Y may be same or different when the number of Y is two or more;

Z represents one or two substituent groups optionally selected from a halogen atom, or an alkyl group of 1 to 4 carbon atoms, where Z may be same or different when the number of Z is two; and R[4] represents a hydrogen atom, or an alkyl group of 1 to 4 carbon atoms;

[3] the oxopropionitrile derivative of the formula (1) as described in the above [2], wherein R[1] represents a phenyl group optionally substituted with X; and R[4] represents a hydrogen atom;

[4] the oxopropionitrile derivative of the formula (1) as described in the above [2], wherein R[3] represents a pyrazol-1-yl group optionally substituted with Y, a pyrazol-3-yl group optionally substituted with Y, a pyrazol-4-yl group optionally substituted with Y, or a pyrazol-5-yl group optionally substituted with Y;

[5] the oxopropionitrile derivative of the formula (1) as described in the above [3], wherein R[3] represents a pyridin-3-yl group optionally substituted with Y, or a pyridin-4-yl group optionally substituted with Y;

[6] the oxopropionitrile derivative of the formula (1) as described in the above [3], wherein R[3] represents a thiazol-5-yl group optionally substituted with Y;

[7] the oxopropionitrile derivative of the formula (1) as described in the above [3], wherein R[3] represents an imidazol-5-yl group optionally substituted with Y;

[8] the oxopropionitrile derivative of the formula (1) as described in the above [1], wherein R[1] and R[2] each independently represents a hydrogen or halogen atom, an alkyl group of 2 to 6 carbon atoms, a haloalkyl group of 1 to 6 carbon atoms, a cycloalkyl group of 3 to 6 carbon atoms optionally substituted with an alkyl group of 1 to 3 carbon atoms, or

where X represents a halogen atom, a $C_{1-4}$ alkyl group, a $C_{1-4}$ alkoxyl group, a $C_{1-4}$ alkylsulfenyl group, a $C_{1-4}$ haloalkylgroup, a nitro, cyano, or a $(C_{1-4}\ alkyl)_2N$ of which the alkyl moieties are same or different; m is an integer from 0 to 5; and X may be same or different when m is an integer from 2 to 5;

R[3] represents

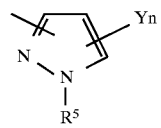

where Y represents a halogen atom, $C_{1-4}$ alkyl group, a $C_{1-4}$ alkoxyl group, a $C_{1-4}$ haloalkyl group, a $C_{1-4}$ alkylsulfenylgroup, a $C_{1-4}$ alkylsulfinyl group, a $C_{1-4}$ alkylsulfonyl group, a phenyl, benzyl, phenoxy, nitro, cyano, a $C_{2-4}$ alkoxycarbonyl group, or a $(C_{1-4}\ alkyl)_2N$ of which the alkyl moieties are same or different; n is an integer from 0 to 2; Y may be same or different when n is 2; and R[5] represents a hydrogen atom, a $C_{1-4}$ alkyl group, a $C_{1-4}$ haloalkyl group, a $C_{2-4}$ alkoxyalkyl group, a $C_{2-4}$ alkylcarbonyl group, or a phenyl or benzyl group; or

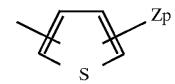

where Z represents a halogen atom, a $C_{1-4}$ alkyl group, a $C_{1-4}$ alkoxyl group, a $C_{1-4}$ haloalkyl group, a $C_{1-4}$ alkylsulfenylgroup, a $C_{1-4}$ alkylsulfinyl group, a $C_{1-4}$ alkylsulfonyl group, a phenyl, benzyl, phenoxy, nitro, cyano, a $C_{2-4}$ alkoxycarbonyl group, or a $(C_{1-4}\ alkyl)_2N$ of which the alkyl moieties are same or different; p is an integer from 1 to 2; an d Z may be same or different when p is 2; and R[4] represents a hydrogen atom, a $C_{1-4}$ alkyl group, a $C_{1-4}$ haloalkyl group, a $C_{2-4}$ alkoxyalkyl group, a $C_{2-4}$ alkylcarbonyl group, a phenyl, or benzyl group;

[9] the oxopropionitrile derivative of the formula (1) as described in the above [8], wherein R[3] represents;

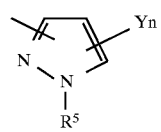

[10] the oxopropionitrile derivative of the formula (1) as described in the above [8], wherein R[3] represents;

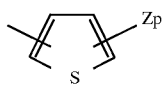

[11] the oxopropionitrile derivative of the formula (1) as described in the above [8], wherein $R^2$ represents a hydrogen atom;

[12] the oxopropionitrile derivatives of the formula (1) as described in the above [11], wherein $R^3$ represents;

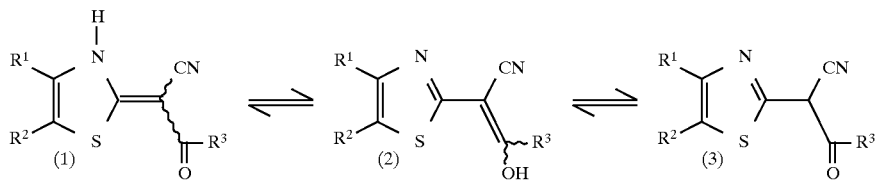

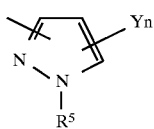

[13] the oxopropionitrile derivative of the formula

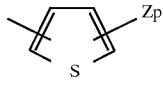

(1) as described in the above [11], wherein $R^3$ represents;

[14] the oxopropionitrile derivative as described in the above [1], selected from the compound group described below consisting of (1) 2-(4-tert-butyl-2,3-dihydrothiazol-2-ylidene)-3-(5-chloro-1-methyl-3-trifluoromethylpyrazol-4-yl)-3-oxopropionitrile,
(2) 2-(4-tert-butyl-2,3-dihydrothiazol-2-ylidene)-3-(3,5-dichloro-1-methylpyrazol-4-yl)-3-oxopropionitrile,
(3) 2-{4-(2,6-difluorophenyl)-2,3-dihydrothiazol-2-ylidene}-3-(5-chloro-1-methyl-3-trifluoromethylpyrazol-4-yl)-3-oxopropionitrile,
(4) 2-{4-(2,6-difluorophenyl)-2,3-dihydrothiazol-2-ylidene}-3-(3,5-dichloro-1-methylpyrazol-4-yl)-3-oxopropionitrile,
(5) 2-{4-(2-chloro-6-fluorophenyl)-2,3-dihydrothiazol-2-ylidene}-3-(5-chloro-1-methyl-3-trifluoromethylpyrazol-4-yl)-3-oxopropionitrile,
(6) 2-{4-(1-naphthyl)-2,3-dihydrothiazol-2-ylidene}-3-(5-chloro-1-methyl-3-trifluoromethylpyrazol-4-yl)-3-oxopropionitrile,
(7) 2-{4-(1-naphthyl)-2,3-dihydrothiazol-2-ylidene)-3-(3,5-dichloro-1-methylpyrazol-4-yl)-3-oxopropionitrile
(8) 2-{4-(2,6-difluorophenyl)-2,3-dihydrothiazol-2-ylidene}-3-(2-chloropyridin-3-yl)-3-oxopropionitrile,
(9) 2-{4-(2,6-difluorophenyl)-2,3-dihydrothiazol-2-ylidene}-3-(2-methoxypyridin-3-yl)-3-oxopropionitrile,
(10) 2-{4-(2,6-difluorophenyl)-2,3-dihydrothiazol-2-ylidene}-3-(2-methylthiopyridin-3-yl)-3-oxopropionitrile, and
(11) 2-{4-(2,6-difluorophenyl)-2,3-dihydrothiazol-2-ylidene}-3-(3,5-dimethylpyrazol-1-yl)-3-oxopropionitrile; and

[15] a pest controlling agent characterized by containing at least one kind of the derivative as described in the above [1] to [14] (hereinafter referred to as the compound of the present invention) as an active ingredient.

It will be appreciated that the compound of the present invention of which the substituent $R^4$ in the formula (1) represents a hydrogen atom may exist in the form of the tautomers represented by the formulae described below.

Said compound is considered to exist mainly in the enolic form (2); however, it may be in the form of the tautomer (1) or (3) under some conditions. The present invention should be appreciated to include all the three tautomers and their mixture. Additionally, when the compound of the present invention has the structure of the tautomer (1) or (2), each includes geometrical isomers, (E)-form and (Z)-form, and it is apparent that the present invention may include both of the (E)-form and (Z)-form and any mixtures of them in consideration that the compound of the present invention may have the structure (3).

Next the example of $R^1$, $R^2$, $R^3$, $R^4$, $R^5$, X, Y, Z, m, n and p in the formula (1) will be described.

The halogen atom in the definition of $R^1$, $R^2$, Z, X and Y is exemplified by a fluorine, chlorine, bromine and iodine atom.

The alkyl group in the definition of $R^1$, $R^2$, $R^4$, $R^6$, X, Y and Z is exemplified by a straight or branched alkyl group such as methyl, ethyl, n-propyl, isopropyl, n-butyl, isobutyl, sec-butyl, tert-butyl, pentyl-1, pentyl-2, pentyl-3, 2-methylbutyl-1, 2-methylbutyl-2, 2-methylbutyl-3, 3-methylbutyl-1, 2,2-dimethylpropyl-2, hexyl-1, hexyl-2, hexyl-3, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl-1, heptyl-2, heptyl-3, 1-ethylpentyl, 1,1-dimethylpentyl, 1-methylheptyl, 2-methylheptyl, octyl-1, octyl-2, octyl-3, 1,1-dimethylhexyl, and 2,2-dimethylhexyl, and each of them is selected in the range of the carbon number defined. The haloalkyl group in the definition of $R^1$, $R^2$, $R^4$, $R^5$, X, Y and Z is exemplified by a fluoromethyl, chloromethyl, bromomethyl, fluoroethyl, chloroethyl, bromoethyl, fluoro-n-propyl, chloro-n-propyl, difluoromethyl, trifluoromethyl, dichloromethyl, trichloromethyl, difluoroethyl, trifluoroethyl, trichloroethyl, chlorodifluoromethyl, trifluorochloroethyl, chlorobutyl, fluorobutyl, 2,2-dichloro-1, 1-dimethylethyl, 2-chloro-1, 1-dimethylethyl, perfluoropentyl, perfluorohexyl group and the like, and each of them is selected in the range of the carbon number defined. The alkenyl group of 2 to 4 carbon atoms in the definition of $R^1$ is exemplified by an ethenyl, 2-propenyl, 1-methylethenyl, 1-methyl-2-propenyl, 2-butenyl, 2-methyl-2-propenyl, 1-ethylethenyl group and the like. The $C_{3-10}$ cycloalkyl group optionally substituted with a $C_{1-3}$ alkyl group in the definition of $R^1$ and $R^2$ is exemplified by a cyclopropyl, 1-methylcyclopropyl, cyclobutyl, cyclopentyl, 1-methylcyclopentyl, cyclohexyl, 1-methylcyclohexyl, adamantyl group and the like.

The alky group substituted with an alkoxycarbonyl group of which the alkoxyl moiety comprises from 1 to 4 carbon atoms in the definition of $R^1$ is exemplified by a methoxycarbonylmethyl, ethoxycarbonylmethyl, n-propoxycarbonylmethyl, isobutoxycarbonylmethyl, 1-methoxycarbonylethyl, 1-methoxycarbonylpropyl, 2-n-butoxycarbonylethyl, 1-methoxycarbonyl-1-methylethyl, 1-ethoxycarbonyl-1-methylethyl, 1-tert-butoxycarbonyl-1-methylethyl, 1-methoxycarbonyl-1-ethylethyl group and the like.

The pyridyl group in the definition of $R^1$ is exemplified by a 2-pyridyl, 3-pyridyl and 4-pyridyl group.

The naphthyl group in the definition of $R^1$ is exemplified by a 1-naphthyl and 2-naphthyl group.

The thienyl group in the definition of $R^1$ is exemplified by a 2-thienyl and 3-thienyl group.

The alkoxyl group of 1 to 4 carbon atoms in the definition of X, Y and Z is exemplified by a straight or branched alkoxyl group of 1 to 4 carbon atoms such as a methoxy, ethoxy, n-propoxy, isopropoxy, n-butoxy, isobutoxy, sec-butoxy and tert-butoxy group.

The alkylsulfenyl group of 1 to 4 carbon atoms in the definition of X, Y and Z is exemplified by a straight or branched alkylsulfenyl group of 1 to 4 carbon atoms such as a methylsulfenyl, ethylsulfenyl, n-propylsulfenyl, isopropylsulfenyl, n-butylsulfenyl, isobutylsulfenyl, sec-butylsulfenyl and tert-butylsulfenyl group.

The alkylsulfinyl group of 1 to 4 carbon atoms in the definition of X, Y and Z is exemplified by a straight or branched alkylsulfinyl group of 1 to 4 carbon atoms such as a methylsulfinyl, ethylsulfinyl, n-propylsulfinyl, isopropylsulfinyl, n-butylsulfinyl, isobutylsulfinyl, sec-butylsulfinyl and tert-butylsulfinyl group.

The alkylsulfonyl group of 1 to 4 carbon atoms in the definition of X, Y and Z is exemplified by a straight or branched alkylsulfonyl group of 1 to 4 carbon atoms such as a methylsulfonyl, ethylsulfonyl, n-propylsulfonyl, isopropylsulfonyl, n-butylsulfonyl, isobutylsulfonyl, sec-butylsulfonyl and tert-butylsulfonyl group.

The di($C_{1-4}$ alkyl)amino group of which the alkyl moieties are same or different in the definition of X, Y and Z is exemplified by a dimethylamino, diethylamino, di-n-propylamino, diisopropylamino, di-n-butylamino, methyethylamino, methylisopropylamino, ethyl-n-butylamino, propylisobutylamino group and the like. The alkylcarbonyl group of 2 to 4 carbon atoms in the definition of Y, $R^4$ and $R^5$ is exemplified by an acetyl, propanoyl, butanoyl, pentanoyl and 2-methylpropanoyl group.

The alkoxycarbonyl group of which the alkoxyl moiety comprises from 1 to 4 carbon atoms in the definition of Y and Z is exemplified by a methoxycarbonyl, ethoxycarbonyl, n-propoxycarbonyl, isopropoxycarbonyl, n-butoxycarbonyl, sec-butoxycarbonyl, isobutoxycarbonyl and tert-butoxycarbonyl group.

The alkoxylalkyl group of 2 to 4 carbon atoms in the definition of Y, $R^4$ and $R^5$ is exemplified by a ($C_{1-3}$ alkoxy)methyl, ($C_{1-2}$ alkoxy)ethyl, methoxypropyl group and the like, such as a methoxymethyl, ethoxymethyl, n-propylmethyl, iso propoxymethyl, methoxyethyl and ethoxyethyl group.

The alkylcarbonyloxy group of which the alkyl moiety comprises from 1 to 4 carbon atoms in the definition of X is exemplified by an acetyloxy, propanoyloxy, butanoyloxy, pentanoyloxy, 2-methylpropanoyloxy, 2-ethylpropanoyloxy, 2,2-dimethylpropanoyloxy and 3-methylbutanoyloxy group.

m includes 0, 1, 2, 3, 4 and 5, and each means that the phenyl group is, respectively, unsubstituted, monosubstituted, disubstituted, trisubstituted, tetrasubstituted and pentasubstituted with X. When the phenyl group is substituted with two or more of X, X may be a combination of the same or different substituents.

n includes 0, 1 and 2, and each means that the pyrazole group is, respectively, unsubstituted, monosubstituted and disubstituted with Z. When the pyrazole group is substituted with two of Y, Y may be a combination of the same or different substituents.

p includes 0, 1 and 2, and each means that the thiophene group is, respectively, unsubstituted, monosubstituted and disubstituted with Z. When the thiophene group is substituted with two of Z, Z may be a combination of the same or different substituents.

Next the range of $R^1$, $R^2$, $R^3$, $R^4$, $R^5$, X, Y, Z, m, n and p in the formula (1) will be described.

The range of $R^1$ includes a hydrogen or halogen atom, an alkyl group of 2 to 8 carbon atoms, a haloalkyl group of 1 to 6 carbon atoms, an alkenyl group of 1 to 4 carbon atoms, a cycloalkyl group of 3 to 10 carbon atoms optionally substituted with an alkyl group of 1 to 3 carbon atoms, an alkyl group of 1 to 4 carbon atoms substituted with an alkoxycarbony group of 2 to 5 carbon atoms, a pyridyl, naphthyl or thienyl group, or a phenyl group optionally substituted with X;

preferably, an alkyl group of 2 to 8 carbon atoms, a haloalkyl group of 1 to 4 carbon atoms, an alkenyl group of 1 to 4 carbon atoms, a cycloalkyl group of 3 to 10 carbon atoms optionally substituted with an alkyl group of 1 to 3 carbon atoms, an alkyl group of 1 to 4 carbon atoms substituted with an alkoxycarbony group of which the alkoxyl moiety comprises 1 to 4 carbon atoms, a pyridyl, 1-naphthyl or 2-thienyl group, or a phenyl group optionally substituted with X;

more preferably, an alkyl group of 3 to 8 carbon atoms, a haloalkyl group of 1 to 4 carbon atoms, an alkenyl group of 1 to 4 carbon atoms, a cycloalkyl group of 3 to 10 carbon atoms optionally substituted with an alkyl group of 1 to 3 carbon atoms, an alkyl group of 1 to 4 carbon atoms substituted with an alkoxycarbony group of which the alkoxyl moiety comprises 1 to 4 carbon atoms, a 2-pyridyl or 1-naphthyl group, or a phenyl group optionally substituted with X; and further preferably, an alkyl group of 3 to 6 carbon atoms, an alkenyl group of 1 to 4 carbon atoms, a cycloalkyl group of 3 to 10 carbon atoms optionally substituted with an alkyl group of 1 to 3 carbon atoms, an alkyl group of 1 to 4 carbon atoms substituted with an alkoxycarbony group of which the alkoxyl moiety comprises 1 to 4 carbon atoms, a 2-pyridyl or 1-naphthyl group, or a phenyl group optionally substituted with X.

The range of $R^2$ includes a hydrogen or halogen atom, an alkyl group of 1 to 8 carbon atoms, a haloalkyl group of 1 to 6 carbon atoms, a cycloalkyl group of 3 to 10 carbon atoms optionally substituted with an alkyl group of 1 to 3 carbon atoms, or a phenyl group optionally substituted with X; preferably, a hydrogen atom or an alkyl group of 1 to 6 carbon atoms; and more preferably, a hydrogen atom.

The range of X includes one or more substituent groups optionally selected from a halogen atom, an alkyl group of 1 to 4 carbon atoms, an alkoxyl group of 1 to 4 carbon atoms, an alkylsulfenyl group of 1 to 4 carbon atoms, an alkylsulfinyl group of 1 to 4 carbon atoms, an alkylsulfonyl group of 1 to 4 carbon atoms, a haloalkyl group of 1 to 4 carbon atoms, a nitro or cyano group, an alkylcarbonyloxy group of which the alkyl moiety comprises from 1 to 4 carbon atoms, or a dialkylamino group of which the alkyl moieties independently comprise from 1 to 4 carbon atoms; preferably, a halogen atom, an alkyl group of 1 to 4 carbon atoms, an alkoxyl group of 1 to 4 carbon atoms, a haloalkyl group of 1 to 4 carbon atoms, a nitro group, or an alkylcarbonyloxy group of which the alkyl moiety comprises from 1 to 4 carbon atoms; more preferably, a halogen atom, an alkyl group of 1 to 4 carbon atoms, an alkoxyl group of 1 to 4 carbon atoms, or a haloalkyl group of 1 to 4 carbon atoms; and further preferably, a halogen atom. The substituting position includes the o-, m- and p-position; preferably, the o- and m-position, and more preferably, the o-position.

When the phenyl group is substituted with the plural substituent groups, the o-, m- and p-position may be combined variously, the substituent groups may be a combination of the same or different ones, and the number of the substituent groups may be at most five, preferably at most three, and more preferably at most two.

The range of $R^3$ includes a heterocyclic group containing from 1 to 4 heteroatoms as the cyclic members optionally selected from a oxygen, sulfur or nitrogen atom besides the carbon atoms, which is optionally substituted with Y and which is selected from a furan-2-yl, furan-3-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, imidazol-1-yl, imidazol-2-yl, imidazol-4-yl, imidazol-5-yl, isoxazol-3-yl, isoxazol-4-yl, isoxazol-5-yl, isothiazol-3-yl, isothiazol-4-yl, isothiazol-5-yl, pyrazol-1-yl,pyrazol-3-yl, pyrazol-4-yl, pyrazol-5-yl, 1,3,4-oxadiazol-2-yl, 1,3,4-thiadiazol-2-yl, 1,3,4-triazol-1-yl, 1,3,4-triazol-2-yl, 1,2,4-oxadiazol-3-yl, 1,2,4-oxadiazol-5-yl, 1,2,4-thiadiazol-3-yl, 1,2,4-thiadiazol-5-yl, 1,2,4-triazol-1-yl, 1,2,4-triazol-3-yl, 1,2,4-triazol-5-yl, 1,2,3-oxadiazol-4-yl, 1,2,3-oxadiazol-5-yl, 1,2,3-thiadiazol-4-yl, 1,2,3-thiadiazol-5-yl, 1,2,3-triazol-1-yl, 1,2,3-triazol-4-yl, 1,2,3-triazol-5-yl, 1,2,3,4-tetrazol-1-yl, 1,2,3,4-tetrazol-5-yl, 1,2,3,5-tetrazol-1-yl, 1,2,3,5-tetrazol-4-yl, pyridin-2-yl, pyridin-3-yl, pyridin-4-yl, pyrazin-2-yl, pyridazin-3-yl, pyridazin-4-yl, 1,3,5-triazin-2-yl, 1,2,4-triazin-3-yl, 1,2,4-triazin-5-yl, 1,2,4-triazin-6-yl, pyrazolin-1-yl, pyrazolin-3-yl, pyrazolin-4-yl, pyrazolin-5-yl, imidazolin-1-yl, imidazolin-2-yl, imidazolin-4-yl, imidazolin-5-yl, oxazolin-2-yl, oxazolin-4-yl, oxazolin-5-yl, isoxazolin-3-yl, isoxazolin-4-yl, isoxazolin-5-yl, thiazolin-2-yl, thiazolin-4-yl, thiazolin-5-yl, 3(2H)-pyridazinon-2-yl, 3(2H)-pyridazinon-4-yl, 3(2H)-pyridazinon-5-yl or 3(2H)-pyridazinon-6-yl group, a thiophen-2-yl group substituted with Z, or a thiophen-3-yl group substituted with Z;

preferably, a furan-2-yl, furan-3-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, imidazol-1-yl, imidazol-2-yl, imidazol-4-yl, imidazol-5-yl, isoxazol-3-yl, isoxazol-4-yl, isoxazol-5-yl, isothiazol-3-yl, isothiazol-4-yl, isothiazol-5-yl, pyrazol-1-yl, pyrazol-3-yl, pyrazol-4-yl, pyrazol-5-yl, 1,3,4-oxadiazol-2-yl, 1,3,4-thiadiazol-2-yl, 1,3,4-triazol-1-yl, 1,3,4-triazol-2-yl, 1,2,4-oxadiazol-3-yl, 1,2,4-oxadiazol-5-yl, 1,2,4-thiadiazol-3-yl, 1,2,4-thiadiazol-5-yl, 1,2,4-triazol-1-yl, 1,2,4-triazol-3-yl, 1,2,4-triazol-5-yl, 1,2,3-oxadiazol-4-yl, 1,2,3-oxadiazol-5-yl, 1,2,3-thiadiazol-4-yl, 1,2,3-thiadiazol-5-yl, 1,2,3-triazol-1-yl, 1,2,3-triazol-4-yl, 1,2,3-triazol-5-yl, 1,2,3,4-tetrazol-1-yl, 1,2,3,4-tetrazol-5-yl, 1,2,3,5-tetrazol-1-yl, 1,2,3,5-tetrazol-4-yl, pyridin-2-yl, pyridin-3-yl, pyridin-4-yl, pyrazin-2-yl, pyridazin-3-yl, pyridazin-4-yl, 1,3,5-triazin-2-yl, 1,2,4-triazin-3-yl, 1,2,4-triazin-5-yl or 1,2,4-triazin-6-yl group;

more preferably, a furan-3-yl group optionally substituted with Y, a pyrrol-2-yl group optionally substituted with Y, a pyrazol-1-yl group optionally substituted with Y, a pyrazol-3-yl group optionally substituted with Y, a pyrazol-4-yl group optionally substituted with Y, a pyrazol-5-yl group optionally substituted with Y, an imidazol-5-yl group optionally substituted with Y, a thiazol-5-yl group optionally substituted with Y, an oxazol-5-yl group optionally substituted with Y, an isoxazol-4-yl group optionally substituted with Y, a 1,2,3-triazol-5-yl group optionally substituted with Y, a 1,2,3-thiadiazol-5-yl group optionally substituted with Y, a pyridin-3-yl group optionally substituted with Y, a pyridin-4-yl group optionally substituted with Y, a pyrazin-2-yl group optionally substituted with Y, a thiophen-2-yl group substituted with Z, or a thiophen-3-yl group substituted with Z;

further preferably, a pyrazol-1-yl group optionally substituted with Y, a pyrazol-3-yl group optionally substituted with Y, a pyrazol-4-yl group optionally substituted with Y, or a pyrazol-5-yl group optionally substituted with Y;

a pyridin-3-yl group optionally substituted with Y, or a pyridin-4-yl group optionally substituted with Y;

an imidazol-5-yl group optionally substituted with Y; and a thiazol-5-3-yl group optionally substituted with Y; and more further preferably, a pyrazol-1-yl group optionally substituted with Y, a pyrazol-3-yl group optionally substituted with Y, a pyrazol-4-yl group optionally substituted with Y, or a pyrazol-5-yl group optionally substituted with Y, or a pyridi n-3-yl group optionally substituted with Y.

The range of Y includes one or more substituent groups optionally selected from a halogen atom, an alkyl group of 1 to 4 carbon atoms, an alkoxyl group of 1 to 4 carbon atoms, a haloalkyl group of 1 to 4 carbon atoms, an alkylsulfenyl group of 1 to 4 carbon atoms, an alkylsulfinyl group of 1 to 4 carbon atoms, an alkylsulfonyl group of 1 to 4 carbon atoms, a phenyl, benzyl, phenoxy, nitro, cyano or hydroxyl group, an alkoxyalkyl group of 2 to 4 carbon atoms, an alkylcarbonyl group of 2 to 4 carbon atoms, an alkoxycarbonyl group of which the alkoxyl moiety comprises from 1 to 4 carbon atoms, or a dialkylamino group of which the alkyl moieties independently comprise from 1 to 4 carbon atoms, where Y may be same or different when the number of Y is two or more; preferably, one or more substituent groups optionally selected from a halogen atom, an alkyl group of 1 to 4 carbon atoms, an alkoxyl group of 1 to 4 carbon atoms, a haloalkyl group of 1 to 4 carbon atoms, an alkylsulfenyl group of 1 to 4 carbon atoms, an alkylsulfinyl group of 1 to 4 carbon atoms, an alkylsulfonyl group of 1 to 4 carbon atoms, a phenyl or hydroxyl group, or an alkoxycarbonyl group of which the alkoxyl moiety comprises from 1 to 4 carbon atoms, where Y may be same or different when the number of Y is two or more; and more preferably, one or more substituent groups optionally selected from a halogen atom, an alkyl group of 1 to 4 carbon atoms, an alkoxyl group of 1 to 4 carbon atoms, a haloalkyl group of 1 to 4 carbon atoms, or an alkylsulfenyl group of 1 to 4 carbon atoms, where Y may be same or different when the number of Y is two or more. Additionally, y represents the one or more substituting groups, preferably, the one, two or three substituting groups.

The range of Z includes one or more substituent groups optionally selected from a halogen atom, an alkyl group of 1 to 4 carbon atoms, an alkoxyl group of 1 to 4 carbon atoms, a haloalkyl group of 1 to 4 carbon atoms, an alkylsulfenyl group of 1 to 4 carbon atoms, an alkylsulfinyl group of 1 to 4 carbon atoms, an alkylsulfonyl group of 1 to 4 carbon atoms, a phenyl, benzyl, phenoxy, nitro or cyano group, an alkoxycarbonyl group of which the alkoxyl moiety comprises from 1 to 4 carbon atoms, or a dialkylamino group of which the alkyl moieties independently comprise from 1 to 4 carbon atoms; preferably, a halogen atom or an alkyl group of 1 to 4 carbon atoms.

The range of $R^4$ includes a hydrogen atom, an alkyl group of 1 to 4 carbon atoms, a haloalkyl group of 1 to 4 carbon atoms, an alkoxyalkyl group of 2 to 4 carbon atoms, an alkylcarbonyl of 2 to 4 carbon atoms, an alkoxycarbonyl of which the alkoxyl moiety comprises from 1 to 4 carbon atoms, or a phenyl or benzyl group; preferably a hydrogen atom or an alkyl group of 1 to 4 carbon atoms; and more preferably, a hydrogen atom.

The compound of the present invention has effect on varieties of noxious insects at the extremely low concentrations of it. The pest are exemplified by agricultural pest such as *Nephotettix cincticeps, Nilaparvata lugens, Myzus persicae, Eplilachna vigintioctopunctata, Spodoptera litura, Cnaphalocrocis medinalis, Plutella xylostella, Mamestra brassicae, Pieris rapae, Agrotis segetum, Archips xylosteanus, Homona coffearia*, tobacco budworm, European corn borer, fall armyworm, corn earworm, southern corn rootworm, northern corn rootworm, and western corn rootworm; red spiders such as *Tetranychus urticae, Panonychus citri*, and *Tetranychus kanzawai*; plant parasitic eelworms such as Cobb root-lesion nematode and Southern root-knot nematode; sanitary vermin such as *Culex pipiens, Musca domestica, Blattella germanica*, ants, fleas, and body lice; storing cereals vermin such as *Sitophilus zeamais, Tenebroides mauritanicus,* and *Cadra cautella;* house vermin such as termites; animal vermin such as mites, fleas, and body lice; house dust acarids such as Acaroidea, Epidermoptidae, and Cheyletidae; and mollusks such as slugs and snails.

Thus the compound of the present invention may effectively control the pest belonging to Orthoptera, Hemiptera, Lepidoptera, Coleoptera, Hymenoptera, Diptera, Isoptera, eelworms, and mites and body louse at the low concentrations of it. On the other hand, the compound of the present invention hardly exerts any adverse effects upon mammals, fishes, beetles and beneficial insects, and it is an extremely useful compound.

The compound of the present invention may be synthesized by the method (scheme 1) described below.

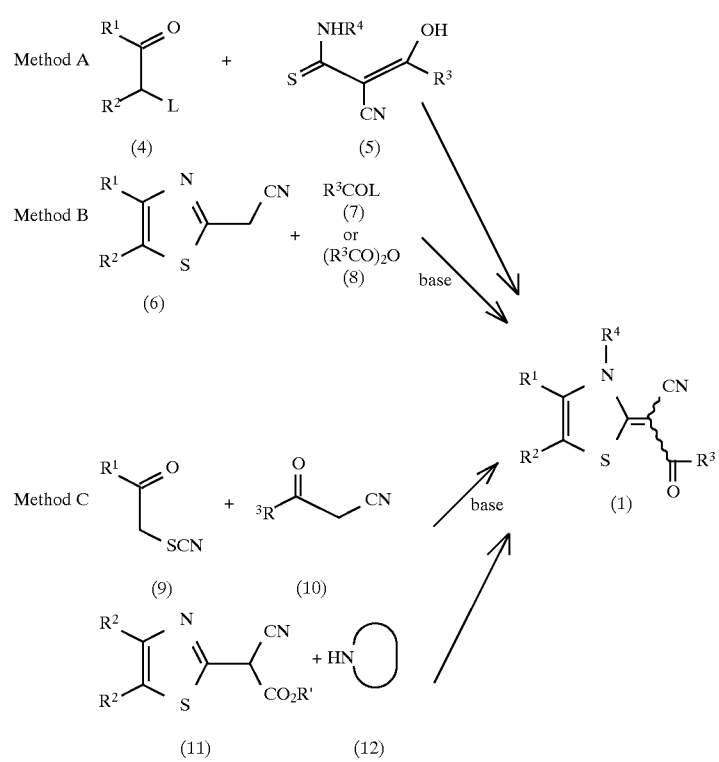

wherein $R^1$, $R^2$, $R^3$ and $R^4$ are as defined above; L represents a chlorine, bromine or iodine atom, or a 1-imidazolyl or 1-pyrazolyl group; and $R^1$ represents a lower alkyl group.

Method A in scheme 1 represents a method of synthesizing the compound of the present invention by allowing a halogenoket one derivative of the general formula (4) to react with a cyanothioacetamide derivative of the general formula (5).

Method B represents a method of synthesizing the compound of the present invention by allowing a thiazolyacetonitrile derivative of the general formula (6) to react with an acid halide, a 1-acylimidazole derivative or a 1-acylpyrazole derivative of the general formula (7), or an acid anhydride of the general formula (8) in the presence of a base.

Method C represents a method of synthesizing the compound of the present invention by allowing an α-thiocyanate ketone derivative of the general formula (9) to react with a cyanoketone derivative of the general formula (10) in the presence of a base.

Method D represents a method of synthesizing the compound of the present invention from a cyanoacetic derivative of the general formula (11) and a heterocyclic compound of the general formula (12). Using method D, a compound in the type that the nitrogen atom in the heterocycle binds the oxopropionitrile moiety may be synthesized. In this case, the heterocyclic compound (12) used as the material is that has a sec-amino group as the cyclic member. Additionally, the compound of the general formula (11) may be synthesized by allowing the thiazolylacetonitrile derivative of the general formula (6) described in method B to react with a carbonic ester in the presence of a base.

The thiazolylacetonitrile derivative (6) used as the material in method B may be synthesized by allowing an α-halogenoketone derivative, an α-halogenoaldehyde derivative, an α-halogenoacetal derivative, or their equivalents to react with cyanothioacetamide.

The base used in the methods described in scheme 1 is exemplified by an alkali metal alkoxide such as sodium ethoxide, sodium methoxide, and potassium t-butoxide; an alkali metal hydroxide such as sodium hydroxide and potassium hydroxide; an alkali metal carbonate such as sodium carbonate and potassium carbonate; an organic base such as triethylamine and pyridine; or sodium hydride.

The reactions represented in scheme 1 may be carried out in an inert solvent and the solvent is exemplified by lower alcohols such as methanol and ethanol; aromatic hydrocarbons such as benzene and toluene; ethers such as diethyl ether, tetrahydrofuran, 1,4-dioxan, 1,2-dimethoxyethane, and 1,2-diethoxyethane; halogenated hydrocarbons such as methylene chloride, chloroform, and 1,2-dichloroethane; amides such as dimethylformamide and dimethylacetamide; acetonitrile; dimethylsulfoxide; or mixed solvents of them.

When occasion demands, a mixed solvent of these solvents and water may be used, and the addition of quaternary ammonium salt such as tetra-n-butylammonium bromide as a catalyst may give a favorable result. The reaction temperature may be controlled optionally at −30° C. to 200° C., and preferably at 0° C. to 150° C. or at 0° C. to the boiling point of the solvent when a solvent is used. The amount of the base used is from 0.05 to 10 equivalents, preferably from 0.05 to 3 equivalents, to the reaction substrate.

The compound of the present invention may be obtained from the reaction mixture in the usual way, and it may be isolated and purified by optional purification methods such as column chromatography when necessary.

When the compound included in the present invention has asymmetric carbon atom(s), the optically active compounds, (+)-body and (−)-body, are included in the present invention.

Examples of the compound included in the present invention will be described below. The abbreviations in the tables are as follows: Me, a methyl group; Et, an ethyl group; Pr, a propyl group; Bu, a butyl group; Pen, a pentyl group; Hex, a hexyl group; Hep, a heptyl group; Oct, an octyl group; Ph, a phenyl group; n, normal; s, secondary; t, tertiary; c, cyclo; Q,

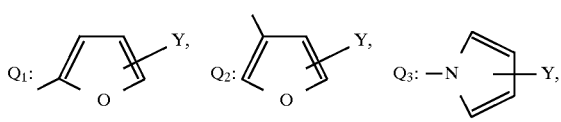

-continued

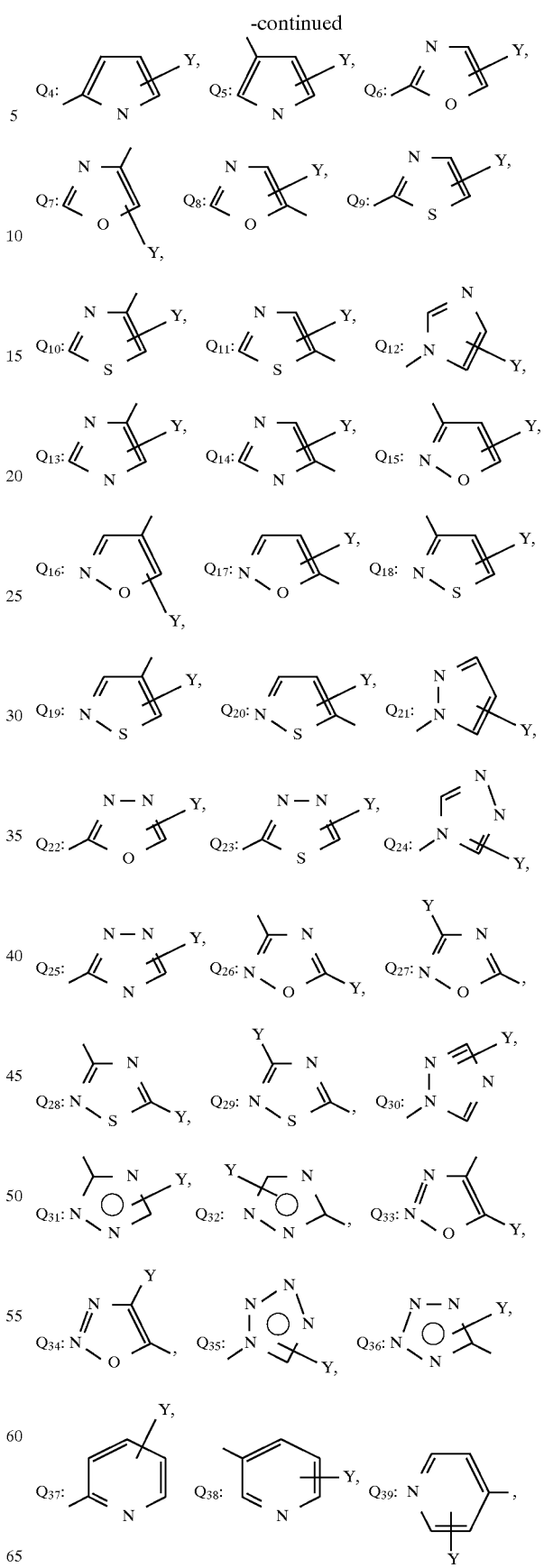

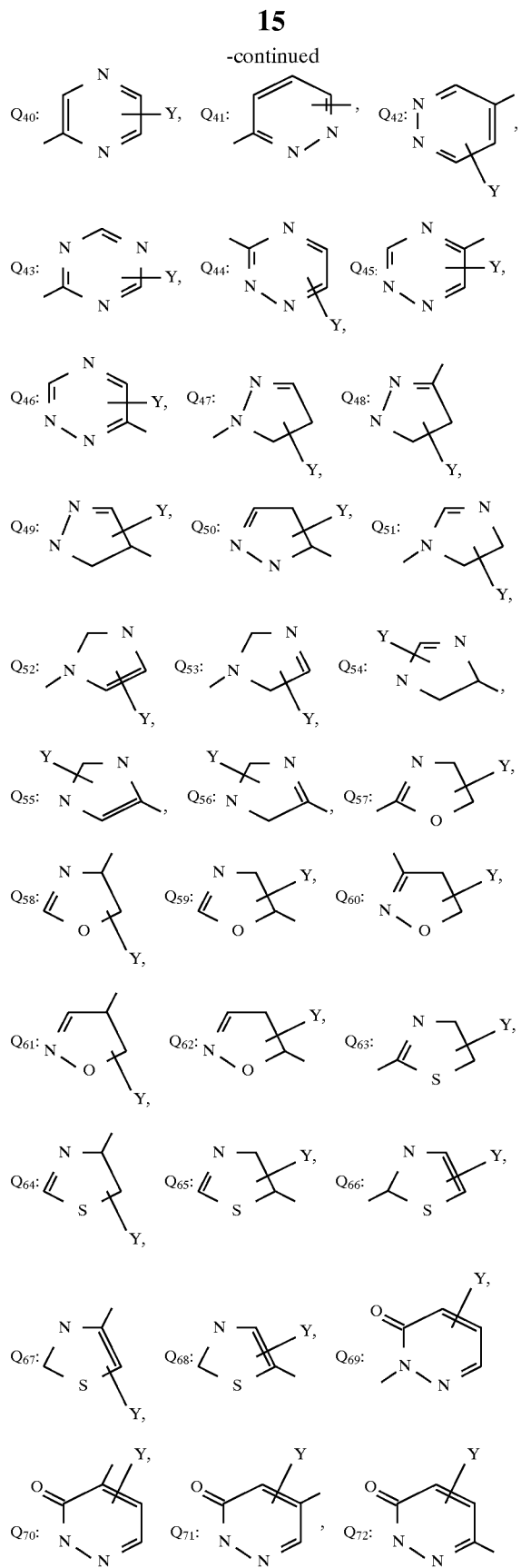
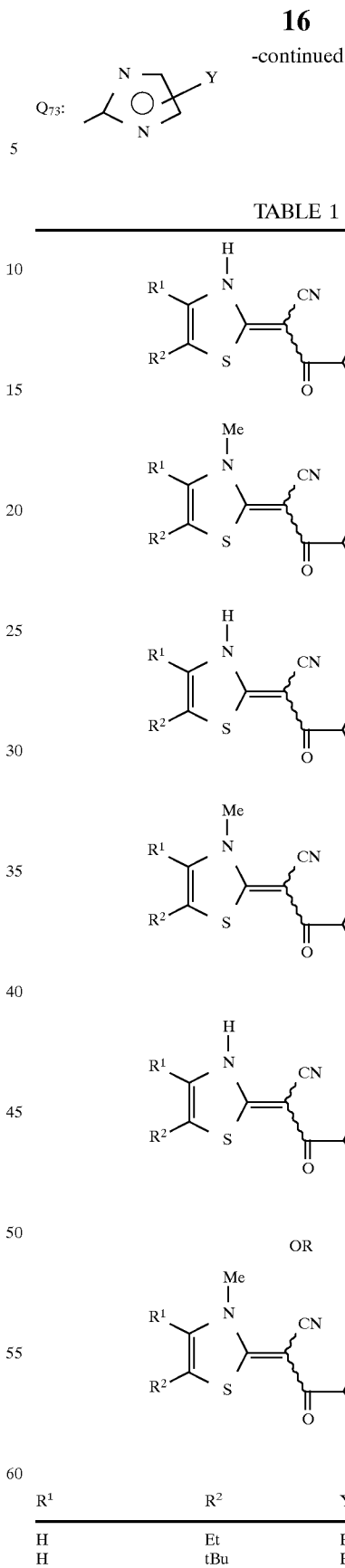
TABLE 1
| $R^1$ | $R^2$ | $Y^1$ | $Y^2$ | $Y^3$ |
|---|---|---|---|---|
| H | Et | H | H | H |
| H | tBu | H | H | Me |
| H | tPen | H | H | Et |
| H | tBuCH$_2$ | H | H | tBu |
| H | MeCH$_2$CH$_2$CMe$_2$ | H | H | CF$_3$ |

TABLE 1-continued

| | | | | |
|---|---|---|---|---|
| H | Me(CH$_2$)$_4$CMe$_2$ | H | H | COCH$_3$ |
| H | 1-Me-cPr | H | H | CH$_2$OCH$_3$ |
| H | cHex | H | H | Ph |
| H | 1-Me-cHex | H | Me | H |
| H | 1-adamanthyl | H | Me | Me |
| H | Ph | H | Me | Et |
| H | 2,6-Cl$_2$—Ph | H | Me | tBu |
| H | 2-F—Ph | H | Me | CF$_3$ |
| cPen | H | Cl | Cl | Me |
| cHex | H | Me | Cl | Me |
| cHex | H | CF$_3$ | Cl | Me |
| cHex | H | Cl | Cl | Me |
| C$_2$F$_5$ | H | Me | Cl | Me |
| C$_2$F$_5$ | H | CF$_3$ | Cl | Me |
| C$_2$F$_5$ | H | Cl | Cl | Me |
| H | Cl | H | Et | CF$_3$ |
| H | CF$_3$ | H | Et | COCH$_3$ |
| H | C$_2$F$_5$ | H | Et | CH$_2$OCH$_3$ |
| Cl | Ph | H | Et | Ph |
| tPen | H | H | iPr | H |
| nOct | H | H | iPr | Me |
| nC$_3$F$_7$ | H | H | iPr | Et |
| cHex | H | H | iPr | tBu |
| 1-Me-cHex | H | H | iPr | CF$_3$ |
| 1-adamanthyl | H | H | iPr | COCH$_3$ |
| Ph | Et | H | iPr | CH$_2$OCH$_3$ |
| 2,6-Cl$_2$—Ph | nBu | H | iPr | Ph |
| 2-F—Ph | nHep | H | tBu | H |
| 2-pyridinyl | H | H | tBu | Me |
| 3-pyridinyl | H | H | tBu | Et |
| 4-pyridinyl | H | H | tBu | tBu |
| 1-naphthyl | H | H | tBu | CF$_3$ |
| 2-naphthyl | H | H | tBu | COCH$_3$ |
| 2-thienyl | H | H | tBu | CH$_2$OCH$_3$ |
| 3-thienyl | H | H | tBu | Ph |
| CH$_2$=CMe | H | H | Ph | H |
| MeCH=CMe | H | H | Ph | Me |
| MeC(Cl)Me | H | H | Ph | Et |
| MeCH$_2$C(Br)Me | H | H | Ph | tBu |
| CCl$_2$CMe$_2$ | H | H | Ph | CF$_3$ |
| Ph | H | H | Ph | COCH$_3$ |
| Ph | H | H | Ph | CH$_2$OCH$_3$ |
| Ph | H | H | Ph | Ph |
| Ph | H | H | F | H |
| Ph | H | H | F | Me |
| Ph | H | H | F | Et |
| Ph | H | H | F | tBu |
| Ph | H | H | F | CF$_3$ |
| Ph | H | H | F | COCH$_3$ |
| Ph | H | H | F | CH$_2$OCH$_3$ |
| Ph | H | H | F | Ph |
| Ph | H | H | Cl | H |
| Ph | H | H | Cl | Me |
| Ph | H | H | Cl | Et |
| Ph | H | H | Cl | tBu |
| Ph | H | H | Cl | CF$_3$ |
| Ph | H | H | Cl | COCH$_3$ |
| Ph | H | H | Cl | CH$_2$OCH$_3$ |
| Ph | H | H | Cl | Ph |
| Ph | H | H | Br | H |
| Ph | H | H | Br | Me |
| Ph | H | H | Br | Et |
| Ph | H | H | Br | tBu |
| Ph | H | H | Br | CF$_3$ |
| Ph | H | H | Br | COCH$_3$ |
| Ph | H | H | Br | CH$_2$OCH$_3$ |
| Ph | H | H | Br | Ph |
| Ph | H | H | CF$_3$ | H |
| Ph | H | H | CF$_3$ | Me |
| Ph | H | H | CF$_3$ | Et |
| Ph | H | H | CF$_3$ | tBu |
| Ph | H | H | CF$_3$ | CF$_3$ |
| Ph | H | H | CF$_3$ | COCH$_3$ |
| Ph | H | H | CF$_3$ | CH$_2$OCH$_3$ |
| Ph | H | H | CF$_3$ | Ph |
| Ph | H | H | OH | H |
| Ph | H | H | OH | Me |
| Ph | H | H | OH | Et |
| Ph | H | H | OH | tBu |
| Ph | H | H | OH | CF$_3$ |
| Ph | H | H | OH | COCH$_3$ |
| Ph | H | H | OH | CH$_2$OCH$_3$ |
| Ph | H | H | OH | Ph |
| Ph | H | H | OMe | H |
| 2-MeS—Ph | H | H | OMe | Me |
| 2-EtS—Ph | H | H | OMe | Et |
| 2-nBuS—Ph | H | H | OMe | tBu |
| 2-MeSO—Ph | H | H | OMe | CF$_3$ |
| 2-EtSO—Ph | H | H | OMe | COCH$_3$ |
| 2-nBuSO—Ph | H | H | OMe | CH$_2$OCH$_3$ |
| 2-MeSO$_2$—Ph | H | H | OMe | Ph |
| 2-EtSO$_2$—Ph | H | H | SMe | H |
| 2-nBuSO$_2$—Ph | H | H | SMe | Me |
| 2-EtC(=O)O—Ph | H | H | SMe | Et |
| 2-nPrC(=O)O—Ph | H | H | SMe | tBu |
| 2-MeC(=O)O—Ph | H | H | SMe | CF$_3$ |
| 2-iPrC(=O)O—Ph | H | H | SMe | COCH$_3$ |
| 2-nBuC(=O)O—Ph | H | H | SMe | CH$_2$OCH$_3$ |
| 2-tBuC(=O)O—Ph | H | H | SMe | Ph |
| 3-Me$_2$N—Ph | H | H | NO$_2$ | H |
| 4-nBu$_2$N—Ph | H | H | NO$_2$ | Me |
| 2-EtMeN—Ph | H | H | NO$_2$ | Et |
| 2,3,4-Cl$_3$—Ph | H | H | NO$_2$ | tBu |
| 2,4,6-F$_3$—Ph | H | H | NO$_2$ | CF$_3$ |
| 2,3,4,5,6-F$_5$—Ph | H | H | NO$_2$ | COCH$_3$ |
| Ph | H | H | NO$_2$ | CH$_2$OCH$_3$ |
| Ph | H | H | NO$_2$ | Ph |
| Ph | H | H | CN | H |
| Ph | H | H | CN | Me |
| Ph | H | H | CN | Et |
| Ph | H | H | CN | CF$_3$ |
| Ph | H | H | CN | COCH$_3$ |
| Ph | H | H | CN | CH$_2$OCH$_3$ |
| Ph | H | H | CN | Ph |
| Ph | H | H | CO$_2$Me | H |
| Ph | H | H | CO$_2$Me | Me |
| Ph | H | H | CO$_2$Me | Et |
| Ph | H | H | CO$_2$Me | tBu |
| Ph | H | H | CO$_2$Me | CF$_3$ |
| Ph | H | H | CO$_2$Me | COCH$_3$ |
| Ph | H | H | CO$_2$Me | CH$_2$OCH$_3$ |
| Ph | H | H | CO$_2$Me | Ph |
| Ph | H | H | NMe$_2$ | H |
| Ph | H | H | NMe$_2$ | Me |
| Ph | H | H | NMe$_2$ | Et |
| Ph | H | H | NMe$_2$ | tBu |
| Ph | H | H | NMe$_2$ | CF$_3$ |
| Ph | H | H | NMe$_2$ | COCH$_3$ |
| Ph | H | H | NMe$_2$ | CH$_2$OCH$_3$ |
| Ph | H | H | NMe$_2$ | Ph |
| Ph | H | Me | H | H |
| Ph | H | Me | H | Me |
| Ph | H | Me | H | Et |
| Ph | H | Me | H | tBu |
| Ph | H | Me | H | CF$_3$ |
| Ph | H | Me | H | COCH$_3$ |
| Ph | H | Me | H | CH$_2$OCH$_3$ |
| Ph | H | Me | H | Ph |
| Ph | H | Me | Me | H |
| Ph | H | Me | Me | Me |
| Ph | H | Me | Me | Et |
| Ph | H | Me | Me | tBu |
| Ph | H | Me | Me | CF$_3$ |
| Ph | H | Me | Me | COCH$_3$ |
| Ph | H | Me | Me | CH$_2$OCH$_3$ |
| Ph | H | Me | Me | Ph |
| Ph | H | Me | Et | H |
| Ph | H | Me | Et | Me |
| Ph | H | Me | Et | Et |
| Ph | H | Me | Et | tBu |
| Ph | H | Me | Et | CF$_3$ |
| Ph | H | Me | Et | COCH$_3$ |
| Ph | H | Me | Et | CH$_2$OCH$_3$ |
| Ph | H | Me | Et | Ph |
| Ph | H | Me | iPr | H |
| Ph | H | Me | iPr | Me |
| Ph | H | Me | iPr | Et |

TABLE 1-continued

| | | | | |
|---|---|---|---|---|
| Ph | H | Me | iPr | tBu |
| Ph | H | Me | iPr | CF$_3$ |
| Ph | H | Me | iPr | COCH$_3$ |
| Ph | H | Me | iPr | CH$_2$OCH$_3$ |
| Ph | H | Me | iPr | Ph |
| Ph | H | Me | tBu | H |
| Ph | H | Me | tBu | Me |
| Ph | H | Me | tBu | Et |
| Ph | H | Me | tBu | tBu |
| Ph | H | Me | tBu | CF$_3$ |
| Ph | H | Me | tBu | COCH$_3$ |
| Ph | H | Me | tBu | CH$_2$OCH$_3$ |
| Ph | H | Me | tBu | Ph |
| Ph | H | Me | Ph | H |
| Ph | H | Me | Ph | Me |
| Ph | H | Me | Ph | Et |
| Ph | H | Me | Ph | tBu |
| Ph | H | Me | Ph | CF$_3$ |
| Ph | H | Me | Ph | COCH$_3$ |
| Ph | H | Me | Ph | CH$_2$OCH$_3$ |
| Ph | H | Me | Ph | Ph |
| Ph | H | Me | F | H |
| Ph | H | Me | F | Me |
| Ph | H | Me | F | Et |
| Ph | H | Me | F | tBu |
| Ph | H | Me | F | CF$_3$ |
| Ph | H | Me | F | COCH$_3$ |
| Ph | H | Me | F | CH$_2$OCH$_3$ |
| Ph | H | Me | F | Ph |
| Ph | H | Me | Cl | H |
| Ph | H | Me | Cl | Me |
| Ph | H | Me | Cl | Et |
| Ph | H | Me | Cl | tBu |
| Ph | H | Me | Cl | CF$_3$ |
| Ph | H | Me | Cl | COCH$_3$ |
| Ph | H | Me | Cl | CH$_2$OCH$_3$ |
| Ph | H | Me | Cl | Ph |
| Ph | H | Me | Br | H |
| Ph | H | Me | Br | Me |
| Ph | H | Me | Br | Et |
| Ph | H | Me | Br | tBu |
| Ph | H | Me | Br | CF$_3$ |
| Ph | H | Me | Br | COCH$_3$ |
| Ph | H | Me | Br | CH$_2$OCH$_3$ |
| Ph | H | Me | Br | Ph |
| Ph | H | Me | CF$_3$ | H |
| Ph | H | Me | CF$_3$ | Me |
| Ph | H | Me | CF$_3$ | Et |
| Ph | H | Me | CF$_3$ | tBu |
| Ph | H | Me | CF$_3$ | CF$_3$ |
| Ph | H | Me | CF$_3$ | COCH$_3$ |
| Ph | H | Me | CF$_3$ | CH$_2$OCH$_3$ |
| Ph | H | Me | CF$_3$ | Ph |
| Ph | H | Me | OH | H |
| Ph | H | Me | OH | Me |
| Ph | H | Me | OH | Et |
| Ph | H | Me | OH | tBu |
| Ph | H | Me | OH | CF$_3$ |
| Ph | H | Me | OH | COCH$_3$ |
| Ph | H | Me | OH | CH$_2$OCH$_3$ |
| Ph | H | Me | OH | Ph |
| Ph | H | Me | OMe | H |
| Ph | H | Me | OMe | Me |
| Ph | H | Me | OMe | Et |
| Ph | H | Me | OMe | tBu |
| Ph | H | Me | OMe | CF$_3$ |
| Ph | H | Me | OMe | COCH$_3$ |
| Ph | H | Me | OMe | CH$_2$OCH$_3$ |
| Ph | H | Me | OMe | Ph |
| Ph | H | Me | SMe | H |
| Ph | H | Me | SMe | Me |
| Ph | H | Me | SMe | Et |
| Ph | H | Me | SMe | tBu |
| Ph | H | Me | SMe | CF$_3$ |
| Ph | H | Me | SMe | COCH$_3$ |
| Ph | H | Me | SMe | CH$_2$OCH$_3$ |
| Ph | H | Me | SMe | Ph |
| Ph | H | Me | NO$_2$ | H |
| Ph | H | Me | NO$_2$ | Me |
| Ph | H | Me | NO$_2$ | Et |
| Ph | H | Me | NO$_2$ | tBu |
| Ph | H | Me | NO$_2$ | CF$_3$ |
| Ph | H | Me | NO$_2$ | COCH$_3$ |
| Ph | H | Me | NO$_2$ | CH$_2$OCH$_3$ |
| Ph | H | Me | NO$_2$ | Ph |
| Ph | H | Me | CN | H |
| Ph | H | Me | CN | Me |
| Ph | H | Me | CN | Et |
| Ph | H | Me | CN | tBu |
| Ph | H | Me | CN | CF$_3$ |
| Ph | H | Me | CN | COCH$_3$ |
| Ph | H | Me | CN | CH$_2$OCH$_3$ |
| Ph | H | Me | CN | Ph |
| Ph | H | Me | CO$_2$Me | H |
| Ph | H | Me | CO$_2$Me | Me |
| Ph | H | Me | CO$_2$Me | Et |
| Ph | H | Me | CO$_2$Me | tBu |
| Ph | H | Me | CO$_2$Me | CF$_3$ |
| Ph | H | Me | CO$_2$Me | COCH$_3$ |
| Ph | H | Me | CO$_2$Me | CH$_2$OCH$_3$ |
| Ph | H | Me | CO$_2$Me | Ph |
| Ph | H | Me | NMe$_2$ | H |
| Ph | H | Me | NMe$_2$ | Me |
| Ph | H | Me | NMe$_2$ | Et |
| Ph | H | Me | NMe$_2$ | tBu |
| Ph | H | Me | NMe$_2$ | CF$_3$ |
| Ph | H | Me | NMe$_2$ | COCH$_3$ |
| Ph | H | Me | NMe$_2$ | CH$_2$OCH$_3$ |
| Ph | H | Me | NMe$_2$ | Ph |
| Ph | H | Et | H | H |
| Ph | H | Et | H | Me |
| Ph | H | Et | H | Et |
| Ph | H | Et | H | tBu |
| Ph | H | Et | H | CF$_3$ |
| Ph | H | Et | H | COCH$_3$ |
| Ph | H | Et | H | CH$_2$OCH$_3$ |
| Ph | H | Et | H | Ph |
| Ph | H | Et | Me | H |
| Ph | H | Et | Me | Me |
| Ph | H | Et | Me | Et |
| Ph | H | Et | Me | tBu |
| Ph | H | Et | Me | CF$_3$ |
| Ph | H | Et | Me | COCH$_3$ |
| Ph | H | Et | Me | CH$_2$OCH$_3$ |
| Ph | H | Et | Me | Ph |
| Ph | H | Et | Et | H |
| Ph | H | Et | Et | Me |
| Ph | H | Et | Et | Et |
| Ph | H | Et | Et | tBu |
| Ph | H | Et | Et | CF$_3$ |
| Ph | H | Et | Et | COCH$_3$ |
| Ph | H | Et | Et | CH$_2$OCH$_3$ |
| Ph | H | Et | Et | Ph |
| Ph | H | Et | iPr | H |
| Ph | H | Et | iPr | Me |
| Ph | H | Et | iPr | Et |
| Ph | H | Et | iPr | tBu |
| Ph | H | Et | iPr | CF$_3$ |
| Ph | H | Et | iPr | COCH$_3$ |
| Ph | H | Et | iPr | CH$_2$OCH$_3$ |
| Ph | H | Et | iPr | Ph |
| Ph | H | Et | tBu | H |
| Ph | H | Et | tBu | Me |
| Ph | H | Et | tBu | Et |
| Ph | H | Et | tBu | tBu |
| Ph | H | Et | tBu | CF$_3$ |
| Ph | H | Et | tBu | COCH$_3$ |
| Ph | H | Et | tBu | CH$_2$OCH$_3$ |
| Ph | H | Et | tBu | Ph |
| Ph | H | Et | Ph | H |
| Ph | H | Et | Ph | Me |
| Ph | H | Et | Ph | Et |
| Ph | H | Et | Ph | tBu |
| Ph | H | Et | Ph | CF$_3$ |
| Ph | H | Et | Ph | COCH$_3$ |
| Ph | H | Et | Ph | CH$_2$OCH$_3$ |
| Ph | H | Et | Ph | Ph |
| Ph | H | Et | F | H |

TABLE 1-continued

| | | | | |
|---|---|---|---|---|
| Ph | H | Et | F | Me |
| Ph | H | Et | F | Et |
| Ph | H | Et | F | tBu |
| Ph | H | Et | F | $CF_3$ |
| Ph | H | Et | F | $COCH_3$ |
| Ph | H | Et | F | $CH_2OCH_3$ |
| Ph | H | Et | F | Ph |
| Ph | H | Et | Cl | H |
| Ph | H | Et | Cl | Me |
| Ph | H | Et | Cl | Et |
| Ph | H | Et | Cl | tBu |
| Ph | H | Et | Cl | $CF_3$ |
| Ph | H | Et | Cl | $COCH_3$ |
| Ph | H | Et | Cl | $CH_2OCH_3$ |
| Ph | H | Et | Cl | Ph |
| Ph | H | Et | Br | H |
| Ph | H | Et | Br | Me |
| Ph | H | Et | Br | Et |
| Ph | H | Et | Br | tBu |
| Ph | H | Et | Br | $CF_3$ |
| Ph | H | Et | Br | $COCH_3$ |
| Ph | H | Et | Br | $CH_2OCH_3$ |
| Ph | H | Et | Br | Ph |
| Ph | H | Et | $CF_3$ | H |
| Ph | H | Et | $CF_3$ | Me |
| Ph | H | Et | $CF_3$ | Et |
| Ph | H | Et | $CF_3$ | tBu |
| Ph | H | Et | $CF_3$ | $CF_3$ |
| Ph | H | Et | $CF_3$ | $COCH_3$ |
| Ph | H | Et | $CF_3$ | $CH_2OCH_3$ |
| Ph | H | Et | $CF_3$ | Ph |
| Ph | H | Et | OH | H |
| Ph | H | Et | OH | Me |
| Ph | H | Et | OH | Et |
| Ph | H | Et | OH | tBu |
| Ph | H | Et | OH | $CF_3$ |
| Ph | H | Et | OH | $COCH_3$ |
| Ph | H | Et | OH | $CH_2OCH_3$ |
| Ph | H | Et | OH | Ph |
| Ph | H | Et | OMe | H |
| Ph | H | Et | OMe | Me |
| Ph | H | Et | OMe | Et |
| Ph | H | Et | OMe | tBu |
| Ph | H | Et | OMe | $CF_3$ |
| Ph | H | Et | OMe | $COCH_3$ |
| Ph | H | Et | OMe | $CH_2OCH_3$ |
| Ph | H | Et | OMe | Ph |
| Ph | H | Et | SMe | H |
| Ph | H | Et | SMe | Me |
| Ph | H | Et | SMe | Et |
| Ph | H | Et | SMe | tBu |
| Ph | H | Et | SMe | $CF_3$ |
| Ph | H | Et | SMe | $COCH_3$ |
| Ph | H | Et | SMe | $CH_2OCH_3$ |
| Ph | H | Et | SMe | Ph |
| Ph | H | Et | $NO_2$ | H |
| Ph | H | Et | $NO_2$ | Me |
| Ph | H | Et | $NO_2$ | Et |
| Ph | H | Et | $NO_2$ | tBu |
| Ph | H | Et | $NO_2$ | $CF_3$ |
| Ph | H | Et | $NO_2$ | $COCH_3$ |
| Ph | H | Et | $NO_2$ | $CH_2OCH_3$ |
| Ph | H | Et | $NO_2$ | Ph |
| Ph | H | Et | CN | H |
| Ph | H | Et | CN | Me |
| Ph | H | Et | CN | Et |
| Ph | H | Et | CN | tBu |
| Ph | H | Et | CN | $CF_3$ |
| Ph | H | Et | CN | $COCH_3$ |
| Ph | H | Et | CN | $CH_2OCH_3$ |
| Ph | H | Et | CN | Ph |
| Ph | H | Et | $CO_2Me$ | H |
| Ph | H | Et | $CO_2Me$ | Me |
| Ph | H | Et | $CO_2Me$ | Et |
| Ph | H | Et | $CO_2Me$ | tBu |
| Ph | H | Et | $CO_2Me$ | $CF_3$ |
| Ph | H | Et | $CO_2Me$ | $COCH_3$ |
| Ph | H | Et | $CO_2Me$ | $CH_2OCH_3$ |
| Ph | H | Et | $CO_2Me$ | Ph |
| Ph | H | Et | $NMe_2$ | H |
| Ph | H | Et | $NMe_2$ | Me |
| Ph | H | Et | $NMe_2$ | Et |
| Ph | H | Et | $NMe_2$ | tBu |
| Ph | H | Et | $NMe_2$ | $CF_3$ |
| Ph | H | Et | $NMe_2$ | $COCH_3$ |
| Ph | H | Et | $NMe_2$ | $CH_2OCH_3$ |
| Ph | H | Et | $NMe_2$ | Ph |
| Ph | H | iPr | H | H |
| Ph | H | iPr | H | Me |
| Ph | H | iPr | H | Et |
| Ph | H | iPr | H | tBu |
| Ph | H | iPr | H | $CF_3$ |
| Ph | H | iPr | H | $COCH_3$ |
| Ph | H | iPr | H | $CH_2OCH_3$ |
| Ph | H | iPr | H | Ph |
| Ph | H | iPr | Me | H |
| Ph | H | iPr | Me | Me |
| Ph | H | iPr | Me | Et |
| Ph | H | iPr | Me | tBu |
| Ph | H | iPr | Me | $CF_3$ |
| Ph | H | iPr | Me | $COCH_3$ |
| Ph | H | iPr | Me | $CH_2OCH_3$ |
| Ph | H | iPr | Me | Ph |
| Ph | H | iPr | Et | H |
| Ph | H | iPr | Et | Me |
| Ph | H | iPr | Et | Et |
| Ph | H | iPr | Et | tBu |
| Ph | H | iPr | Et | $CF_3$ |
| Ph | H | iPr | Et | $COCH_3$ |
| Ph | H | iPr | Et | $CH_2OCH_3$ |
| Ph | H | iPr | Et | Ph |
| Ph | H | iPr | iPr | H |
| Ph | H | iPr | iPr | Me |
| Ph | H | iPr | iPr | Et |
| Ph | H | iPr | iPr | tBu |
| Ph | H | iPr | iPr | $CF_3$ |
| Ph | H | iPr | iPr | $COCH_3$ |
| Ph | H | iPr | iPr | $CH_2OCH_3$ |
| Ph | H | iPr | iPr | Ph |
| Ph | H | iPr | tBu | H |
| Ph | H | iPr | tBu | Me |
| Ph | H | iPr | tBu | Et |
| Ph | H | iPr | tBu | tBu |
| Ph | H | iPr | tBu | $CF_3$ |
| Ph | H | iPr | tBu | $COCH_3$ |
| Ph | H | iPr | tBu | $CH_2OCH_3$ |
| Ph | H | iPr | tBu | Ph |
| Ph | H | iPr | Ph | H |
| Ph | H | iPr | Ph | Me |
| Ph | H | iPr | Ph | Et |
| Ph | H | iPr | Ph | tBu |
| Ph | H | iPr | Ph | $CF_3$ |
| Ph | H | iPr | Ph | $COCH_3$ |
| Ph | H | iPr | Ph | $CH_2OCH_3$ |
| Ph | H | iPr | Ph | Ph |
| Ph | H | iPr | F | H |
| Ph | H | iPr | F | Me |
| Ph | H | iPr | F | Et |
| Ph | H | iPr | F | tBu |
| Ph | H | iPr | F | $CF_3$ |
| Ph | H | iPr | F | $COCH_3$ |
| Ph | H | iPr | F | $CH_2OCH_3$ |
| Ph | Me | iPr | F | Ph |
| Ph | Me | iPr | Cl | H |
| Ph | Me | iPr | Cl | Me |
| Ph | Me | iPr | Cl | Et |
| Ph | Me | iPr | Cl | tBu |
| Ph | Me | iPr | Cl | $CF_3$ |
| Ph | Me | iPr | Cl | $COCH_3$ |
| Ph | Me | iPr | Cl | $CH_2OCH_3$ |
| Ph | Me | iPr | Cl | Ph |
| Ph | Me | iPr | Br | H |
| Ph | Me | iPr | Br | Me |
| Ph | Me | iPr | Br | Et |
| Ph | Et | iPr | Br | tBu |
| Ph | Et | iPr | Br | $CF_3$ |
| Ph | Et | iPr | Br | $COCH_3$ |
| Ph | Et | iPr | Br | $CH_2OCH_3$ |

TABLE 1-continued

| | | | | |
|---|---|---|---|---|
| Ph | Et | iPr | Br | Ph |
| Ph | Et | iPr | CF₃ | H |
| Ph | Et | iPr | CF₃ | Me |
| Ph | Et | iPr | CF₃ | Et |
| Ph | Et | iPr | CF₃ | tBu |
| Ph | Et | iPr | CF₃ | CF₃ |
| Ph | H | iPr | CF₃ | COCH₃ |
| Ph | H | iPr | CF₃ | CH₂OCH₃ |
| Ph | H | iPr | CF₃ | Ph |
| Ph | H | iPr | OH | H |
| Ph | H | iPr | OH | Me |
| Ph | H | iPr | OH | Et |
| Ph | H | iPr | OH | tBu |
| Ph | H | iPr | OH | CF₃ |
| Ph | H | iPr | OH | COCH₃ |
| Ph | H | iPr | OH | CH₂OCH₃ |
| Ph | H | iPr | OH | Ph |
| Ph | H | iPr | OMe | H |
| Ph | H | iPr | OMe | Me |
| Ph | H | iPr | OMe | Et |
| Ph | H | iPr | OMe | tBu |
| Ph | H | iPr | OMe | CF₃ |
| Ph | H | iPr | OMe | COCH₃ |
| Ph | H | iPr | OMe | CH₂OCH₃ |
| Ph | H | iPr | OMe | Ph |
| Ph | H | iPr | SMe | H |
| Ph | H | iPr | SMe | Me |
| Ph | H | iPr | SMe | Et |
| Ph | H | iPr | SMe | tBu |
| Ph | H | iPr | SMe | CF₃ |
| Ph | H | iPr | SMe | COCH₃ |
| Ph | H | iPr | SMe | CH₂OCH₃ |
| Ph | H | iPr | SMe | Ph |
| Ph | H | iPr | NO₂ | H |
| Ph | H | iPr | NO₂ | Me |
| Ph | H | iPr | NO₂ | Et |
| Ph | H | iPr | NO₂ | tBu |
| Ph | H | iPr | NO₂ | CF₃ |
| Ph | H | iPr | NO₂ | COCH₃ |
| Ph | H | iPr | NO₂ | CH₂OCH₃ |
| Ph | H | iPr | NO₂ | Ph |
| Ph | H | iPr | CN | H |
| Ph | H | iPr | CN | Me |
| Ph | H | iPr | CN | Et |
| Ph | H | iPr | CN | tBu |
| Ph | H | iPr | CN | CF₃ |
| Ph | H | iPr | CN | COCH₃ |
| Ph | H | iPr | CN | CH₂OCH₃ |
| Ph | H | iPr | CN | Ph |
| Ph | H | iPr | CO₂Me | H |
| Ph | H | iPr | CO₂Me | Me |
| Ph | H | iPr | CO₂Me | Et |
| Ph | H | iPr | CO₂Me | tBu |
| Ph | H | iPr | CO₂Me | CF₃ |
| Ph | H | iPr | CO₂Me | COCH₃ |
| Ph | H | iPr | CO₂Me | CH₂OCH₃ |
| Ph | H | iPr | CO₂Me | Ph |
| Ph | H | iPr | NMe₂ | H |
| Ph | H | iPr | NMe₂ | Me |
| Ph | H | iPr | NMe₂ | Et |
| Ph | H | iPr | NMe₂ | tBu |
| Ph | H | iPr | NMe₂ | CF₃ |
| Ph | H | iPr | NMe₂ | COCH₃ |
| Ph | H | iPr | NMe₂ | CH₂OCH₃ |
| Ph | H | iPr | NMe₂ | Ph |
| Ph | H | tBu | H | H |
| Ph | H | tBu | H | Me |
| Ph | H | tBu | H | Et |
| Ph | H | tBu | H | tBu |
| Ph | H | tBu | H | CF₃ |
| Ph | H | tBu | H | COCH₃ |
| Ph | H | tBu | H | CH₂OCH₃ |
| Ph | H | tBu | H | Ph |
| Ph | H | tBu | Me | H |
| Ph | H | tBu | Me | Me |
| Ph | H | tBu | Me | Et |
| Ph | H | tBu | Me | tBu |
| Ph | H | tBu | Me | CF₃ |
| Ph | H | tBu | Me | COCH₃ |
| Ph | H | tBu | Me | CH₂OCH₃ |
| Ph | H | tBu | Me | Ph |
| Ph | H | tBu | Et | Me |
| Ph | H | tBu | Et | Et |
| Ph | H | tBu | Et | tBu |
| Ph | H | tBu | Et | CF₃ |
| Ph | H | tBu | Et | COCH₃ |
| Ph | H | tBu | Et | CH₂OCH₃ |
| Ph | H | tBu | Et | Ph |
| Ph | H | tBu | iPr | H |
| Ph | H | tBu | iPr | Me |
| Ph | H | tBu | iPr | Et |
| Ph | H | tBu | iPr | tBu |
| Ph | H | tBu | iPr | CF₃ |
| Ph | H | tBu | iPr | COCH₃ |
| Ph | H | tBu | iPr | CH₂OCH₃ |
| Ph | H | tBu | iPr | Ph |
| Ph | H | tBu | tBu | H |
| Ph | H | tBu | tBu | Me |
| Ph | H | tBu | tBu | Et |
| Ph | H | tBu | tBu | tBu |
| Ph | H | tBu | tBu | CF₃ |
| Ph | H | tBu | tBu | COCH₃ |
| Ph | H | tBu | tBu | CH₂OCH₃ |
| Ph | H | tBu | tBu | Ph |
| Ph | H | tBu | Ph | H |
| Ph | H | tBu | Ph | Me |
| Ph | H | tBu | Ph | Et |
| Ph | H | tBu | Ph | tBu |
| Ph | H | tBu | Ph | CF₃ |
| Ph | H | tBu | Ph | COCH₃ |
| Ph | H | tBu | Ph | CH₂OCH₃ |
| Ph | H | tBu | Ph | Ph |
| Ph | H | tBu | F | H |
| Ph | H | tBu | F | Me |
| Ph | H | tBu | F | Et |
| Ph | H | tBu | CF₃ | Me |
| Ph | H | tBu | CF₃ | Et |
| Ph | H | tBu | CF₃ | tBu |
| Ph | H | tBu | CF₃ | CF₃ |
| Ph | H | tBu | CF₃ | COCH₃ |
| Ph | H | tBu | CF₃ | CH₂OCH₃ |
| Ph | H | tBu | CF₃ | Ph |
| Ph | H | tBu | OH | H |
| Ph | H | tBu | OH | Me |
| Ph | H | tBu | OH | Et |
| Ph | H | tBu | OH | tBu |
| Ph | H | tBu | OH | CF₃ |
| Ph | H | tBu | OH | COCH₃ |
| Ph | H | tBu | OH | CH₂OCH₃ |
| Ph | H | tBu | OH | Ph |
| Ph | H | tBu | OMe | H |
| Ph | H | tBu | OMe | Me |
| Ph | H | tBu | OMe | Et |
| Ph | H | tBu | OMe | tBu |
| Ph | H | tBu | OMe | CF₃ |
| Ph | H | tBu | OMe | COCH₃ |
| Ph | H | tBu | OMe | CH₂OCH₃ |
| Ph | H | tBu | F | tBu |
| Ph | H | tBu | F | CF₃ |
| Ph | H | tBu | F | COCH₃ |
| Ph | H | tBu | F | CH₂OCH₃ |
| Ph | H | tBu | F | Ph |
| Ph | H | tBu | Cl | H |
| Ph | H | tBu | Cl | Me |
| Ph | H | tBu | Cl | Et |
| Ph | H | tBu | Cl | tBu |
| Ph | H | tBu | Cl | CF₃ |
| Ph | H | tBu | Cl | COCH₃ |
| Ph | H | tBu | Cl | CH₂OCH₃ |
| Ph | H | tBu | Cl | Ph |
| Ph | H | tBu | Br | H |
| Ph | H | tBu | Br | Me |
| Ph | H | tBu | Br | Et |
| Ph | H | tBu | Br | tBu |
| Ph | H | tBu | Br | CF₃ |
| Ph | H | tBu | Br | COCH₃ |
| Ph | H | tBU | Br | CH₂OCH₃ |

TABLE 1-continued

| | | | | |
|---|---|---|---|---|
| Ph | H | tBu | Br | Ph |
| Ph | H | tBu | CF₃ | H |
| Ph | H | tBu | OMe | Ph |
| Ph | H | tBu | SMe | H |
| Ph | H | tBu | SMe | Me |
| Ph | H | tBu | SMe | Et |
| Ph | H | tBu | SMe | tBu |
| Ph | H | tBu | SMe | CF₃ |
| Ph | H | tBu | SMe | COCH₃ |
| Ph | H | tBu | SMe | CH₂OCH₃ |
| Ph | H | tBu | SMe | Ph |
| Ph | H | tBu | NO₂ | H |
| Ph | H | tBu | NO₂ | Me |
| Ph | H | tBu | NO₂ | Et |
| Ph | H | tBu | NO₂ | tBu |
| Ph | H | tBu | NO₂ | CF₃ |
| Ph | H | tBu | NO₂ | COCH₃ |
| Ph | H | tBu | NO₂ | CH₂OCH₃ |
| Ph | H | tBu | NO₂ | Ph |
| Ph | H | tBu | CN | H |
| Ph | H | tBu | CN | Me |
| Ph | H | tBu | CN | Et |
| Ph | H | tBu | CN | tBu |
| Ph | H | tBu | CN | CF₃ |
| Ph | H | tBu | CN | COCH₃ |
| Ph | H | tBu | CN | CH₂OCH₃ |
| Ph | H | tBu | CN | Ph |
| Ph | H | tBu | CO₂Me | H |
| Ph | H | tBu | CO₂Me | Me |
| Ph | H | tBu | CO₂Me | Et |
| Ph | H | tBu | CO₂Me | tBu |
| Ph | H | tBu | CO₂Me | CF₃ |
| Ph | H | tBu | CO₂Me | COCH₃ |
| Ph | H | tBu | CO₂Me | CH₂OCH₃ |
| Ph | H | tBu | CO₂Me | Ph |
| Ph | H | tBu | NMe₂ | H |
| Ph | H | tBu | NMe₂ | Me |
| Ph | H | tBu | NMe₂ | Et |
| Ph | H | tBu | NMe₂ | tBu |
| Ph | H | tBu | NMe₂ | CF₃ |
| Ph | H | tBu | NMe₂ | COCH₃ |
| Ph | H | tBu | NMe₂ | CH₂OCH₃ |
| Ph | H | tBu | NMe₂ | Ph |
| Ph | H | CF₃ | H | H |
| Ph | H | CF₃ | H | Me |
| Ph | H | CF₃ | H | Et |
| Ph | H | CF₃ | H | tBu |
| Ph | H | CF₃ | H | CF₃ |
| Ph | H | CF₃ | H | COCH₃ |
| Ph | H | CF₃ | H | CH₂OCH₃ |
| Ph | H | CF₃ | H | Ph |
| Ph | H | CF₃ | Me | H |
| Ph | H | CF₃ | Me | Me |
| Ph | H | CF₃ | Me | Et |
| Ph | H | CF₃ | Me | tBu |
| Ph | H | CF₃ | Me | CF₃ |
| Ph | H | CF₃ | Me | COCH₃ |
| Ph | H | CF₃ | Me | CH₂OCH₃ |
| Ph | H | CF₃ | Me | Ph |
| Ph | H | CF₃ | Et | H |
| Ph | H | CF₃ | Et | Me |
| Ph | H | CF₃ | Et | Et |
| Ph | H | CF₃ | Et | tBu |
| Ph | H | CF₃ | Et | CF₃ |
| Ph | H | CF₃ | Et | COCH₃ |
| Ph | H | CF₃ | Et | CH₂OCH₃ |
| Ph | H | CF₃ | Et | Ph |
| Ph | H | CF₃ | iPr | H |
| Ph | H | CF₃ | iPr | Me |
| Ph | H | CF₃ | iPr | Et |
| Ph | H | CF₃ | iPr | tBu |
| Ph | H | CF₃ | iPr | CF₃ |
| Ph | H | CF₃ | iPr | COCH₃ |
| Ph | H | CF₃ | iPr | CH₂OCH₃ |
| Ph | H | CF₃ | iPr | Ph |
| Ph | H | CF₃ | tBu | H |
| Ph | H | CF₃ | tBu | Me |
| Ph | H | CF₃ | tBu | Et |
| Ph | H | CF₃ | tBu | tBu |
| Ph | H | CF₃ | tBu | CF₃ |
| Ph | H | CF₃ | tBu | COCH₃ |
| Ph | H | CF₃ | tBu | CH₂OCH₃ |
| Ph | H | CF₃ | tBu | Ph |
| Ph | H | CF₃ | Ph | H |
| Ph | H | CF₃ | Ph | Me |
| Ph | H | CF₃ | Ph | Et |
| Ph | H | CF₃ | Ph | tBu |
| Ph | H | CF₃ | Ph | CF₃ |
| Ph | H | CF₃ | Ph | COCH₃ |
| Ph | H | CF₃ | Ph | CH₂OCH₃ |
| Ph | H | CF₃ | Ph | Ph |
| Ph | H | CF₃ | F | H |
| Ph | H | CF₃ | F | Me |
| Ph | H | CF₃ | F | Et |
| Ph | H | CF₃ | F | tBu |
| Ph | H | CF₃ | F | CF₃ |
| Ph | H | CF₃ | F | COCH₃ |
| Ph | H | CF₃ | F | CH₂OCH₃ |
| Ph | H | CF₃ | F | Ph |
| Ph | H | CF₃ | Cl | H |
| Ph | H | CF₃ | Cl | Me |
| Ph | H | CF₃ | Cl | Et |
| Ph | H | CF₃ | Cl | tBu |
| Ph | H | CF₃ | Cl | CF₃ |
| Ph | H | CF₃ | Cl | COCH₃ |
| Ph | H | CF₃ | Cl | CH₂OCH₃ |
| Ph | H | CF₃ | Cl | Ph |
| Ph | H | CF₃ | Br | H |
| Ph | H | CF₃ | Br | Me |
| Ph | H | CF₃ | Br | Et |
| Ph | H | CF₃ | Br | tBu |
| Ph | H | CF₃ | Br | CF₃ |
| Ph | H | CF₃ | Br | COCH₃ |
| Ph | H | CF₃ | Br | CH₂OCH₃ |
| Ph | H | CF₃ | Br | Ph |
| Ph | H | CF₃ | CF₃ | H |
| Ph | H | CF₃ | CF₃ | Me |
| Ph | H | CF₃ | CF₃ | Et |
| Ph | H | CF₃ | CF₃ | tBu |
| Ph | H | CF₃ | CF₃ | CF₃ |
| Ph | H | CF₃ | CF₃ | COCH₃ |
| Ph | H | CF₃ | CF₃ | CH₂OCH₃ |
| Ph | H | CF₃ | CF₃ | Ph |
| Ph | H | CF₃ | OH | H |
| Ph | H | CF₃ | OH | Me |
| Ph | H | CF₃ | OH | Et |
| Ph | H | CF₃ | OH | tBu |
| Ph | H | CF₃ | OH | CF₃ |
| Ph | H | CF₃ | OH | COCH₃ |
| Ph | H | CF₃ | OH | CH₂OCH₃ |
| Ph | H | CF₃ | OH | Ph |
| Ph | H | CF₃ | OMe | H |
| Ph | H | CF₃ | OMe | Me |
| Ph | H | CF₃ | OMe | Et |
| Ph | H | CF₃ | OMe | tBu |
| Ph | H | CF₃ | OMe | CF₃ |
| Ph | H | CF₃ | OMe | COCH₃ |
| Ph | H | CF₃ | OMe | CH₂OCH₃ |
| Ph | H | CF₃ | OMe | Ph |
| Ph | H | CF₃ | SMe | H |
| Ph | H | CF₃ | SMe | Me |
| Ph | H | CF₃ | SMe | Et |
| Ph | H | CF₃ | SMe | tBu |
| Ph | H | CF₃ | SMe | CF₃ |
| Ph | H | CF₃ | SMe | COCH₃ |
| Ph | H | CF₃ | SMe | CH₂OCH₃ |
| Ph | H | CF₃ | SMe | Ph |
| Ph | H | CF₃ | NO₂ | H |
| Ph | H | CF₃ | NO₂ | Me |
| Ph | H | CF₃ | NO₂ | Et |
| Ph | H | CF₃ | NO₂ | tBu |
| Ph | H | CF₃ | NO₂ | CF₃ |
| Ph | H | CF₃ | NO₂ | COCH₃ |
| Ph | H | CF₃ | NO₂ | CH₂OCH₃ |
| Ph | H | CF₃ | NO₂ | Ph |
| Ph | H | CF₃ | CN | H |
| Ph | H | CF₃ | CN | Me |
| Ph | H | CF₃ | CN | Et |

TABLE 1-continued

| | | | | |
|---|---|---|---|---|
| Ph | H | CF₃ | CN | tBu |
| Ph | H | CF₃ | CN | CF₃ |
| Ph | H | CF₃ | CN | COCH₃ |
| Ph | H | CF₃ | CN | CH₂OCH₃ |
| Ph | H | CF₃ | CN | Ph |
| Ph | H | CF₃ | CO₂Me | H |
| Ph | H | CF₃ | CO₂Me | Me |
| Ph | H | CF₃ | CO₂Me | Et |
| Ph | H | CF₃ | CO₂Me | tBu |
| Ph | H | CF₃ | CO₂Me | CF₃ |
| Ph | H | CF₃ | CO₂Me | COCH₃ |
| Ph | H | CF₃ | CO₂Me | CH₂OCH₃ |
| Ph | H | CF₃ | CO₂Me | Ph |
| Ph | H | CF₃ | NMe₂ | H |
| Ph | H | CF₃ | NMe₂ | Me |
| Ph | H | CF₃ | NMe₂ | Et |
| Ph | H | CF₃ | NMe₂ | tBu |
| Ph | H | CF₃ | NMe₂ | CF₃ |
| Ph | H | CF₃ | NMe₂ | COCH₃ |
| Ph | H | CF₃ | NMe₂ | CH₂OCH₃ |
| Ph | H | CF₃ | NMe₂ | Ph |
| Ph | H | Cl | H | H |
| Ph | H | Cl | H | Me |
| Ph | H | Cl | H | Et |
| Ph | H | Cl | H | tBu |
| Ph | H | Cl | H | CF₃ |
| Ph | H | Cl | H | COCH₃ |
| Ph | H | Cl | H | CH₂OCH₃ |
| Ph | H | Cl | H | Ph |
| Ph | H | Cl | Me | H |
| Ph | H | Cl | Me | Me |
| Ph | H | Cl | Me | Et |
| Ph | H | Cl | Me | tBu |
| Ph | H | Cl | Me | CF₃ |
| Ph | H | Cl | Me | COCH₃ |
| Ph | H | Cl | Me | CH₂OCH₃ |
| Ph | H | Cl | Me | Ph |
| Ph | H | Cl | Et | H |
| Ph | H | Cl | Et | Me |
| Ph | H | Cl | Et | Et |
| Ph | H | Cl | Et | tBu |
| Ph | H | Cl | Et | CF₃ |
| Ph | H | Cl | Et | COCH₃ |
| Ph | H | Cl | Et | CH₂OCH₃ |
| Ph | H | Cl | Et | Ph |
| Ph | H | Cl | iPr | H |
| Ph | H | Cl | iPr | Me |
| Ph | H | Cl | iPr | Et |
| Ph | H | Cl | iPr | tBu |
| Ph | H | Cl | iPr | CF₃ |
| Ph | H | Cl | iPr | COCH₃ |
| Ph | H | Cl | iPr | CH₂OCH₃ |
| Ph | H | Cl | iPr | Ph |
| Ph | H | Cl | tBu | H |
| Ph | H | Cl | tBu | Me |
| Ph | H | Cl | tBu | Et |
| Ph | H | Cl | tBu | tBu |
| Ph | H | Cl | tBu | CF₃ |
| Ph | H | Cl | tBu | COCH₃ |
| Ph | H | Cl | tBu | CH₂OCH₃ |
| Ph | H | Cl | tBu | Ph |
| Ph | H | Cl | Ph | H |
| Ph | H | Cl | Ph | Me |
| Ph | H | Cl | Ph | Et |
| Ph | H | Cl | Ph | tBu |
| Ph | H | Cl | Ph | CF₃ |
| Ph | H | Cl | Ph | COCH₃ |
| Ph | H | Cl | Ph | CH₂OCH₃ |
| Ph | H | Cl | Ph | Ph |
| Ph | H | Cl | F | H |
| Ph | H | Cl | F | Me |
| Ph | H | Cl | F | Et |
| Ph | H | Cl | F | tBu |
| Ph | H | Cl | F | CF₃ |
| Ph | H | Cl | F | COCH₃ |
| Ph | H | Cl | F | CH₂OCH₃ |
| Ph | H | Cl | F | Ph |
| Ph | H | Cl | Cl | H |
| Ph | H | Cl | Cl | Me |
| Ph | H | Cl | Cl | Et |
| Ph | H | Cl | Cl | tBu |
| Ph | H | Cl | Cl | CF₃ |
| Ph | H | Cl | Cl | COCH₃ |
| Ph | H | Cl | Cl | CH₂OCH₃ |
| Ph | H | Cl | Cl | Ph |
| Ph | H | Cl | Br | H |
| Ph | H | Cl | Br | Me |
| Ph | H | Cl | Br | Et |
| Ph | H | Cl | Br | tBu |
| Ph | H | Cl | Br | CF₃ |
| Ph | H | Cl | Br | COCH₃ |
| Ph | H | Cl | Br | CH₂OCH₃ |
| Ph | H | Cl | Br | Ph |
| 2,6-F₂—Ph | H | Cl | CF₃ | H |
| 2,6-F₂—Ph | H | Cl | CF₃ | Me |
| 2,6-F₂—Ph | H | Cl | CF₃ | Et |
| 2,6-F₂—Ph | H | Cl | CF₃ | tBu |
| 2,6-F₂—Ph | H | Cl | CF₃ | CF₃ |
| 2,6-F₂—Ph | H | Cl | CF₃ | COCH₃ |
| 2,6-F₂—Ph | H | Cl | CF₃ | CH₂OCH₃ |
| 2,6-F₂—Ph | H | Cl | CF₃ | Ph |
| 2,6-F₂—Ph | H | Cl | OH | H |
| 2,6-F₂—Ph | H | Cl | OH | Me |
| 2,6-F₂—Ph | H | Cl | OH | Et |
| 2,6-F₂—Ph | H | Cl | OH | tBu |
| 2,6-F₂—Ph | H | Cl | OH | CF₃ |
| 2,6-F₂—Ph | H | Cl | OH | COCH₃ |
| 2,6-F₂—Ph | H | Cl | OH | CH₂OCH₃ |
| 2,6-F₂—Ph | H | CF₃ | OH | Ph |
| 2,6-F₂—Ph | H | CF₃ | OMe | H |
| 2,6-F₂—Ph | H | CF₃ | OMe | Me |
| 2,6-F₂—Ph | H | CF₃ | OMe | Et |
| 2,6-F₂—Ph | H | CF₃ | OMe | tBu |
| 2,6-F₂—Ph | H | CF₃ | OMe | CF₃ |
| 2,6-F₂—Ph | H | CF₃ | OMe | COCH₃ |
| 2,6-F₂—Ph | H | CF₃ | OMe | CH₂OCH₃ |
| 2,6-F₂—Ph | H | CF₃ | OMe | Ph |
| 2,6-F₂—Ph | H | CF₃ | SMe | H |
| 2,6-F₂—Ph | H | CF₃ | SMe | Me |
| 2,6-F₂—Ph | H | CF₃ | SMe | Et |
| 2,6-F₂—Ph | H | CF₃ | SMe | tBu |
| 2,6-F₂—Ph | H | CF₃ | SMe | CF₃ |
| 2,6-F₂—Ph | H | CF₃ | SMe | COCH₃ |
| 2,6-F₂—Ph | H | CF₃ | SMe | CH₂OCH₃ |
| 2,6-F₂—Ph | H | CF₃ | SMe | Ph |
| 2,6-F₂—Ph | H | CF₃ | NO₂ | H |
| 2,6-F₂—Ph | H | CF₃ | NO₂ | Me |
| 2,6-F₂—Ph | H | CF₃ | NO₂ | Et |
| 2,6-F₂—Ph | H | CF₃ | NO₂ | tBu |
| 2,6-F₂—Ph | H | CF₃ | NO₂ | CF₃ |
| 2,6-F₂—Ph | H | Cl | NO₂ | COCH₃ |
| 2,6-F₂—Ph | H | Cl | NO₂ | CH₂OCH₃ |
| 2,6-F₂—Ph | H | Cl | NO₂ | Ph |
| 2,6-F₂—Ph | H | Cl | CN | H |
| 2,6-F₂—Ph | H | Cl | CN | Me |
| 2,6-F₂—Ph | H | Cl | CN | Et |
| 2,6-F₂—Ph | H | Cl | CN | tBu |
| 2,6-F₂—Ph | H | Cl | CN | CF₃ |
| 2,6-F₂—Ph | H | Cl | CN | COCH₃ |
| 2,6-F₂—Ph | H | Cl | CN | CH₂OCH₃ |
| 2,6-F₂—Ph | H | Cl | CN | Ph |
| 2,6-F₂—Ph | H | Cl | CO₂Me | H |
| 2,6-F₂—Ph | H | Cl | CO₂Me | Me |
| 2,6-F₂—Ph | H | Cl | CO₂Me | Et |
| 2,6-F₂—Ph | H | Cl | CO₂Me | tBu |
| 2,6-F₂—Ph | H | Cl | CO₂Me | CF₃ |
| 2,6-F₂—Ph | H | Cl | CO₂Me | COCH₃ |
| 2,6-F₂—Ph | H | Cl | CO₂Me | CH₂OCH₃ |
| 2,6-F₂—Ph | H | Cl | CO₂Me | Ph |
| 2,6-F₂—Ph | H | Cl | NMe₂ | H |
| 2,6-F₂—Ph | H | Cl | NMe₂ | Me |
| 2,6-F₂—Ph | H | Cl | NMe₂ | Et |
| 2,6-F₂—Ph | H | Cl | NMe₂ | tBu |
| 2,6-F₂—Ph | H | Cl | NMe₂ | CF₃ |
| 2,6-F₂—Ph | H | Cl | NMe₂ | COCH₃ |
| 2,6-F₂—Ph | H | Cl | NMe₂ | CH₂OCH₃ |
| 2,6-F₂—Ph | H | Cl | NMe₂ | Ph |
| 2,6-F₂—Ph | H | Cl | nPr | Me |

TABLE 1-continued

| | | | | |
|---|---|---|---|---|
| 2,6-F₂—Ph | H | Cl | nBu | Me |
| 2,6-F₂—Ph | H | Cl | iBu | Me |
| 2,6-F₂—Ph | H | Cl | sBu | Me |
| 2,6-F₂—Ph | H | Cl | cPr | Me |
| 2,6-F₂—Ph | H | Cl | I | Me |
| 2,6-F₂—Ph | H | Cl | CHF₂ | Me |
| 2,6-F₂—Ph | H | Cl | CH₂F | Me |
| 2,6-F₂—Ph | H | Cl | OEt | Me |
| 2,6-F₂—Ph | H | Cl | OPr | Me |
| 2,6-F₂—Ph | H | Cl | O-tBu | Me |
| 2,6-F₂—Ph | H | Cl | OPh | Me |
| 2,6-F₂—Ph | H | Cl | SEt | Me |
| 2,6-F₂—Ph | H | Cl | S-tBu | Me |
| 2,6-F₂—Ph | H | Cl | SOMe | Me |
| 2,6-F₂—Ph | H | Cl | SO₂Me | Me |
| 2,6-F₂—Ph | H | Cl | CH₂Ph | Me |
| 2,3-Cl₂—Ph | Me | Me | Cl | Me |
| 2,3-Cl₂—Ph | Me | CF₃ | Cl | Me |
| 2,3-Cl₂—Ph | Me | Cl | Cl | Me |
| 2,4-Cl₂—Ph | Me | Me | Cl | Me |
| 2,4-Cl₂—Ph | Me | CF₃ | Cl | Me |
| 2,4-Cl₂—Ph | Me | Cl | Cl | Me |
| 2,5-Cl₂—Ph | Me | Me | Cl | Me |
| 2,5-Cl₂—Ph | Me | CF₃ | Cl | Me |
| 2,5-Cl₂—Ph | Me | Cl | Cl | Me |
| 2,6-Cl₂—Ph | Me | Me | Cl | Me |
| 2,6-Cl₂—Ph | Me | CF₃ | Cl | Me |
| 2,4-F₂—Ph | Me | CF₃ | Cl | Me |
| 2,4-F₂—Ph | Me | Cl | Cl | Me |
| 2,5-F₂—Ph | Me | Me | Cl | Me |
| 2,5-F₂—Ph | Me | CF₃ | Cl | Me |
| 2,5-F₂—Ph | Me | Cl | Cl | Me |
| 2,6-F₂—Ph | Me | Me | Cl | Me |
| 2,6-F₂—Ph | Me | CF₃ | Cl | Me |
| 2,6-F₂—Ph | Me | Cl | Cl | Me |
| 2,6-F₂—Ph | Et | CF₃ | Cl | Me |
| 2,6-F₂—Ph | Et | Cl | Cl | Me |
| 3,4-F₂—Ph | Me | Cl | Cl | Me |
| 2-Cl—Ph | Me | Ph | Cl | Me |
| 2-Cl—Ph | Me | F | Cl | Me |
| 2-Cl—Ph | Me | Br | Cl | Me |
| 3-Cl—Ph | Me | I | Cl | Me |
| 3-Cl—Ph | Me | CHF₂ | Cl | Me |
| 3-Cl—Ph | Me | CH₂F | Cl | Me |
| 4-Cl—Ph | Me | CN | Cl | Me |
| 4-Cl—Ph | Me | NO₂ | Cl | Me |
| 4-Cl—Ph | Me | NMe₂ | Cl | Me |
| 2-F—Ph | Me | NEt₂ | Cl | Me |
| 2-F—Ph | Me | Cl | Cl | Me |
| 2-Cl—Ph | H | Me | Cl | Me |
| 2-Cl—Ph | H | CF₃ | Cl | Me |
| 2-Cl—Ph | H | Cl | Cl | Me |
| 3-Cl—Ph | H | Me | Cl | Me |
| 3-Cl—Ph | H | CF₃ | Cl | Me |
| 3-Cl—Ph | H | Cl | Cl | Me |
| 4-Cl—Ph | H | Me | Cl | Me |
| 4-Cl—Ph | H | CF₃ | Cl | Me |
| 4-Cl—Ph | H | Cl | Cl | Me |
| 2-F—Ph | H | Me | Cl | Me |
| 2-F—Ph | H | CF₃ | Cl | Me |
| 2-F—Ph | H | Cl | Cl | Me |
| 3-F—Ph | H | Me | Cl | Me |
| 3-F—Ph | H | CF₃ | Cl | Me |
| 3-F—Ph | H | Cl | Cl | Me |
| 4-F—Ph | H | Me | Cl | Me |
| 4-F—Ph | H | CF₃ | Cl | Me |
| 4-F—Ph | H | Cl | Cl | Me |
| 2-Br—Ph | H | Me | Cl | Me |
| 2-Br—Ph | H | CF₃ | Cl | Me |
| 2-Br—Ph | H | Cl | Cl | Me |
| 3-Br—Ph | H | Me | Cl | Me |
| 3-Br—Ph | H | CF₃ | Cl | Me |
| 3-Br—Ph | H | Cl | Cl | Me |
| 4-Br—Ph | H | Me | Cl | Me |
| 4-Br—Ph | H | CF₃ | Cl | Me |
| 4-Br—Ph | H | Cl | Cl | Me |
| 2-Me—Ph | H | Me | Cl | Me |
| 2-Me—Ph | H | CF₃ | Cl | Me |
| 2-Me—Ph | H | Cl | Cl | Me |
| 3-Me—Ph | H | Me | Cl | Me |
| 3-Me—Ph | H | CF₃ | Cl | Me |
| 3-Me—Ph | H | Cl | Cl | Me |
| 4-Me—Ph | H | Me | Cl | Me |
| 4-Me—Ph | H | CF₃ | Cl | Me |
| 4-Me—Ph | H | Cl | Cl | Me |
| 2-CF₃—Ph | H | Me | Cl | Me |
| 2-CF₃—Ph | H | CF₃ | Cl | Me |
| 2-CF₃—Ph | H | Cl | Cl | Me |
| 3-CF₃—Ph | H | Me | Cl | Me |
| 3-CF₃—Ph | H | CF₃ | Cl | Me |
| 3-CF₃—Ph | H | Cl | Cl | Me |
| 4-CF₃—Ph | H | Me | Cl | Me |
| 4-CF₃—Ph | H | CF₃ | Cl | Me |
| 4-CF₃—Ph | H | Cl | Cl | Me |
| 3-tBu—Ph | H | Me | Cl | Me |
| 3-tBu—Ph | H | CF₃ | Cl | Me |
| 3-tBu—Ph | H | Cl | Cl | Me |
| 4-tBu—Ph | H | Me | Cl | Me |
| 4-tBu—Ph | H | CF₃ | Cl | Me |
| 4-tBu—Ph | H | Cl | Cl | Me |
| 2-MeO—Ph | H | Me | Cl | Me |
| 2-MeO—Ph | H | CF₃ | Cl | Me |
| 2-MeO—Ph | H | Cl | Cl | Me |
| 3-MeO—Ph | H | Me | Cl | Me |
| 3-MeO—Ph | H | CF₃ | Cl | Me |
| 3-MeO—Ph | H | Cl | Cl | Me |
| 4-MeO—Ph | H | Me | Cl | Me |
| 4-MeO—Ph | H | CF₃ | Cl | Me |
| 4-MeO—Ph | H | Cl | Cl | Me |
| 2-CN—Ph | H | Cl | Cl | Me |
| 3-CN—Ph | H | Cl | Cl | Me |
| 4-CN—Ph | H | Cl | Cl | Me |
| 2-NO₂—Ph | H | Cl | Cl | Me |
| 3-NO₂—Ph | H | Cl | Cl | Me |
| 4-NO₂—Ph | H | Cl | Cl | Me |
| 2,3-Cl₂—Ph | H | Me | Cl | Me |
| 2,3-Cl₂—Ph | H | CF₃ | Cl | Me |
| 2,3-Cl₂—Ph | H | Cl | Cl | Me |
| 2,4-Cl₂—Ph | H | Me | Cl | Me |
| 2,4-Cl₂—Ph | H | CF₃ | Cl | Me |
| 2,4-Cl₂—Ph | H | Cl | Cl | Me |
| 2,5-Cl₂—Ph | H | Me | Cl | Me |
| 2,5-Cl₂—Ph | H | CF₃ | Cl | Me |
| 2,5-Cl₂—Ph | H | Cl | Cl | Me |
| 2,6-Cl₂—Ph | H | Me | Cl | Me |
| 2,6-Cl₂—Ph | H | CF₃ | Cl | Me |
| 2,6-Cl₂—Ph | H | Cl | Cl | Me |
| 3,4-Cl₂—Ph | H | Me | Cl | Me |
| 3,4-Cl₂—Ph | H | CF₃ | Cl | Me |
| 3,4-Cl₂—Ph | H | Cl | Cl | Me |
| 3,5-Cl₂—Ph | H | Me | Cl | Me |
| 3,5-Cl₂—Ph | H | CF₃ | Cl | Me |
| 3,5-Cl₂—Ph | H | Cl | Cl | Me |
| 2,3-F₂—Ph | H | Me | Cl | Me |
| 2,3-F₂—Ph | H | CF₃ | Cl | Me |
| 2,3-F₂—Ph | H | Cl | Cl | Me |
| 2,4-F₂—Ph | H | Me | Cl | Me |
| 2,4-F₂—Ph | H | CF₃ | Cl | Me |
| 2,4-F₂—Ph | H | Cl | Cl | Me |
| 2,5-F₂—Ph | H | Me | Cl | Me |
| 2,5-F₂—Ph | H | CF₃ | Cl | Me |
| 2,5-F₂—Ph | H | Cl | Cl | Me |
| 2,6-F₂—Ph | H | Me | Cl | Me |
| 2,6-F₂—Ph | H | CF₃ | Cl | Me |
| 2,6-F₂—Ph | H | Cl | Cl | Me |
| 3,4-F₂—Ph | H | Me | Cl | Me |
| 3,4-F₂—Ph | H | CF₃ | Cl | Me |
| 3,4-F₂—Ph | H | Cl | Cl | Me |
| 1-naphthyl | H | Me | Cl | Me |
| 1-naphthyl | H | CF₃ | Cl | Me |
| 1-naphthyl | H | Cl | Cl | Me |
| 2-pyridinyl | H | Me | Cl | Me |
| 2-pyridinyl | H | CF₃ | Cl | Me |
| 2-pyridinyl | H | Cl | Cl | Me |
| cHex | Me | Me | Cl | Me |
| cHex | H | CF₃ | Cl | Me |
| cHex | H | Cl | Cl | Me |
| cHex | H | Me | Cl | Me |

TABLE 1-continued

| | | | | |
|---|---|---|---|---|
| cHex | Me | CF₃ | Cl | Me |
| Et | H | Cl | Cl | Me |
| cHex | H | Me | Cl | Me |
| nPr | H | CF₃ | Cl | Me |
| cPen | H | Cl | Cl | Me |
| cPen | H | Me | Cl | Me |
| cPen | H | CF₃ | Cl | Me |
| 1-Me-cHex | H | Cl | Cl | Me |
| 1-Me-cHex | H | Me | Cl | Me |
| 1-Me-cHex | H | CF₃ | Cl | Me |
| cPr | H | Cl | Cl | Me |
| 1-Me-cPr | H | Me | Cl | Me |
| 1-Me-cPr | H | CF₃ | Cl | Me |
| 1-Me-cPr | H | Cl | Cl | Me |
| 1-adamantyl | H | Me | Cl | Me |
| 1-adamantyl | H | CF₃ | Cl | Me |
| 1-adamantyl | H | Cl | Cl | Me |
| iBu | H | Me | Cl | Me |
| iBu | H | CF₃ | Cl | Me |
| iBu | H | Cl | Cl | Me |
| sBu | H | Me | Cl | Me |
| sBu | H | CF₃ | Cl | Me |
| sBu | H | Cl | Cl | Me |
| 2-pyridinyl | Me | Me | Cl | Me |
| 2-pyridinyl | Me | CF₃ | Cl | Me |
| 2-pyridinyl | Me | Cl | Cl | Me |
| 1-naphthyl | Me | Me | Cl | Me |
| 1-naphthyl | Me | CF₃ | Cl | Me |
| 1-naphthyl | Me | Cl | Cl | Me |
| 2-NO₂—Ph | H | CF₃ | H | Me |
| 2-CN—Ph | H | H | CF₃ | Me |
| 1-Me-cPr | H | CF₃ | H | Me |
| 1-Me-cPr | H | H | CF₃ | Me |
| cHex | H | H | CF₃ | Me |
| cHex | H | CF₃ | H | Me |
| 1-Me-cHex | H | CF₃ | H | Me |
| 1-Me-cHex | H | H | CF₃ | Me |
| 1-naphthyl | H | CF₃ | H | Me |
| 1-naphthyl | H | H | CF₃ | Me |
| 2,6-F₂—Ph | H | CF₃ | H | Me |
| 2,6-F₂—Ph | H | H | CF₃ | Me |
| 2-F—Ph | H | CF₃ | H | Me |
| 2-F—Ph | H | H | CF₃ | Me |
| 2-Cl—Ph | H | CF₃ | H | Me |
| 2-Cl—Ph | H | H | CF₃ | Me |
| tBu | H | H | Et | CH₂OCH₃ |
| tBu | H | H | Et | Ph |
| tBu | H | H | iPr | H |
| tBu | H | H | iPr | Me |
| tBu | H | H | iPr | Et |
| tBu | H | H | iPr | tBu |
| tBu | H | H | iPr | CF₃ |
| tBu | H | H | iPr | COCH₃ |
| tBu | H | H | iPr | CH₂OCH₃ |
| tBu | H | H | iPr | Ph |
| tBu | H | H | tBu | H |
| tBu | H | H | tBu | Me |
| tBu | H | H | tBu | Et |
| tBu | H | H | tBu | tBu |
| tBu | H | H | tBu | CF₃ |
| tBu | H | H | tBu | COCH₃ |
| tBu | H | H | tBu | CH₂OCH₃ |
| tBu | H | H | tBu | Ph |
| tBu | H | H | Ph | H |
| tBu | H | H | Ph | Me |
| tBu | H | H | Ph | Et |
| tBu | H | H | Ph | tBu |
| tBu | H | H | Ph | CF₃ |
| tBu | H | H | Ph | COCH₃ |
| tBu | H | H | Ph | CH₂OCH₃ |
| tBu | H | H | Ph | Ph |
| tBu | H | H | F | H |
| tBu | H | H | F | Me |
| tBu | H | H | F | Et |
| tBu | H | H | F | tBu |
| tBu | H | H | F | CF₃ |
| tBu | H | H | F | COCH₃ |
| tBu | H | H | F | CH₂OCH₃ |
| tBu | H | H | F | Ph |
| tBu | H | H | Cl | H |
| tBu | H | H | Cl | Me |
| tBu | H | H | Cl | Et |
| tBu | H | H | Cl | tBu |
| tBu | H | H | Cl | CF₃ |
| tBu | H | H | Cl | COCH₃ |
| tBu | H | H | Cl | CH₂OCH₃ |
| tBu | H | H | Cl | Ph |
| tBu | H | H | Br | H |
| tBu | H | H | Br | Me |
| tBu | H | H | Br | Et |
| tBu | H | H | Br | tBu |
| tBu | H | H | Br | CF₃ |
| tBu | H | H | Br | COCH₃ |
| tBu | H | H | Br | CH₂OCH₃ |
| tBu | H | H | Br | Ph |
| tBu | H | H | CF₃ | H |
| tBu | H | H | CF₃ | Me |
| tBu | H | H | CF₃ | Et |
| tBu | H | H | CF₃ | tBu |
| tBu | H | H | CF₃ | CF₃ |
| tBu | H | H | CF₃ | COCH₃ |
| tBu | H | H | CF₃ | CH₂OCH₃ |
| tBu | H | H | CF₃ | Ph |
| tBu | H | H | OH | H |
| tBu | H | H | OH | Me |
| tBu | H | H | OH | Et |
| tBu | H | H | OH | tBu |
| tBu | H | H | OH | CF₃ |
| tBu | H | H | OH | COCH₃ |
| tBu | H | H | OH | CH₂OCH₃ |
| tBu | H | H | OH | Ph |
| tBu | H | H | OMe | H |
| tBu | H | H | OMe | Me |
| tBu | H | H | OMe | Et |
| tBu | H | H | OMe | tBu |
| tBu | H | H | OMe | CF₃ |
| tBu | H | H | OMe | COCH₃ |
| tBu | H | H | OMe | CH₂OCH₃ |
| tBu | H | H | OMe | Ph |
| tBu | H | H | SMe | H |
| tBu | H | H | SMe | Me |
| tBu | H | H | SMe | Et |
| tBu | H | H | SMe | tBu |
| tBu | H | H | SMe | CF₃ |
| tBu | H | H | SMe | COCH₃ |
| tBu | H | H | SMe | CH₂OCH₃ |
| tBu | H | H | SMe | Ph |
| tBu | H | H | NO₂ | H |
| tBu | H | H | NO₂ | Me |
| tBu | H | H | NO₂ | Et |
| tBu | H | H | NO₂ | tBu |
| tBu | H | H | NO₂ | CF₃ |
| tBu | H | H | NO₂ | COCH₃ |
| tBu | H | H | NO₂ | CH₂OCH₃ |
| tBu | H | H | NO₂ | Ph |
| tBu | H | H | CN | H |
| tBu | H | H | CN | Me |
| tBu | H | H | CN | Et |
| tBu | H | H | CN | tBu |
| tBu | H | H | CN | CF₃ |
| tBu | H | H | CN | COCH₃ |
| tBu | H | H | CN | CH₂OCH₃ |
| tBu | H | H | CN | Ph |
| tBu | H | H | CO₂Me | H |
| tBu | H | H | CO₂Me | Me |
| tBu | H | H | CO₂Me | Et |
| tBu | H | H | CO₂Me | tBu |
| tBu | H | H | CO₂Me | CF₃ |
| tBu | H | H | CO₂Me | COCH₃ |
| tBu | H | H | CO₂Me | CH₂OCH₃ |
| tBu | H | H | CO₂Me | Ph |
| tBu | H | H | NMe₂ | H |
| tBu | H | H | NMe₂ | Me |
| tBu | H | H | NMe₂ | Et |
| tBu | H | H | NMe₂ | tBu |
| tBu | H | H | NMe₂ | CF₃ |
| tBu | H | H | NMe₂ | COCH₃ |
| tBu | H | H | NMe₂ | CH₂OCH₃ |

TABLE 1-continued

| | | | | |
|---|---|---|---|---|
| tBu | H | H | NMe₂ | Ph |
| tBu | H | Me | H | H |
| tBu | H | Me | H | Me |
| tBu | H | Me | H | Et |
| tBu | H | Me | H | tBu |
| tBu | H | Me | H | CF₃ |
| tBu | H | Me | H | COCH₃ |
| tBu | H | Me | H | CH₂OCH₃ |
| tBu | H | Me | H | Ph |
| tBu | H | Me | Me | H |
| tBu | H | Me | Me | Me |
| tBu | H | Me | Me | Et |
| tBu | H | Me | Me | tBu |
| tBu | H | Me | Me | CF₃ |
| tBu | H | Me | Me | COCH₃ |
| tBu | H | Me | Me | CH₂OCH₃ |
| tBu | H | Me | Me | Ph |
| tBu | H | Me | Et | H |
| tBu | H | Me | Et | Me |
| tBu | H | Me | Et | Et |
| tBu | H | Me | Et | tBu |
| tBu | H | Me | Et | CF₃ |
| tBu | H | Me | Et | COCH₃ |
| tBu | H | Me | Et | CH₂OCH₃ |
| tBu | H | Me | Et | Ph |
| tBu | H | Me | iPr | H |
| tBu | H | Me | iPr | Me |
| tBu | H | Me | iPr | Et |
| tBu | H | Me | iPr | tBu |
| tBu | H | Me | iPr | CF₃ |
| tBu | Et | Me | iPr | COCH₃ |
| tBu | Et | Me | iPr | CH₂OCH₃ |
| tBu | Et | Me | iPr | Ph |
| tBu | Et | Me | tBu | H |
| tBu | Et | Me | tBu | Me |
| tBu | Et | Me | tBu | Et |
| tBu | Et | Me | tBu | tBu |
| tBu | Et | Me | tBu | CF₃ |
| tBu | Et | Me | tBu | COCH₃ |
| tBu | Et | Me | tBu | CH₂OCH₃ |
| tBu | Et | Me | tBu | Ph |
| tBu | Et | Me | Ph | H |
| tBu | Et | Me | Ph | Me |
| tBu | Et | Me | Ph | Et |
| tBu | Et | Me | Ph | tBu |
| tBu | Et | Me | Ph | CF₃ |
| tBu | Et | Me | Ph | COCH₃ |
| tBu | Et | Me | Ph | CH₂OCH₃ |
| tBu | Et | Me | Ph | Ph |
| tBu | Et | Me | F | H |
| tBu | Et | Me | F | Me |
| tBu | Et | Me | F | Et |
| tBu | H | Me | F | tBu |
| tBu | H | Me | F | CF₃ |
| tBu | H | Me | F | COCH₃ |
| tBu | H | Me | F | CH₂OCH₃ |
| tBu | H | Me | F | Ph |
| tBu | H | Me | Cl | H |
| tBu | H | Me | Cl | Me |
| tBu | H | Me | Cl | Et |
| tBu | H | Me | Cl | tBu |
| tBu | H | Me | Cl | CF₃ |
| tBu | H | Me | Cl | COCH₃ |
| tBu | H | Me | Cl | CH₂OCH₃ |
| tBu | H | Me | Cl | Ph |
| tBu | H | Me | Br | H |
| tBu | H | Me | Br | Me |
| tBu | H | Me | Br | Et |
| tBu | H | Me | Br | tBu |
| tBu | H | Me | Br | CF₃ |
| tBu | H | Me | Br | COCH₃ |
| tBu | H | Me | Br | CH₂OCH₃ |
| tBu | H | Me | Br | Ph |
| tBu | H | Me | CF₃ | H |
| tBu | H | Me | CF₃ | Me |
| tBu | H | Me | CF₃ | Et |
| tBu | H | Me | CF₃ | tBu |
| tBu | H | Me | CF₃ | CF₃ |
| tBu | H | Me | CF₃ | COCH₃ |
| tBu | H | Me | CF₃ | CH₂OCH₃ |
| tBu | H | Me | CF₃ | Ph |
| tBu | H | Me | OH | H |
| tBu | H | Me | OH | Me |
| tBu | H | Me | OH | Et |
| tBu | H | Me | OH | tBu |
| tBu | H | Me | OH | CF₃ |
| tBu | H | Me | OH | COCH₃ |
| tBu | H | Me | OH | CH₂OCH₃ |
| tBu | H | Me | OH | Ph |
| tBu | H | Me | OMe | H |
| tBu | H | Me | OMe | Me |
| tBu | H | Me | OMe | Et |
| tBu | H | Me | OMe | tBu |
| tBu | H | Me | OMe | CF₃ |
| tBu | H | Me | OMe | COCH₃ |
| tBu | H | Me | OMe | CH₂OCH₃ |
| tBu | H | Me | OMe | Ph |
| tBu | H | Me | SMe | H |
| tBu | H | Me | SMe | Me |
| tBu | H | Me | SMe | Et |
| tBu | H | Me | SMe | tBu |
| tBu | H | Me | SMe | CF₃ |
| tBu | H | Me | SMe | COCH₃ |
| tBu | H | Me | SMe | CH₂OCH₃ |
| tBu | H | Me | SMe | Ph |
| tBu | H | Me | NO₂ | H |
| tBu | H | Me | NO₂ | Me |
| tBu | H | Me | NO₂ | Et |
| tBu | H | Me | NO₂ | tBu |
| tBu | H | Me | NO₂ | CF₃ |
| tBu | H | Me | NO₂ | COCH₃ |
| tBu | H | Me | NO₂ | CH₂OCH₃ |
| tBu | H | Me | NO₂ | Ph |
| tBu | H | Me | CN | H |
| tBu | H | Me | CN | Me |
| tBu | H | Me | CN | Et |
| tBu | H | Me | CN | tBu |
| tBu | H | Me | CN | CF₃ |
| tBu | H | Me | CN | COCH₃ |
| tBu | H | Me | CN | CH₂OCH₃ |
| tBu | H | Me | CN | Ph |
| tBu | H | Me | CO₂Me | H |
| tBu | H | Me | CO₂Me | Me |
| tBu | H | Me | CO₂Me | Et |
| tBu | H | Me | CO₂Me | tBu |
| tBu | H | Me | CO₂Me | CF₃ |
| tBu | H | Me | CO₂Me | COCH₃ |
| tBu | H | Me | CO₂Me | CH₂OCH₃ |
| tBu | H | Me | CO₂Me | Ph |
| tBu | H | Me | NMe₂ | H |
| tBu | H | Me | NMe₂ | Me |
| tBu | H | Me | NMe₂ | Et |
| tBu | H | Me | NMe₂ | tBu |
| tBu | H | Me | NMe₂ | CF₃ |
| tBu | H | Me | NMe₂ | COCH₃ |
| tBu | H | Me | NMe₂ | CH₂OCH₃ |
| tBu | H | Me | NMe₂ | Ph |
| tBu | H | Et | H | H |
| tBu | H | Et | H | Me |
| tBu | H | Et | H | Et |
| tBu | H | Et | H | tBu |
| tBu | H | Et | H | CF₃ |
| tBu | H | Et | H | COCH₃ |
| tBu | H | Et | H | CH₂OCH₃ |
| tBu | H | Et | H | Ph |
| tBu | H | Et | Me | H |
| tBu | H | Et | Me | Me |
| tBu | H | Et | Me | Et |
| tBu | H | Et | Me | tBu |
| tBu | H | Et | Me | CF₃ |
| tBu | H | Et | Me | COCH₃ |
| tBu | H | Et | Me | CH₂OCH₃ |
| tBu | H | Et | Me | Ph |
| tBu | H | Et | Et | H |
| tBu | H | Et | Et | Me |
| tBu | H | Et | Et | Et |
| tBu | H | Et | Et | tBu |
| tBu | H | Et | Et | CF₃ |

TABLE 1-continued

| | | | | |
|---|---|---|---|---|
| tBu | H | Et | Et | COCH$_3$ |
| tBu | H | Et | Et | CH$_2$OCH$_3$ |
| tBu | H | Et | Et | Ph |
| tBu | H | Et | iPr | H |
| tBu | H | Et | iPr | Me |
| tBu | H | Et | iPr | Et |
| tBu | H | Et | iPr | tBu |
| tBu | H | Et | iPr | CF$_3$ |
| tBu | H | Et | iPr | COCH$_3$ |
| tBu | H | Et | iPr | CH$_2$OCH$_3$ |
| tBu | H | Et | iPr | Ph |
| tBu | H | Et | tBu | H |
| tBu | H | Et | tBu | Me |
| tBu | H | Et | tBu | Et |
| tBu | H | Et | tBu | tBu |
| tBu | H | Et | tBu | CF$_3$ |
| tBu | H | Et | tBu | COCH$_3$ |
| tBu | H | Et | tBu | CH$_2$OCH$_3$ |
| tBu | H | Et | tBu | Ph |
| tBu | H | Et | Ph | H |
| tBu | H | Et | Ph | Me |
| tBu | H | Et | Ph | Et |
| tBu | H | Et | Ph | tBu |
| tBu | H | Et | Ph | CF$_3$ |
| tBu | H | Et | Ph | COCH$_3$ |
| tBu | H | Et | Ph | CH$_2$OCH$_3$ |
| tBu | H | Et | Ph | Ph |
| tBu | H | Et | F | H |
| tBu | H | Et | F | Me |
| tBu | H | Et | F | Et |
| tBu | H | Et | F | tBu |
| tBu | H | Et | F | CF$_3$ |
| tBu | H | Et | F | COCH$_3$ |
| tBu | H | Et | F | CH$_2$OCH$_3$ |
| tBu | H | Et | F | Ph |
| tBu | H | Et | Cl | H |
| tBu | H | Et | Cl | Me |
| tBu | H | Et | Cl | Et |
| tBu | H | Et | Cl | tBu |
| tBu | H | Et | Cl | CF$_3$ |
| tBu | H | Et | Cl | COCH$_3$ |
| tBu | H | Et | Cl | CH$_2$OCH$_3$ |
| tBu | H | Et | Cl | Ph |
| tBu | H | Et | Br | H |
| tBu | H | Et | Br | Me |
| tBu | H | Et | Br | Et |
| tBu | H | Et | Br | tBu |
| tBu | H | Et | Br | CF$_3$ |
| tBu | H | Et | Br | COCH$_3$ |
| tBu | H | Et | Br | CH$_2$OCH$_3$ |
| tBu | H | Et | Br | Ph |
| tBu | H | Et | CF$_3$ | H |
| tBu | H | Et | CF$_3$ | Me |
| tBu | H | Et | CF$_3$ | Et |
| tBu | H | Et | CF$_3$ | tBu |
| tBu | H | Et | CF$_3$ | CF$_3$ |
| tBu | H | Et | CF$_3$ | COCH$_3$ |
| tBu | H | Et | CF$_3$ | CH$_2$OCH$_3$ |
| tBu | H | Et | CF$_3$ | Ph |
| tBu | H | Et | OH | H |
| tBu | H | Et | OH | Me |
| tBu | H | Et | OH | Et |
| tBu | H | Et | OH | tBu |
| tBu | H | Et | OH | CF$_3$ |
| tBu | H | Et | OH | COCH$_3$ |
| tBu | H | Et | OH | CH$_2$OCH$_3$ |
| tBu | H | Et | OH | Ph |
| tBu | H | Et | OMe | H |
| tBu | H | Et | OMe | Me |
| tBu | H | Et | OMe | Et |
| tPen | H | Et | OMe | tBu |
| tPen | H | Et | OMe | CF$_3$ |
| tPen | H | Et | OMe | COCH$_3$ |
| tPen | H | Et | OMe | CH$_2$OCH$_3$ |
| tPen | H | Et | OMe | Ph |
| tPen | H | Et | SMe | H |
| tPen | H | Et | SMe | Me |
| tPen | H | Et | SMe | Et |
| tPen | H | Et | SMe | tBu |
| tPen | H | Et | SMe | CF$_3$ |
| tPen | H | Et | SMe | COCH$_3$ |
| tPen | H | Et | SMe | CH$_2$OCH$_3$ |
| tPen | H | Et | SMe | Ph |
| tPen | H | Et | NO$_2$ | H |
| tPen | H | Et | NO$_2$ | Me |
| tPen | H | Et | NO$_2$ | Et |
| tPen | H | Et | NO$_2$ | tBu |
| tPen | H | Et | NO$_2$ | CF$_3$ |
| tPen | H | Et | NO$_2$ | COCH$_3$ |
| tPen | H | Et | NO$_2$ | CH$_2$OCH$_3$ |
| tPen | H | Et | NO$_2$ | Ph |
| tPen | H | Et | CN | H |
| tBuCH$_2$ | H | Et | CN | Me |
| tBuCH$_2$ | H | Et | CN | Et |
| tBuCH$_2$ | H | Et | CN | tBu |
| tBuCH$_2$ | H | Et | CN | CF$_3$ |
| tBuCH$_2$ | H | Et | CN | COCH$_3$ |
| tBuCH$_2$ | H | Et | CN | CH$_2$OCH$_3$ |
| tBuCH$_2$ | H | Et | CN | Ph |
| tBuCH$_2$ | H | Et | CO$_2$Me | H |
| tBuCH$_2$ | H | Et | CO$_2$Me | Me |
| tBuCH$_2$ | H | Et | CO$_2$Me | Et |
| tBuCH$_2$ | H | Et | CO$_2$Me | tBu |
| tBuCH$_2$ | H | Et | CO$_2$Me | CF$_3$ |
| tBuCH$_2$ | H | Et | CO$_2$Me | COCH$_3$ |
| tBuCH$_2$ | H | Et | CO$_2$Me | CH$_2$OCH$_3$ |
| tBuCH$_2$ | H | Et | CO$_2$Me | Ph |
| tBuCH$_2$ | H | Et | NMe$_2$ | H |
| tBuCH$_2$ | H | Et | NMe$_2$ | Me |
| tBuCH$_2$ | H | Et | NMe$_2$ | Et |
| tBuCH$_2$ | H | Et | NMe$_2$ | tBu |
| tBuCH$_2$ | H | Et | NMe$_2$ | CF$_3$ |
| tBuCH$_2$ | H | Et | NMe$_2$ | COCH$_3$ |
| tBuCH$_2$ | H | Et | NMe$_2$ | CH$_2$OCH$_3$ |
| tBuCH$_2$ | H | Et | NMe$_2$ | Ph |
| nPrMe$_2$C | H | iPr | H | H |
| nPrMe$_2$C | H | iPr | H | Me |
| nPrMe$_2$C | H | iPr | H | Et |
| nPrMe$_2$C | H | iPr | H | tBu |
| nPrMe$_2$C | H | iPr | H | CF$_3$ |
| nPrMe$_2$C | H | iPr | H | COCH$_3$ |
| nPrMe$_2$C | H | iPr | H | CH$_2$OCH$_3$ |
| nPrMe$_2$C | H | iPr | H | Ph |
| nPrMe$_2$C | H | iPr | Me | H |
| nPrMe$_2$C | H | iPr | Me | Me |
| nPrMe$_2$C | H | iPr | Me | Et |
| nPrMe$_2$C | H | iPr | Me | tBu |
| nBuMeEtC | H | iPr | Me | CF$_3$ |
| nBuMeEtC | H | iPr | Me | COCH$_3$ |
| nBuMeEtC | H | iPr | Me | CH$_2$OCH$_3$ |
| nBuMeEtC | H | iPr | Me | Ph |
| nBuMeEtC | H | iPr | Et | H |
| nBuMeEtC | H | iPr | Et | Me |
| nBuMeEtC | H | iPr | Et | Et |
| nBuMeEtC | H | iPr | Et | tBu |
| nBuMeEtC | H | iPr | Et | CF$_3$ |
| nBuMeEtC | H | iPr | Et | COCH$_3$ |
| tBu | H | iPr | Et | CH$_2$OCH$_3$ |
| tBu | H | iPr | Et | Ph |
| tBu | H | iPr | iPr | H |
| tBu | H | iPr | iPr | Me |
| tBu | H | iPr | iPr | Et |
| tBu | H | iPr | iPr | tBu |
| tBu | H | iPr | iPr | CF$_3$ |
| tBu | H | iPr | iPr | COCH$_3$ |
| tBu | H | iPr | iPr | CH$_2$OCH$_3$ |
| tBu | H | iPr | iPr | Ph |
| tBu | H | iPr | tBu | H |
| tBu | H | iPr | tBu | Me |
| tBu | H | iPr | tBu | Et |
| tBu | H | iPr | tBu | tBu |
| tBu | H | iPr | tBu | CF$_3$ |
| tBu | H | iPr | tBu | COCH$_3$ |
| tBu | H | iPr | tBu | CH$_2$OCH$_3$ |
| tBu | H | iPr | tBu | Ph |
| tBu | H | iPr | Ph | H |
| tBu | H | iPr | Ph | Me |
| tBu | H | iPr | Ph | Et |

TABLE 1-continued

| | | | | |
|---|---|---|---|---|
| tBu | H | iPr | Ph | tBu |
| tBu | H | iPr | Ph | CF$_3$ |
| tBu | H | iPr | Ph | COCH$_3$ |
| tBu | H | iPr | Ph | CH$_2$OCH$_3$ |
| tBu | H | iPr | Ph | Ph |
| tBu | H | iPr | F | H |
| tBu | H | iPr | F | Me |
| tBu | H | iPr | F | Et |
| tBu | H | iPr | F | tBu |
| tBu | H | iPr | F | CF$_3$ |
| tBu | H | iPr | F | COCH$_3$ |
| tBu | H | iPr | F | CH$_2$OCH$_3$ |
| tBu | H | iPr | F | Ph |
| tBu | H | iPr | Cl | H |
| tBu | H | iPr | Cl | Me |
| tBu | H | iPr | Cl | Et |
| tBu | H | iPr | Cl | tBu |
| tBu | H | iPr | Cl | CF$_3$ |
| tBu | H | iPr | Cl | COCH$_3$ |
| tBu | H | iPr | Cl | CH$_2$OCH$_3$ |
| tBu | H | iPr | Cl | Ph |
| tBu | H | iPr | Br | H |
| 1-naphthyl | H | iPr | Br | Me |
| 1-naphthyl | H | iPr | Br | Et |
| 1-naphthyl | H | iPr | Br | tBu |
| 1-naphthyl | H | iPr | Br | CF$_3$ |
| 1-naphthyl | H | iPr | Br | COCH$_3$ |
| 1-naphthyl | H | iPr | Br | CH$_2$OCH$_3$ |
| 1-naphthyl | H | iPr | Br | Ph |
| 1-naphthyl | H | iPr | CF$_3$ | H |
| 1-naphthyl | H | iPr | CF$_3$ | Me |
| 1-naphthyl | H | iPr | CF$_3$ | Et |
| 1-naphthyl | H | iPr | CF$_3$ | tBu |
| 1-naphthyl | H | iPr | CF$_3$ | CF$_3$ |
| 1-naphthyl | H | iPr | CF$_3$ | COCH$_3$ |
| 2-naphthyl | H | iPr | CF$_3$ | CH$_2$OCH$_3$ |
| 2-naphthyl | H | iPr | CF$_3$ | Ph |
| 2-naphthyl | H | iPr | OH | H |
| 2-naphthyl | H | iPr | OH | Me |
| 2-naphthyl | H | iPr | OH | Et |
| 2-naphthyl | H | iPr | OH | tBu |
| 2-naphthyl | H | iPr | OH | CF$_3$ |
| 2-naphthyl | H | iPr | OH | COCH$_3$ |
| 2-naphthyl | H | iPr | OH | CH$_2$OCH$_3$ |
| 2-pyridinyl | H | iPr | OH | Ph |
| 2-pyridinyl | H | iPr | OMe | H |
| 2-pyridinyl | H | iPr | OMe | Me |
| 2-pyridinyl | H | iPr | OMe | Et |
| 2-pyridinyl | H | iPr | OMe | tBu |
| 2-pyridinyl | H | iPr | OMe | CF$_3$ |
| 2-pyridinyl | H | iPr | OMe | COCH$_3$ |
| 2-pyridinyl | H | iPr | OMe | CH$_2$OCH$_3$ |
| 2-pyridinyl | H | iPr | OMe | Ph |
| 2-pyridinyl | H | iPr | SMe | H |
| 2-pyridinyl | H | iPr | SMe | Me |
| 2-pyridinyl | H | iPr | SMe | Et |
| 3-pyridinyl | H | iPr | SMe | tBu |
| 3-pyridinyl | H | iPr | SMe | CF$_3$ |
| 3-pyridinyl | H | iPr | SMe | COCH$_3$ |
| 3-pyridinyl | H | iPr | SMe | CH$_2$OCH$_3$ |
| 3-pyridinyl | H | iPr | SMe | Ph |
| 4-pyridinyl | H | iPr | NO$_2$ | H |
| 4-pyridinyl | H | iPr | NO$_2$ | Me |
| 4-pyridinyl | H | iPr | NO$_2$ | Et |
| 4-pyridinyl | H | iPr | NO$_2$ | tBu |
| 4-pyridinyl | H | iPr | NO$_2$ | CF$_3$ |
| cHex | H | iPr | NO$_2$ | COCH$_3$ |
| cHex | H | iPr | NO$_2$ | CH$_2$OCH$_3$ |
| cHex | H | iPr | NO$_2$ | Ph |
| cHex | H | iPr | CN | H |
| cHex | H | iPr | CN | Me |
| cHex | H | iPr | CN | Et |
| cHex | H | iPr | CN | tBu |
| cHex | H | iPr | CN | CF$_3$ |
| cHex | H | iPr | CN | COCH$_3$ |
| cHex | H | iPr | CN | CH$_2$OCH$_3$ |
| cHex | H | iPr | CN | Ph |
| cHex | H | iPr | CO$_2$Me | H |
| cHex | H | iPr | CO$_2$Me | Me |
| cHex | H | iPr | CO$_2$Me | Et |
| cHex | H | iPr | CO$_2$Me | tBu |
| cHex | H | iPr | CO$_2$Me | CF$_3$ |
| cHex | H | iPr | CO$_2$Me | COCH$_3$ |
| cHex | H | iPr | CO$_2$Me | CH$_2$OCH$_3$ |
| cHex | H | iPr | CO$_2$Me | Ph |
| cHex | H | iPr | NMe$_2$ | H |
| cHex | H | iPr | NMe$_2$ | Me |
| cHex | H | iPr | NMe$_2$ | Et |
| tBu | H | iPr | NMe$_2$ | tBu |
| tBu | H | iPr | NMe$_2$ | CF$_3$ |
| tBu | H | iPr | NMe$_2$ | COCH$_3$ |
| tBu | H | iPr | NMe$_2$ | CH$_2$OCH$_3$ |
| tBu | H | iPr | NMe$_2$ | Ph |
| tBu | H | tBu | H | H |
| tBu | H | tBu | H | Me |
| tBu | H | tBu | H | Et |
| tBu | H | tBu | H | tBu |
| tBu | H | tBu | H | CF$_3$ |
| tBu | H | tBu | H | COCH$_3$ |
| tBu | H | tBu | H | CH$_2$OCH$_3$ |
| tBu | H | tBu | H | Ph |
| tBu | H | tBu | Me | H |
| tBu | H | tBu | Me | Me |
| tBu | H | tBu | Me | Et |
| tBu | H | tBu | Me | tBu |
| tBu | H | tBu | Me | CF$_3$ |
| tBu | H | tBu | Me | COCH$_3$ |
| tBu | H | tBu | Me | CH$_2$OCH$_3$ |
| tBu | H | tBu | Me | Ph |
| tBu | H | tBu | Et | H |
| tBu | H | tBu | Et | Me |
| tBu | H | tBu | Et | Et |
| tBu | H | tBu | Et | tBu |
| tBu | H | tBu | Et | CF$_3$ |
| tBu | H | tBu | Et | COCH$_3$ |
| tBu | H | tBu | Et | CH$_2$OCH$_3$ |
| tBu | H | tBu | Et | Ph |
| tBu | H | tBu | iPr | H |
| tBu | H | tBu | iPr | Me |
| tBu | H | tBu | iPr | Et |
| tBu | H | tBu | iPr | tBu |
| tBu | H | tBu | iPr | CF$_3$ |
| tBu | H | tBu | iPr | COCH$_3$ |
| tBu | H | tBu | iPr | CH$_2$OCH$_3$ |
| tBu | H | tBu | iPr | Ph |
| tBu | H | tBu | tBu | H |
| tBu | H | tBu | tBu | Me |
| tBu | H | tBu | tBu | Et |
| tBu | H | tBu | tBu | tBu |
| tBu | H | tBu | tBu | CF$_3$ |
| tBu | H | tBu | tBu | COCH$_3$ |
| tBu | H | tBu | tBu | CH$_2$OCH$_3$ |
| tBu | H | tBu | tBu | Ph |
| tBu | H | tBu | Ph | H |
| tBu | H | tBu | Ph | Me |
| tBu | H | tBu | Ph | Et |
| tBu | H | tBu | Ph | tBu |
| tBu | H | tBu | Ph | CF$_3$ |
| tBu | H | tBu | Ph | COCH$_3$ |
| tBu | H | tBu | Ph | CH$_2$OCH$_3$ |
| tBu | H | tBu | Ph | Ph |
| tBu | H | tBu | F | H |
| tBu | H | tBu | F | Me |
| tBu | H | tBu | F | Et |
| tBu | H | tBu | F | tBu |
| tBu | H | tBu | F | CF$_3$ |
| tBu | H | tBu | F | COCH$_3$ |
| tBu | H | tBu | F | CH$_2$OCH$_3$ |
| tBu | H | tBu | F | Ph |
| tBu | H | tBu | Cl | H |
| tBu | H | tBu | Cl | Me |
| tBu | H | tBu | Cl | Et |
| tBu | H | tBu | Cl | tBu |
| tBu | H | tBu | Cl | CF$_3$ |
| tBu | H | tBu | Cl | COCH$_3$ |
| tBu | H | tBu | Cl | CH$_2$OCH$_3$ |
| tBu | H | tBu | Cl | Ph |
| tBu | H | tBu | Br | H |

TABLE 1-continued

| | | | | |
|---|---|---|---|---|
| tBu | H | tBu | Br | Me |
| tBu | H | tBu | Br | Et |
| tBu | H | tBu | Br | tBu |
| tBu | H | tBu | Br | $CF_3$ |
| tBu | H | tBu | Br | $COCH_3$ |
| tBu | H | tBu | Br | $CH_2OCH_3$ |
| tBu | H | tBu | Br | Ph |
| tBu | H | tBu | $CF_3$ | H |
| tBu | H | tBu | $CF_3$ | Me |
| tBu | H | tBu | $CF_3$ | Et |
| tBu | H | tBu | $CF_3$ | tBu |
| tBu | H | tBu | $CF_3$ | $CF_3$ |
| tBu | H | tBu | $CF_3$ | $COCH_3$ |
| tBu | H | tBu | $CF_3$ | $CH_2OCH_3$ |
| tBu | H | tBu | $CF_3$ | Ph |
| tBu | H | tBu | OH | H |
| tBu | H | tBu | OH | Me |
| tBu | H | tBu | OH | Et |
| 2,6-$F_2$—Ph | H | tBu | OH | tBu |
| 2,6-$F_2$—Ph | H | tBu | OH | $CF_3$ |
| 2,6-$F_2$—Ph | H | tBu | OH | $COCH_3$ |
| 2,6-$F_2$—Ph | H | tBu | OH | $CH_2OCH_3$ |
| 2,6-$F_2$—Ph | H | tBu | OH | Ph |
| 2,6-$F_2$—Ph | H | tBu | OMe | H |
| 2,6-$F_2$—Ph | H | tBu | OMe | Me |
| 2,6-$F_2$—Ph | H | tBu | OMe | Et |
| 2,6-$F_2$—Ph | H | tBu | OMe | tBu |
| 2,6-$F_2$—Ph | H | tBu | OMe | $CF_3$ |
| 2,6-$F_2$—Ph | H | tBu | OMe | $COCH_3$ |
| 2,6-$F_2$—Ph | H | tBu | OMe | $CH_2OCH_3$ |
| 2,6-$F_2$—Ph | H | tBu | OMe | Ph |
| 2,6-$F_2$—Ph | H | tBu | SMe | H |
| 2,6-$F_2$—Ph | H | tBu | SMe | Me |
| 2,6-$F_2$—Ph | H | tBu | SMe | Et |
| 2,6-$F_2$—Ph | H | tBu | SMe | tBu |
| 2,6-$F_2$—Ph | H | tBu | SMe | $CF_3$ |
| 2,6-$F_2$—Ph | H | tBu | SMe | $COCH_3$ |
| 2,6-$F_2$—Ph | H | tBu | SMe | $CH_2OCH_3$ |
| 2,6-$F_2$—Ph | H | tBu | SMe | Ph |
| tBu | H | tBu | $NO_2$ | H |
| tBu | H | tBu | $NO_2$ | $CH_2OEt$ |
| tBu | H | tBu | $NO_2$ | Et |
| tBu | H | tBu | $NO_2$ | tBu |
| tBu | H | tBu | $NO_2$ | $CF_3$ |
| tBu | H | tBu | $NO_2$ | $COCH_3$ |
| tBu | H | tBu | $NO_2$ | $CH_2OCH_3$ |
| tBu | H | tBu | $NO_2$ | Ph |
| tBu | H | tBu | CN | H |
| tBu | H | tBu | CN | Me |
| tBu | H | tBu | CN | Et |
| tBu | H | tBu | CN | tBu |
| tBu | H | tBu | CN | $CF_3$ |
| tBu | H | tBu | CN | $COCH_3$ |
| tBu | H | tBu | CN | $CH_2OCH_3$ |
| tBu | H | tBu | CN | Ph |
| tBu | H | tBu | $CO_2Me$ | H |
| tBu | H | tBu | $CO_2Me$ | Me |
| tBu | H | tBu | $CO_2Me$ | Et |
| tBu | H | tBu | $CO_2Me$ | tBu |
| tBu | H | tBu | $CO_2Me$ | $CF_3$ |
| tBu | H | tBu | $CO_2Me$ | $COCH_3$ |
| tBu | H | tBu | $CO_2Me$ | $CH_2OCH_3$ |
| tBu | H | H | $CF_3$ | Ph |
| tBu | H | H | $CF_3$ | H |
| tBu | H | H | $CF_3$ | Et |
| tBu | H | H | $CF_3$ | $PhCH_2$ |
| tBu | H | H | $CF_3$ | tBu |
| tBu | H | H | $CF_3$ | $CF_3$ |
| tBu | H | H | $CF_3$ | $COCH_3$ |
| tBu | H | H | $CF_3$ | $CH_2OCH_3$ |
| tBu | H | tBu | $NMe_2$ | Ph |
| tBu | H | $CF_3$ | H | H |
| tBu | H | $CF_3$ | H | $PhCH_2$ |
| tBu | H | $CF_3$ | H | Et |
| tBu | H | $CF_3$ | H | tBu |
| tBu | H | $CF_3$ | H | $CF_3$ |
| tBu | H | $CF_3$ | H | $COCH_3$ |
| tBu | H | $CF_3$ | H | $CH_2OCH_3$ |
| tBu | H | $CF_3$ | H | Ph |
| tBu | H | $CF_3$ | Me | H |
| tBu | H | $CF_3$ | Me | Me |
| tBu | H | $CF_3$ | Me | Et |
| tBu | H | $CF_3$ | Me | tBu |
| tBu | H | $CF_3$ | Me | $CF_3$ |
| tBu | H | $CF_3$ | Me | $COCH_3$ |
| tBu | H | $CF_3$ | Me | $CH_2OCH_3$ |
| tBu | H | $CF_3$ | Me | Ph |
| tBu | H | $CF_3$ | Et | H |
| tBu | H | $CF_3$ | Et | Me |
| tBu | H | $CF_3$ | Et | Et |
| tBu | H | $CF_3$ | Et | tBu |
| tBu | H | $CF_3$ | Et | $CF_3$ |
| tBu | H | $CF_3$ | Et | $COCH_3$ |
| tBu | H | $CF_3$ | Et | $CH_2OCH_3$ |
| tBu | H | $CF_3$ | Et | Ph |
| tBu | H | $CF_3$ | iPr | H |
| tBu | H | $CF_3$ | iPr | Me |
| tBu | H | $CF_3$ | iPr | Et |
| tBu | H | $CF_3$ | iPr | tBu |
| tBu | H | $CF_3$ | iPr | $CF_3$ |
| tBu | H | $CF_3$ | iPr | $COCH_3$ |
| tBu | H | $CF_3$ | iPr | $CH_2OCH_3$ |
| tBu | H | $CF_3$ | iPr | Ph |
| tBu | H | $CF_3$ | tBu | H |
| tBu | H | $CF_3$ | tBu | Me |
| tBu | H | $CF_3$ | tBu | Et |
| tBu | H | $CF_3$ | tBu | tBu |
| tBu | H | $CF_3$ | tBu | $CF_3$ |
| tBu | H | $CF_3$ | tBu | $COCH_3$ |
| tBu | H | $CF_3$ | tBu | $CH_2OCH_3$ |
| tBu | H | $CF_3$ | tBu | Ph |
| tBu | H | $CF_3$ | Ph | H |
| tBu | H | $CF_3$ | Ph | Me |
| tBu | H | $CF_3$ | Ph | Et |
| tBu | H | $CF_3$ | Ph | tBu |
| tBu | H | $CF_3$ | Ph | $CF_3$ |
| tBu | H | $CF_3$ | Ph | $COCH_3$ |
| tBu | H | $CF_3$ | Ph | $CH_2OCH_3$ |
| tBu | H | $CF_3$ | Ph | Ph |
| tBu | H | $CF_3$ | F | H |
| tBu | H | $CF_3$ | F | Me |
| tBu | H | $CF_3$ | F | Et |
| tBu | H | $CF_3$ | F | tBu |
| tBu | H | $CF_3$ | F | $CF_3$ |
| tBu | H | $CF_3$ | F | $COCH_3$ |
| tBu | H | $CF_3$ | F | $CH_2OCH_3$ |
| tBu | H | $CF_3$ | F | Ph |
| tBu | $CF_3$ | $CF_3$ | Cl | H |
| tBu | H | $CF_3$ | Cl | Me |
| tBu | H | $CF_3$ | Cl | Et |
| tBu | H | $CF_3$ | Cl | tBu |
| tBu | H | $CF_3$ | Cl | $CF_3$ |
| tBu | H | $CF_3$ | Cl | $COCH_3$ |
| tBu | H | $CF_3$ | Cl | $CH_2OCH_3$ |
| tBu | H | $CF_3$ | Cl | Ph |
| tBu | H | $CF_3$ | Br | H |
| tBu | H | $CF_3$ | Br | Me |
| tBu | H | $CF_3$ | Br | Et |
| tBu | H | $CF_3$ | Br | tBu |
| tBu | H | $CF_3$ | Br | $CF_3$ |
| tBu | H | $CF_3$ | Br | $COCH_3$ |
| tBu | H | $CF_3$ | Br | $CH_2OCH_3$ |
| tBu | H | $CF_3$ | Br | Ph |
| tBu | H | $CF_3$ | $CF_3$ | H |
| tBu | H | $CF_3$ | $CF_3$ | Me |
| tBu | H | $CF_3$ | $CF_3$ | Et |
| tBu | H | $CF_3$ | $CF_3$ | tBu |
| tBu | H | $CF_3$ | $CF_3$ | $CF_3$ |
| tBu | H | $CF_3$ | $CF_3$ | $COCH_3$ |
| tBu | H | $CF_3$ | $CF_3$ | $CH_2OCH_3$ |
| H | tBu | $CF_3$ | Cl | Ph |
| H | tBu | $CF_3$ | Cl | H |
| Me | tBu | $CF_3$ | Cl | Me |
| Et | tBu | $CF_3$ | Cl | Et |
| nOct | tBu | $CF_3$ | Cl | tBu |
| H | tBu | $CF_3$ | Cl | $CF_3$ |
| H | tBu | $CF_3$ | Br | $COCH_3$ |
| H | tBu | $CF_3$ | Br | $CH_2OCH_3$ |

TABLE 1-continued

| | | | | |
|---|---|---|---|---|
| H | tBu | CF$_3$ | Br | Ph |
| H | tBu | CF$_3$ | Br | H |
| H | tBu | CF$_3$ | Br | Me |
| Me | tBu | CF$_3$ | Br | Et |
| tPen | tBu | CF$_3$ | Br | tBu |
| nHep | tBu | CF$_3$ | OMe | CF$_3$ |
| tBu | H | CF$_3$ | OMe | COCH$_3$ |
| tBu | H | CF$_3$ | OMe | CH$_2$OCH$_3$ |
| tBu | H | CF$_3$ | OMe | Ph |
| tBu | H | CF$_3$ | SMe | H |
| tBu | H | CF$_3$ | SMe | Me |
| tBu | H | CF$_3$ | SMe | Et |
| tBu | H | CF$_3$ | SMe | tBu |
| tBu | H | CF$_3$ | SMe | CF$_3$ |
| tBu | H | CF$_3$ | SMe | COCH$_3$ |
| tBu | H | CF$_3$ | SMe | CH$_2$OCH$_3$ |
| tBu | H | CF$_3$ | SMe | Ph |
| tBu | H | CF$_3$ | NO$_2$ | H |
| tBu | H | CF$_3$ | NO$_2$ | Me |
| tBu | H | CF$_3$ | NO$_2$ | Et |
| tBu | H | CF$_3$ | NO$_2$ | tBu |
| tBu | H | CF$_3$ | NO$_2$ | CF$_3$ |
| tBu | H | CF$_3$ | NO$_2$ | COCH$_3$ |
| tBu | H | CF$_3$ | NO$_2$ | CH$_2$OCH$_3$ |
| tBu | H | CF$_3$ | NO$_2$ | Ph |
| tBu | H | CF$_3$ | CN | H |
| tBu | H | CF$_3$ | CN | Me |
| tBu | H | CF$_3$ | CN | Et |
| tBu | H | CF$_3$ | CN | tBu |
| tBu | H | CF$_3$ | CN | CF$_3$ |
| tBu | H | CF$_3$ | CN | COCH$_3$ |
| tBu | H | CF$_3$ | CN | CH$_2$OCH$_3$ |
| tBu | H | CF$_3$ | CN | Ph |
| tBu | H | CF$_3$ | CO$_2$Me | H |
| tBu | H | CF$_3$ | CO$_2$Me | Me |
| tBu | H | CF$_3$ | CO$_2$Me | Et |
| tBu | H | CF$_3$ | CO$_2$Me | tBu |
| tBu | H | CF$_3$ | CO$_2$Me | CF$_3$ |
| tBu | H | CF$_3$ | CO$_2$Me | COCH$_3$ |
| tBu | H | CF$_3$ | CO$_2$Me | CH$_2$OCH$_3$ |
| tBu | H | CF$_3$ | CO$_2$Me | Ph |
| tBu | H | CF$_3$ | NMe$_2$ | H |
| tBu | H | CF$_3$ | NMe$_2$ | Me |
| tBu | H | CF$_3$ | NMe$_2$ | Et |
| tBu | H | CF$_3$ | NMe$_2$ | tBu |
| tBu | H | CF$_3$ | NMe$_2$ | CF$_3$ |
| tBu | H | CF$_3$ | NMe$_2$ | COCH$_3$ |
| tBu | H | CF$_3$ | NMe$_2$ | CH$_2$OCH$_3$ |
| tBu | H | CF$_3$ | NMe$_2$ | Ph |
| tBu | H | Cl | H | H |
| tBu | H | Cl | H | Me |
| tBu | H | Cl | H | Et |
| tBu | H | Cl | H | tBu |
| tBu | H | Cl | H | CF$_3$ |
| tBu | H | Cl | H | COCH$_3$ |
| tBu | H | Cl | H | CH$_2$OCH$_3$ |
| tBu | H | Cl | H | Ph |
| tBu | H | Cl | Me | H |
| tBu | H | Cl | Me | Me |
| tBu | H | Cl | Me | Et |
| tBu | H | Cl | Me | tBu |
| tBu | H | Cl | Me | CF$_3$ |
| tBu | H | Cl | Me | COCH$_3$ |
| tBu | H | Cl | Me | CH$_2$OCH$_3$ |
| tBu | H | Cl | Me | Ph |
| tBu | H | Cl | Et | H |
| tBu | H | Cl | Et | Me |
| tBu | H | Cl | Et | Et |
| tBu | H | Cl | Et | tBu |
| tBu | H | Cl | Et | CF$_3$ |
| tBu | H | Cl | Et | COCH$_3$ |
| tBu | H | Cl | Et | CH$_2$OCH$_3$ |
| tBu | H | Cl | Et | Ph |
| tBu | H | Cl | iPr | H |
| tBu | H | Cl | iPr | Me |
| tBu | H | Cl | iPr | Et |
| tBu | H | Cl | iPr | tBu |
| tBu | H | Cl | iPr | CF$_3$ |
| tBu | H | Cl | iPr | COCH$_3$ |
| tBu | H | Cl | iPr | CH$_2$OCH$_3$ |
| tBu | H | Cl | iPr | Ph |
| tBu | H | Cl | tBu | H |
| tBu | H | Cl | tBu | Me |
| tBu | H | Cl | tBu | Et |
| tBu | H | Cl | tBu | tBu |
| tBu | H | Cl | tBu | CF$_3$ |
| tBu | H | Cl | tBu | COCH$_3$ |
| tBu | H | Cl | tBu | CH$_2$OCH$_3$ |
| tBu | H | Cl | tBu | Ph |
| tBu | H | Cl | Ph | H |
| tBu | H | Cl | Ph | Me |
| tBu | H | Cl | Ph | Et |
| tBu | H | Cl | Ph | tBu |
| tBu | H | Cl | Ph | CF$_3$ |
| tBu | H | Cl | Ph | COCH$_3$ |
| tBu | H | Cl | Ph | CH$_2$OCH$_3$ |
| tBu | H | Cl | Ph | Ph |
| tBu | H | Cl | F | H |
| tBu | H | Cl | F | Me |
| tBu | H | Cl | F | Et |
| tBu | H | Cl | F | tBu |
| tBu | H | Cl | F | CF$_3$ |
| tBu | H | Cl | F | COCH$_3$ |
| tBu | H | Cl | F | CH$_2$OCH$_3$ |
| tBu | H | Cl | F | Ph |
| tBu | H | Cl | Cl | H |
| tBu | H | Cl | Cl | Me |
| tBu | H | Cl | Cl | Et |
| tBu | H | Cl | Cl | tBu |
| tBu | H | Cl | Cl | CF$_3$ |
| tBu | Me | Cl | Cl | COCH$_3$ |
| tBu | Et | Cl | Cl | CH$_2$OCH$_3$ |
| tBu | nPr | Cl | Cl | Ph |
| tBu | iPr | Cl | Br | H |
| tBu | nBu | Cl | Br | Me |
| tBu | CF$_3$ | Cl | Br | Et |
| tBu | H | Cl | Br | tBu |
| tBu | H | Cl | Br | CF$_3$ |
| tBu | H | Cl | Br | COCH$_3$ |
| tBu | H | Cl | Br | CH$_2$OCH$_3$ |
| tBu | H | Cl | Br | Ph |
| Me | tBu | Cl | CF$_3$ | H |
| Me | tBu | Cl | CF$_3$ | Me |
| Me | tBu | Cl | CF$_3$ | Et |
| tBu | H | Cl | CF$_3$ | tBu |
| tBu | H | Cl | CF$_3$ | CF$_3$ |
| tBu | H | Cl | CF$_3$ | COCH$_3$ |
| tBu | H | Cl | CF$_3$ | CH$_2$OCH$_3$ |
| tBu | H | Cl | CF$_3$ | Ph |
| tBu | H | Cl | OH | H |
| tBu | H | Cl | OH | Me |
| tBu | H | Cl | OH | Et |
| tBu | H | Cl | OH | tBu |
| tBu | H | Cl | OH | CF$_3$ |
| tBu | H | Cl | OH | COCH$_3$ |
| tBu | H | Cl | OH | CH$_2$OCH$_3$ |
| tBu | H | Cl | OH | Ph |
| tBu | H | Cl | OMe | H |
| tBu | H | Cl | OMe | Me |
| tBu | H | Cl | OMe | Et |
| tBu | H | Cl | OMe | tBu |
| tBu | H | Cl | OMe | CF$_3$ |
| tBu | H | Cl | OMe | COCH$_3$ |
| tBu | H | Cl | OMe | CH$_2$OCH$_3$ |
| tBu | H | Cl | OMe | Ph |
| tBu | H | Cl | SMe | H |
| tBu | H | Cl | SMe | Me |
| tBu | H | Cl | SMe | Et |
| tBu | H | Cl | SMe | tBu |
| tBu | H | Cl | SMe | CF$_3$ |
| tBu | H | Cl | SMe | COCH$_3$ |
| tBu | H | Cl | SMe | CH$_2$OCH$_3$ |
| tBu | H | Cl | SMe | Ph |
| tBu | H | Cl | NO$_2$ | H |
| tBu | H | Cl | NO$_2$ | Me |
| tBu | H | Cl | NO$_2$ | Et |
| tBu | H | Cl | NO$_2$ | tBu |
| tBu | H | Cl | NO$_2$ | CF$_3$ |

TABLE 1-continued

| | | | | |
|---|---|---|---|---|
| tBu | H | Cl | NO$_2$ | COCH$_3$ |
| tBu | H | Cl | NO$_2$ | CH$_2$OCH$_3$ |
| tBu | H | Cl | NO$_2$ | Ph |
| tBu | H | Cl | CN | H |
| tBu | H | Cl | CN | Me |
| tBu | H | Cl | CN | Et |
| tBu | H | Cl | CN | tBu |
| tBu | H | Cl | CN | CF$_3$ |
| tBu | H | Cl | CN | COCH$_3$ |
| tBu | H | Cl | CN | CH$_2$OCH$_3$ |
| H | tBu | Cl | CN | Ph |
| H | tBu | Cl | CO$_2$Me | H |
| H | tBu | Cl | CO$_2$Me | Me |
| H | tBu | Cl | CO$_2$Me | Et |
| H | tBu | Cl | CO$_2$Me | tBu |
| H | tBu | Cl | CO$_2$Me | CF$_3$ |
| H | tBu | Cl | CO$_2$Me | COCH$_3$ |
| H | tBu | Cl | CO$_2$Me | CH$_2$OCH$_3$ |
| H | tBu | Cl | CO$_2$Me | Ph |
| H | tBu | Cl | NMe$_2$ | H |
| H | tBu | Cl | NMe$_2$ | Me |
| H | tBu | Cl | NMe$_2$ | Et |
| H | tBu | Cl | NMe$_2$ | tBu |
| H | tBu | Cl | NMe$_2$ | CF$_3$ |
| H | tBu | Cl | NMe$_2$ | COCH$_3$ |
| H | tBu | Cl | NMe$_2$ | CH$_2$OCH$_3$ |
| H | tBu | Cl | NMe$_2$ | Ph |
| H | tBu | Cl | nPr | Me |
| H | tBu | Cl | nBu | Me |
| H | tBu | Cl | iBu | Me |
| H | tBu | Cl | sBu | Me |
| H | tBu | Cl | cPr | Me |
| tBu | H | Cl | I | Me |
| tBu | H | Cl | CHF$_2$ | Me |
| tBu | H | Cl | CH$_2$F | Me |
| tBu | H | Cl | OEt | Me |
| tBu | H | Cl | OPr | Me |
| tBu | H | Cl | O-tBu | Me |
| tBu | H | Cl | OPh | Me |
| tBu | H | Cl | SEt | Me |
| tBu | H | Cl | S-tBu | Me |
| tBu | H | Cl | CO$_2$Et | Me |
| tBu | H | Cl | CO$_2$Pr | Me |
| tBu | H | Cl | CO$_2$Bu | Me |
| tBu | H | Cl | NEt$_2$ | Me |
| tBu | H | Cl | Cl | nPr |
| tBu | H | Cl | Cl | iPr |
| tBu | Me | Cl | Cl | nBu |
| tBu | Et | Cl | Cl | iBu |
| tBu | nPr | Cl | Cl | sBu |
| tBu | iPr | Cl | Cl | CHF$_2$ |
| tBu | nBu | Cl | Cl | CH$_2$F |
| tBu | sBu | Cl | Cl | CH$_2$OEt |
| tBu | iBu | Cl | Cl | CH$_2$O-nPr |
| tBu | H | Cl | Cl | CH$_2$O-iPr |
| tBu | H | Cl | Cl | C$_2$H$_4$OMe |
| tBu | H | Cl | Cl | C$_3$H$_6$OMe |
| tBu | H | Cl | Cl | CH$_2$Ph |
| tBu | H | nPr | Cl | Me |
| tBu | H | nBu | Cl | Me |
| tBu | H | iBu | Cl | Me |
| tBu | H | sBu | Cl | Me |
| tBu | H | cPr | Cl | Me |
| tBu | H | Ph | Cl | Me |
| tBu | H | F | Cl | Me |
| tBu | H | Br | Cl | Me |
| tBu | H | I | Cl | Me |
| tBu | H | CHF$_2$ | Cl | Me |
| tBu | H | CH$_2$F | Cl | Me |
| tBu | H | CN | Cl | Me |
| tBu | H | NO$_2$ | Cl | Me |
| tBu | H | NMe$_2$ | Cl | Me |
| tBu | H | NEt$_2$ | Cl | Me |
| tBu | H | CO$_2$Me | Cl | Me |
| 1-Me—Bu | H | Me | Cl | Me |
| 1-Me—Bu | H | CF$_3$ | Cl | Me |
| 1-Me—Bu | H | Cl | Cl | Me |
| 1-Me—Pen | H | Me | Cl | Me |
| 1-Me—Pen | H | CF$_3$ | Cl | Me |
| 1-Me—Pen | H | Cl | Cl | Me |
| 1,1-Me$_2$—Pr | H | Me | Cl | Me |
| 1,1-Me$_2$—Pr | H | CF$_3$ | Cl | Me |
| 1,1-Me$_2$—Pr | H | Cl | Cl | Me |
| cPen | H | Me | Cl | Me |
| cPen | H | CF$_3$ | Cl | Me |

TABLE 2

| R$^1$ | Z$^1$ | Z$^2$ | Z$^3$ |
|---|---|---|---|
| Ph | Me | H | H |
| Ph | Me | Cl | H |
| Ph | Me | H | Cl |
| Ph | Et | H | H |
| Ph | nPr | H | H |
| Ph | iPr | H | H |
| Ph | nBu | H | H |
| Ph | iBu | H | H |
| Ph | sBu | H | H |
| Ph | tBu | H | H |
| Ph | F | H | H |
| Ph | Cl | H | H |
| Ph | Cl | Cl | H |
| Ph | Cl | Me | H |
| Ph | Cl | H | Cl |
| Ph | Cl | Br | H |
| Ph | Br | H | H |
| Ph | Br | Br | H |
| Ph | Br | Me | H |
| Ph | I | H | H |
| Ph | OMe | H | H |
| Ph | OPh | H | H |
| Ph | CF$_3$ | H | H |
| Ph | SMe | H | H |
| Ph | SOMe | H | H |
| Ph | SO$_2$Me | H | H |
| Ph | Ph | H | H |
| Ph | CH$_2$Ph | H | H |
| Ph | NO$_2$ | H | H |
| Ph | CN | H | H |
| Ph | COCH$_3$ | H | H |
| Ph | CO$_2$Me | H | H |
| Ph | NMe$_2$ | H | H |
| Ph | H | Cl | H |
| Ph | H | H | Cl |
| 2-Cl—Ph | Cl | H | H |
| 3-Cl—Ph | Cl | H | H |
| 4-Cl—Ph | Cl | H | H |
| 2-F—Ph | Cl | H | H |
| 3-F—Ph | Cl | H | H |
| 4-F—Ph | Cl | H | H |
| 2-Br—Ph | Cl | H | H |
| 3-Br—Ph | Cl | H | H |
| 4-Br—Ph | Cl | H | H |
| 2-Me—Ph | Cl | H | H |
| 3-Me—Ph | Cl | H | H |

TABLE 2-continued

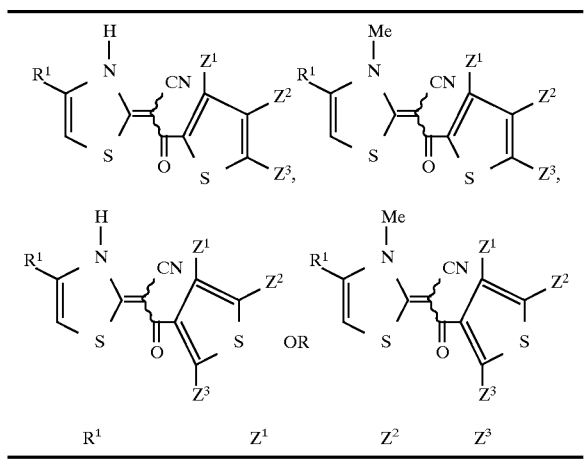

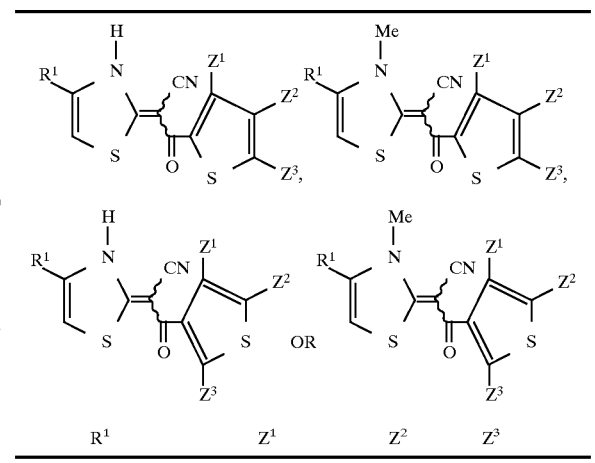

| R¹ | Z¹ | Z² | Z³ |
|---|---|---|---|
| 4-Me—Ph | Cl | H | H |
| 2-CF₃—Ph | Cl | H | H |
| 3-CF₃—Ph | Cl | H | H |
| 4-CF₃—Ph | Cl | H | H |
| 3-tBu—Ph | Cl | H | H |
| 4-tBu—Ph | Cl | H | H |
| 2-MeO—Ph | Cl | H | H |
| 3-MeO—Ph | Cl | H | H |
| 4-MeO—Ph | Cl | H | H |
| 2-CN—Ph | Cl | H | H |
| 3-CN—Ph | Cl | H | H |
| 4-CN—Ph | Cl | H | H |
| 2-NO₂—Ph | Cl | H | H |
| 3-NO₂—Ph | Cl | H | H |
| 4-NO₂—Ph | Cl | H | H |
| 2,3-Cl₂—Ph | Cl | H | H |
| 2,4-Cl₂—Ph | Cl | H | H |
| 2,5-Cl₂—Ph | Cl | H | H |
| 2,6-Cl₂—Ph | Cl | H | H |
| 3,4-Cl₂—Ph | Cl | H | H |
| 3,5-Cl₂—Ph | Cl | H | H |
| 2,3-F₂—Ph | Cl | H | H |
| 2,4-F₂—Ph | Cl | H | H |
| 2,5-F₂—Ph | Cl | H | H |
| 2,6-F₂—Ph | Cl | H | H |
| 3,4-F₂—Ph | Cl | H | H |
| 3,5-F₂—Ph | Cl | H | H |
| H | Cl | H | H |
| Me | Cl | H | H |
| Et | Cl | H | H |
| nPr | Cl | H | H |
| iPr | Cl | H | H |
| cPr | Cl | H | H |
| 1-Me—cPr | Cl | H | H |
| nBu | Cl | H | H |
| iBu | Cl | H | H |
| sBu | Cl | H | H |
| tBu | Me | H | H |
| tBu | Me | Cl | H |
| tBu | Me | H | Cl |
| tBu | Et | H | H |
| tBu | nPr | H | H |
| tBu | iPr | H | H |
| tBu | nBu | H | H |
| tBu | iBu | H | H |
| tBu | sBu | H | H |
| tBu | tBu | H | H |
| tBu | F | H | H |
| tBu | Cl | H | H |
| tBu | Cl | Cl | H |
| tBu | Cl | Me | H |
| tBu | Cl | H | Cl |
| tBu | Br | H | H |
| tBu | Br | Br | H |
| tBu | Br | Me | H |
| tBu | I | H | H |
| tBu | OMe | H | H |
| tBu | OPh | H | H |
| tBu | CF₃ | H | H |
| tBu | SMe | H | H |
| tBu | SOMe | H | H |
| tBu | SO₂Me | H | H |
| tBu | Ph | H | H |
| tBu | CH₂Ph | H | H |
| tBu | NO₂ | H | H |
| tBu | CN | H | H |
| tBu | COCH₃ | H | H |
| tBu | CO₂Me | H | H |
| tBu | NMe₂ | H | H |
| tBu | H | Cl | H |
| tBu | H | H | Cl |
| 1,1-Me₂—Pr | Cl | H | H |
| 1-Me—Bu | Cl | H | H |
| 1-Me—Pen | Cl | H | H |
| cPen | Cl | H | H |
| cHex | Cl | H | H |
| C₂F₅ | Cl | H | H |

TABLE 3

| R¹ | Q | R⁴ | Y |
|---|---|---|---|
| Ph | Q₁ | H | — |
| 2-Cl—Ph | Q₁ | Me | 2-Cl |
| 2-F—Ph | Q₁ | Et | 2-Br |
| 2-Me—Ph | Q₂ | nPr | — |
| 2,6-F₂—Ph | Q₃ | iPr | 2,5-Me₂ |
| 2,6-Cl₂—Ph | Q₃ | nBu | 2-Cl-3-Cl-4-CN-5-Ph |
| tBu | Q₃ | iBu | 2-CF₃-3-Br-4-CN-5-Ph |
| cHex | Q₃ | sBu | — |
| Ph | Q₄ | tBu | 1-EtOCH₂ |
| 2-Cl—Ph | Q₄ | CF₃ | 1-MeOCH₂-3,4-Br₂-5-Ph |
| 2-F—Ph | Q₅ | MeOCH₂ | 1-Me |
| 2-Me—Ph | Q₅ | EtOCH₂ | 1-EtOCH₂-2-Ph-5-Br |
| 2,6-F₂—Ph | Q₆ | MeC(=O) | — |
| 2,6-Cl₂—Ph | Q₆ | EtC(=O) | 4-Me-5-Cl |
| tBu | Q₆ | EtO₂C | 4-Ph |
| cHex | Q₇ | Ph | — |
| Ph | Q₇ | PhCH₂ | 2-Ph-5-Br |
| 2-Cl—Ph | Q₇ | H | 5-Me |
| 2-F—Ph | Q₈ | H | 2,4-Me₂ |
| 2-Me—Ph | Q₈ | H | 4-Cl |
| 2,6-F₂—Ph | Q₈ | H | 4-COOEt |
| Ph | Q₈ | H | 4-Me |

TABLE 3-continued

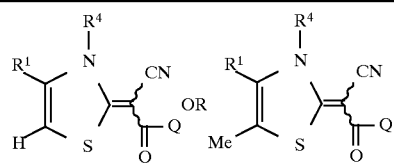 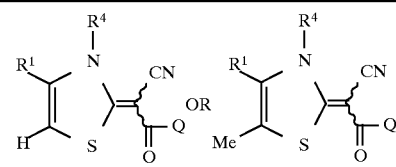

| R¹ | Q | R⁴ | Y |
|---|---|---|---|
| 2-Cl—Ph | $Q_8$ | H | 4-Me-5-Cl |
| 2-F—Ph | $Q_8$ | H | 5-Br |
| 2-Me—Ph | $Q_9$ | H | — |
| 2,6-F$_2$—Ph | $Q_9$ | H | 4-Me |
| 2,6-Cl$_2$—Ph | $Q_9$ | H | 4,5-Me |
| tBu | $Q_{10}$ | H | 2-CF$_3$-5-Me |
| cHex | $Q_{10}$ | H | 2-CF$_3$-5-Cl |
| 1-naphthyl | $Q_{10}$ | H | — |
| 2-pyridinyl | $Q_{10}$ | H | 5-MeO |
| Ph | $Q_{10}$ | H | 5-Cl |
| 2-Cl—Ph | $Q_{10}$ | H | 2-Me |
| 2-F—Ph | $Q_{10}$ | H | 2,5-Me |
| 2-Me—Ph | $Q_{10}$ | H | 2-CF$_3$-5-Me |
| 2,6-F$_2$—Ph | $Q_{10}$ | H | 2-CF$_3$-5-Cl |
| 2,6-Cl$_2$—Ph | $Q_{10}$ | H | — |
| tBu | $Q_{10}$ | H | 5-MeO |
| cHex | $Q_{10}$ | H | 5-Cl |
| 1-naphthyl | $Q_{10}$ | H | 2-MeS-5-Cl |
| 2-pyridinyl | $Q_{10}$ | H | 5-MeO |
| Ph | $Q_{10}$ | H | 5-Cl |
| 2-Cl—Ph | $Q_{11}$ | H | 2-Me-4-CF$_3$ |
| 2-F—Ph | $Q_{11}$ | H | 4-MeO |
| 2-Me—Ph | $Q_{11}$ | H | 2-Et-4-CF$_3$ |
| 2,6-F$_2$—Ph | $Q_{11}$ | H | 4-Cl |
| 2,6-Cl$_2$—Ph | $Q_{11}$ | H | 2,4-(CF$_3$)$_2$ |
| tBu | $Q_{11}$ | H | 4-Me |
| cHex | $Q_{11}$ | H | 2-Me-4-CF$_3$ |
| 1-naphthyl | $Q_{11}$ | H | 2-Me-4-CF$_3$ |
| 2-pyridinyl | $Q_{11}$ | H | 2-Me-4-CF$_3$ |
| Ph | $Q_{11}$ | H | 2-Me-4-CF$_3$ |
| 2-Cl—Ph | $Q_{11}$ | H | 2,4-Me$_2$ |
| 2-F—Ph | $Q_{11}$ | H | 2,4-Me$_2$ |
| 2-Me—Ph | $Q_{11}$ | H | 2,4-Me$_2$ |
| 2,6-F$_2$—Ph | $Q_{11}$ | H | 2,4-Me$_2$ |
| 2,6-Cl$_2$—Ph | $Q_{11}$ | H | 2-Me-4-CF$_3$ |
| tBu | $Q_{11}$ | H | 4-MeO |
| cHex | $Q_{11}$ | H | 2-Et-4-CF$_3$ |
| 1-naphthyl | $Q_{11}$ | H | 4-Cl |
| 2-pyridinyl | $Q_{11}$ | H | 2,4-(CF$_3$)$_2$ |
| Ph | $Q_{11}$ | H | 4-Me |
| 2-Cl—Ph | $Q_{11}$ | H | 4-iPr |
| 2-F—Ph | $Q_{12}$ | H | 2,5-Me$_2$ |
| 2-Me—Ph | $Q_{12}$ | H | 2,4,5-Cl$_3$ |
| 2,6-F$_2$—Ph | $Q_{12}$ | H | 2-CF$_3$-5-Me |
| 2,6-Cl$_2$—Ph | $Q_{12}$ | H | 2-Cl-5-Me |
| tBu | $Q_{13}$ | H | 5-Me |
| cHex | $Q_{13}$ | H | 2-CF$_3$-5-Me |
| 1-naphthyl | $Q_{14}$ | H | 1,4-Me$_2$ |
| 2-pyridinyl | $Q_{14}$ | H | 1,4-Me$_2$ |
| Ph | $Q_{14}$ | H | 1,4-Me$_2$ |
| 2-Cl—Ph | $Q_{14}$ | H | 1-CF$_3$-4-Me |
| 2-F—Ph | $Q_{15}$ | H | — |
| 2-Me—Ph | $Q_{15}$ | H | 4-Me |
| 2,6-F$_2$—Ph | $Q_{15}$ | H | 4,5-Me$_2$ |
| 2,6-Cl$_2$—Ph | $Q_{16}$ | H | 3,5-Me$_2$ |
| tBu | $Q_{16}$ | H | 5-COOMe |
| cHex | $Q_{16}$ | H | 3,5-Cl$_2$ |
| 1-naphthyl | $Q_{17}$ | H | 4-Me |
| Ph | $Q_{17}$ | H | 4—Ph |
| 2-Cl—Ph | $Q_{17}$ | H | 4-MeC(=O) |
| 2-F—Ph | $Q_{18}$ | H | — |
| 2-Me—Ph | $Q_{18}$ | H | 4-Me |
| 2,6-F$_2$—Ph | $Q_{19}$ | H | 3,5-Me$_2$ |
| 2,6-Cl$_2$—Ph | $Q_{19}$ | H | 3,5-Cl$_2$ |
| tBu | $Q_{20}$ | H | — |
| cHex | $Q_{20}$ | H | — |
| 1-naphthyl | $Q_{21}$ | H | — |
| 2-pyridinyl | $Q_{21}$ | H | 3,5-Me$_2$ |
| Ph | $Q_{21}$ | H | 3,5-Cl$_2$ |
| 2-Cl—Ph | $Q_{21}$ | H | 3-CF$_3$ |
| 2-F—Ph | $Q_{21}$ | H | 3-CF$_3$-5-Cl |
| 2-Me—Ph | $Q_{21}$ | H | 3,5-Me$_2$ |
| 2,6-F$_2$—Ph | $Q_{21}$ | H | 3,5-Cl$_2$ |
| 2,6-Cl$_2$—Ph | $Q_{21}$ | H | 3-CF$_3$ |
| tBu | $Q_{21}$ | H | 3-CF$_3$-5-Cl |
| cHex | $Q_{21}$ | H | 3,5-Me$_2$ |
| 1-naphthyl | $Q_{21}$ | H | 3,5-Cl$_2$ |
| 2-pyridinyl | $Q_{21}$ | H | 3-CF$_3$ |
| Ph | $Q_{21}$ | H | 3-CF$_3$-5-Cl |
| 2-Cl—Ph | $Q_{21}$ | H | 3,5-Me$_2$ |
| 2-F—Ph | $Q_{21}$ | H | 3,5-Cl$_2$ |
| 2-Me—Ph | $Q_{21}$ | H | 3-CF$_3$ |
| 2,6-F$_2$—Ph | $Q_{21}$ | H | 3-CF$_3$-5-Cl |
| 2,6-Cl$_2$—Ph | $Q_{21}$ | H | 3-CF$_3$-4-NO$_2$-5-Cl |
| tBu | $Q_{21}$ | H | 3-Me-4-NO$_2$-5-MeO |
| cHex | $Q_{21}$ | H | 3,5-Cl$_2$-4-CN |
| 1-naphthyl | $Q_{21}$ | H | 3-Br-4-CN-5-COOEt |
| Ph | $Q_{21}$ | H | 3-Me-4-COOMe-5-MeS |
| 2-Cl—Ph | $Q_{21}$ | H | 3-Me-4-F-5-EtSO |
| 2-F—Ph | $Q_{21}$ | H | 3-Me-4-Cl-5-nBuSO$_2$ |
| 2-Me—Ph | $Q_{22}$ | H | 5-Me |
| 2,6-F$_2$—Ph | $Q_{22}$ | H | 5-nPr |
| 2,6-Cl$_2$—Ph | $Q_{22}$ | H | 5-CF$_3$ |
| tBu | $Q_{22}$ | H | 5-C$_2$F$_5$ |
| cHex | $Q_{22}$ | H | 5-MeO |
| 1-naphthyl | $Q_{23}$ | H | 5-Me |
| 2-pyridinyl | $Q_{23}$ | H | 5-nPr |
| Ph | $Q_{23}$ | H | 5-CF$_3$ |
| 2-Cl—Ph | $Q_{23}$ | H | 5-CF$_3$CF$_2$CF$_2$ |
| 2-F—Ph | $Q_{23}$ | H | 5-EtO |
| 2-Me—Ph | $Q_{24}$ | H | 2,5-Me$_2$ |
| 2,6-F$_2$—Ph | $Q_{24}$ | H | 2-CF$_3$-5-Cl |
| 2,6-Cl$_2$—Ph | $Q_{24}$ | H | 2,5-Me$_2$ |
| tBu | $Q_{24}$ | H | 2-CF$_3$-5-Cl |
| cHex | $Q_{24}$ | H | 2-Me$_2$N |
| 1-naphthyl | $Q_{25}$ | H | 1-Me |
| 2-pyridinyl | $Q_{25}$ | H | 1,5-Me$_2$ |
| Ph | $Q_{25}$ | H | 1-Me |
| 2-Cl—Ph | $Q_{26}$ | H | 5-Me |
| 2-F—Ph | $Q_{26}$ | H | 5-CF$_3$ |
| 2-Me—Ph | $Q_{27}$ | H | 2-Et |
| 2,6-F$_2$—Ph | $Q_{27}$ | H | 2-nPrS |
| 2,6-Cl$_2$—Ph | $Q_{27}$ | H | 2-tBu |
| tBu | $Q_{28}$ | H | 5-CF$_3$ |
| cHex | $Q_{29}$ | H | 2-Me |
| 1-naphthyl | $Q_{29}$ | H | 2—PhCH$_2$ |
| Ph | $Q_{30}$ | H | 5-MeO |
| 2-Cl—Ph | $Q_{30}$ | H | 5-MeS |
| 2-F—Ph | $Q_{30}$ | H | 5-CF$_3$ |
| 2-Me—Ph | $Q_{30}$ | H | 5-Cl |
| 2,6-F$_2$—Ph | $Q_{31}$ | H | 1-Me-5-iPrS |
| 2,6-Cl$_2$—Ph | $Q_{32}$ | H | 1-Me |
| tBu | $Q_{33}$ | H | 5-Me |
| cHex | $Q_{33}$ | H | 5-Ph |
| 1-naphthyl | $Q_{34}$ | H | — |
| 2-pyridinyl | $Q_{34}$ | H | 4-Me |
| Ph | $Q_{34}$ | H | 4-CF$_3$ |
| 2-Cl—Ph | $Q_{35}$ | H | 5-Me |
| 2-F—Ph | $Q_{36}$ | H | 1-Me |
| 2-Me—Ph | $Q_{37}$ | H | 3-Cl |
| 2,6-F$_2$—Ph | $Q_{37}$ | H | 3-Br |
| 2,6-Cl$_2$—Ph | $Q_{37}$ | H | — |
| tBu | $Q_{37}$ | H | 3-Cl |
| cHex | $Q_{37}$ | H | 3-Br |
| 1-naphthyl | $Q_{37}$ | H | — |
| 2-pyridinyl | $Q_{37}$ | H | 3-Cl |

TABLE 3-continued

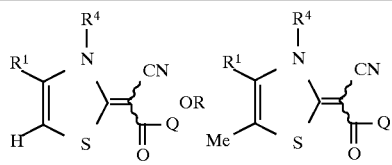 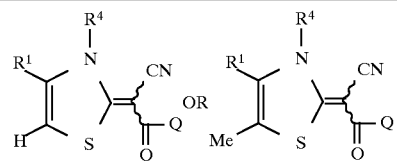

| R¹ | Q | R⁴ | Y |
|---|---|---|---|
| Ph | $Q_{38}$ | H | 2-Me |
| 2-Cl—Ph | $Q_{38}$ | H | 2-Me |
| 2-F—Ph | $Q_{38}$ | H | 2-Me |
| 2-Me—Ph | $Q_{38}$ | H | 2-Me |
| 2,6-F$_2$—Ph | $Q_{38}$ | H | 2-Me |
| 2,6-Cl$_2$—Ph | $Q_{38}$ | H | 2-Me |
| tBu | $Q_{38}$ | H | 2-Me |
| cHex | $Q_{38}$ | H | 2-Me |
| 1-naphthyl | $Q_{38}$ | H | 2-Me |
| 2-pyridinyl | $Q_{38}$ | H | 2-Me |
| Ph | $Q_{38}$ | H | 2-Cl |
| 2-Cl—Ph | $Q_{38}$ | H | 2-Cl |
| 2-F—Ph | $Q_{38}$ | H | 2-Cl |
| 2-Me—Ph | $Q_{38}$ | H | 2-Cl |
| 2,6-F$_2$—Ph | $Q_{38}$ | H | 2-Cl |
| 2,6-Cl$_2$—Ph | $Q_{38}$ | H | 2-Cl |
| tBu | $Q_{38}$ | H | 2-Cl |
| cHex | $Q_{38}$ | H | 2-Cl |
| 1-naphthyl | $Q_{38}$ | H | 2-Cl |
| 2-pyridinyl | $Q_{38}$ | H | 2-Cl |
| Ph | $Q_{38}$ | H | 2-Br |
| 2-Cl—Ph | $Q_{38}$ | H | 2-Br |
| 2-F—Ph | $Q_{38}$ | H | 2-Br |
| 2-Me—Ph | $Q_{38}$ | H | 2-Br |
| 2,6-F$_2$—Ph | $Q_{38}$ | H | 2-Br |
| 2,6-Cl$_2$—Ph | $Q_{38}$ | H | 2-I |
| tBu | $Q_{38}$ | H | 2-I |
| cHex | $Q_{38}$ | H | 2-I |
| 1-naphthyl | $Q_{38}$ | H | 2-I |
| 2-pyridinyl | $Q_{38}$ | H | 2-I |
| Ph | $Q_{38}$ | H | 2-MeO |
| 2-Cl—Ph | $Q_{38}$ | H | 2-MeO |
| 2-F—Ph | $Q_{38}$ | H | 2-MeO |
| 2-Me—Ph | $Q_{38}$ | H | 2-MeO |
| 2,6-F$_2$—Ph | $Q_{38}$ | H | 2-MeO |
| 2,6-Cl$_2$—Ph | $Q_{38}$ | H | 2-MeO |
| tBu | $Q_{38}$ | H | 2-MeO |
| cHex | $Q_{38}$ | H | 2-MeO |
| 1-naphthyl | $Q_{38}$ | H | 2-MeO |
| 2-pyridinyl | $Q_{38}$ | H | 2-MeO |
| Ph | $Q_{38}$ | H | 2-EtO |
| 2-Cl—Ph | $Q_{38}$ | H | 2-EtO |
| 2-F—Ph | $Q_{38}$ | H | 2-nPrO |
| 2-Me—Ph | $Q_{38}$ | R | 2-nPrO |
| 2,6-F$_2$—Ph | $Q_{38}$ | H | 2-iPrO |
| 2,6-Cl$_2$—Ph | $Q_{38}$ | H | 2-CF$_3$ |
| tBu | $Q_{38}$ | H | 2-CF$_3$ |
| cHex | $Q_{38}$ | H | 2-CF$_3$ |
| 1-naphthyl | $Q_{38}$ | H | 2-CF$_3$ |
| 2-pyridinyl | $Q_{38}$ | H | 2-CF$_3$ |
| Ph | $Q_{38}$ | H | 2-MeS |
| 2-Cl—Ph | $Q_{38}$ | H | 2-MeS |
| 2-F—Ph | $Q_{38}$ | H | 2-MeS |
| 2-Me—Ph | $Q_{38}$ | H | 2-MeS |
| 2,6-F$_2$—Ph | $Q_{38}$ | H | 2-MeS |
| 2,6-Cl$_2$—Ph | $Q_{38}$ | H | 2-MeS |
| tBu | $Q_{38}$ | H | 2-MeS |
| cHex | $Q_{38}$ | H | 2-MeS |
| 1-naphthyl | $Q_{38}$ | H | 2-MeS |
| 2-pyridinyl | $Q_{38}$ | H | 2-MeS |
| Ph | $Q_{38}$ | H | 2-MeSO |
| 2-Cl—Ph | $Q_{38}$ | H | 2-MeSO |
| 2-F—Ph | $Q_{38}$ | H | 2-MeSO |
| 2-Me—Ph | $Q_{38}$ | H | 2-MeSO$_2$ |
| 2,6-F$_2$—Ph | $Q_{38}$ | H | 2-MeSO$_2$ |
| 2,6-Cl$_2$—Ph | $Q_{38}$ | H | 2-MeSO$_2$ |
| tBu | $Q_{38}$ | H | 2-MeSO$_2$ |
| cHex | $Q_{38}$ | H | 2-MeSO$_2$ |
| 1-naphthyl | $Q_{38}$ | H | 2-MeSO$_2$ |
| 2-pyridinyl | $Q_{38}$ | H | 2-MeSO$_2$ |
| Ph | $Q_{38}$ | H | 2-EtS |
| 2-Cl—Ph | $Q_{38}$ | H | 2-EtSO |
| 2-F—Ph | $Q_{38}$ | H | 2-EtSO$_2$ |
| 2-Me—Ph | $Q_{38}$ | H | 2-nBuS |
| 2,6-F$_2$—Ph | $Q_{38}$ | H | 2-NO$_2$ |
| 2,6-Cl$_2$—Ph | $Q_{38}$ | H | 2-NO$_2$ |
| tBu | $Q_{38}$ | H | 2-NO$_2$ |
| cHex | $Q_{38}$ | H | 2-NO$_2$ |
| 1-naphthyl | $Q_{38}$ | H | 2-CF$_3$ |
| 2-pyridinyl | $Q_{38}$ | H | 2-CF$_3$ |
| Ph | $Q_{38}$ | H | 4-Cl |
| 2-Cl—Ph | $Q_{38}$ | H | 4-Cl |
| 2-F—Ph | $Q_{38}$ | H | 4-Cl |
| 2-Me—Ph | $Q_{38}$ | H | 4-Cl |
| 2,6-F$_2$—Ph | $Q_{38}$ | H | 4-Cl |
| 2,6-Cl$_2$—Ph | $Q_{38}$ | H | 4-Cl |
| tBu | $Q_{38}$ | H | 4-Cl |
| cHex | $Q_{38}$ | H | 4-Cl |
| 1-naphthyl | $Q_{38}$ | H | 4-Cl |
| 2-pyridinyl | $Q_{38}$ | H | 4-Cl |
| Ph | $Q_{38}$ | H | 4-COOMe |
| 2-Cl—Ph | $Q_{38}$ | H | 4-COOMe |
| 2-F—Ph | $Q_{38}$ | H | 4-COOMe |
| 2-Me—Ph | $Q_{38}$ | H | 4-COOMe |
| 2,6-F$_2$—Ph | $Q_{38}$ | H | 4-COOMe |
| 2,6-Cl$_2$—Ph | $Q_{38}$ | H | 4-COOMe |
| tBu | $Q_{38}$ | H | 4-COOEt |
| cHex | $Q_{38}$ | H | 4-COOEt |
| 1-naphthyl | $Q_{38}$ | H | 4-COOEt |
| 2-pyridinyl | $Q_{38}$ | H | 4-COOEt |
| Ph | $Q_{38}$ | H | 6-Cl |
| 2-Cl—Ph | $Q_{38}$ | H | 6-Br |
| 2-F—Ph | $Q_{38}$ | H | 6-I |
| 2-Me—Ph | $Q_{38}$ | H | 6-Me |
| 2,6-F$_2$—Ph | $Q_{38}$ | H | 4-Cl-6-CF$_3$ |
| 2,6-Cl$_2$—Ph | $Q_{38}$ | H | 4-Cl-6-CF$_3$ |
| tBu | $Q_{38}$ | H | 4-Cl-6-CF$_3$ |
| cHex | $Q_{38}$ | H | 4-Cl-6-CF$_3$ |
| 1-naphthyl | $Q_{38}$ | H | 4-Cl-6-CF$_3$ |
| 2-pyridinyl | $Q_{38}$ | H | 4-Cl-6-CF$_3$ |
| Ph | $Q_{39}$ | H | 3-Cl |
| 2-Cl—Ph | $Q_{39}$ | H | 3,5-Cl$_2$ |
| 2-F—Ph | $Q_{39}$ | H | — |
| 2-Me—Ph | $Q_{39}$ | H | — |
| 2,6-F$_2$—Ph | $Q_{39}$ | H | — |
| 2,6-Cl$_2$—Ph | $Q_{39}$ | H | — |
| tBu | $Q_{39}$ | H | |
| cHex | $Q_{39}$ | H | |
| 1-naphthyl | $Q_{40}$ | H | — |
| 2-pyridinyl | $Q_{40}$ | H | — |
| Ph | $Q_{40}$ | H | — |
| 2-Cl—Ph | $Q_{41}$ | H | — |
| 2-F—Ph | $Q_{41}$ | H | 4,5-Me$_2$ |
| 2-Me—Ph | $Q_{41}$ | H | 4-Cl |
| 2,6-F$_2$—Ph | $Q_{41}$ | H | 4,5-Cl$_2$ |
| 2,6-Cl$_2$—Ph | $Q_{42}$ | H | — |
| tBu | $Q_{43}$ | H | 4,6-Cl$_2$ |
| cHex | $Q_{43}$ | H | 4,6-(MeO)$_2$ |
| 1-naphthyl | $Q_{43}$ | H | — |
| 2-pyridinyl | $Q_{44}$ | H | |
| Ph | $Q_{45}$ | H | 6-Me |
| 2-Cl—Ph | $Q_{45}$ | H | 6-Cl |
| 2-F—Ph | $Q_{45}$ | H | 6-MeS |
| 2-Me—Ph | $Q_{46}$ | H | 6-Me |
| 2,6-F$_2$—Ph | $Q_{46}$ | H | 6-Cl |
| 2,6-Cl$_2$—Ph | $Q_{46}$ | H | 6-MeS |

TABLE 3-continued

[Structures shown:
$R^1\text{-}N(R^4)\text{...CN, OR, Q}$ with H, S, C=O, Q
or with Me, S, C=O, Q]

| $R^1$ | Q | $R^4$ | Y |
|---|---|---|---|
| tBu | $Q_{47}$ | H | 3-Me-5-Ph |
| cHex | $Q_{47}$ | H | 3-Et-5-Ph |
| 1-naphthyl | $Q_{48}$ | H | 5-Ph |
| 2-pyridinyl | $Q_{49}$ | H | — |
| Ph | $Q_{50}$ | H | — |
| 2-Cl—Ph | $Q_{51}$ | H | — |
| 2-F—Ph | $Q_{52}$ | H | — |
| 2-Me—Ph | $Q_{53}$ | H | — |
| 2,6-$F_2$—Ph | $Q_{54}$ | H | — |
| 2,6-$Cl_2$—Ph | $Q_{55}$ | H | — |
| tBu | $Q_{56}$ | H | — |
| cHex | $Q_{57}$ | H | — |
| 1-naphthyl | $Q_{58}$ | H | — |
| 2-pyridinyl | $Q_{59}$ | H | — |
| Ph | $Q_{60}$ | H | — |
| 2-Cl—Ph | $Q_{61}$ | H | — |
| 2-F—Ph | $Q_{62}$ | H | — |
| 2-Me—Ph | $Q_{63}$ | H | — |
| 2,6-$F_2$—Ph | $Q_{64}$ | H | — |
| 2,6-$Cl_2$—Ph | $Q_{65}$ | H | — |
| tBu | $Q_{66}$ | H | — |
| cHex | $Q_{67}$ | H | — |
| 1-naphthyl | $Q_{68}$ | H | — |
| 2-pyridinyl | $Q_{69}$ | H | — |
| Ph | $Q_{69}$ | H | 4,5-$Cl_2$ |
| 2-Cl—Ph | $Q_{69}$ | H | 4,5-$Br_2$ |
| 2-F—Ph | $Q_{70}$ | H | 2-Me-5-Cl |
| 2-Me—Ph | $Q_{70}$ | H | 2-Me-5-Br |
| 2,6-$F_2$—Ph | $Q_{71}$ | H | 4-Cl |
| 2,6-$Cl_2$—Ph | $Q_{71}$ | H | 4-Me |
| tBu | $Q_{71}$ | H | 4-Br |
| cHex | $Q_{72}$ | H | 4,5-$Cl_2$ |
| 1-naphthyl | $Q_{73}$ | H | — |
| 2-pyridinyl | $Q_{73}$ | H | 4,5-$Cl_2$ |
| Ph | $Q_{73}$ | H | 4-$NO_2$ |

When the compound of the present invention is utilized as a vermin controlling agent, in general, it may be mixed for application with a suitable carrier including solid carriers such as clays, talcs, bentonites, diatomaceous earths, and white carbon; and liquid carriers, for example water; alcohols such as isopropanol, butanol, benzyl alcohol and furfuryl alcohol; aromatic hydrocarbons such as toluene and xylene; ethers such as anisole; ketones such as cyclohexanone and isophorone; esters such as butyl acetate; acid amides such as N-methylpyrrolidone; and halogenated hydrocarbons such as chlorobenzene, and it may be put to practical use in an optional dosage form including solutions, emulsions, hydrates, dry flowables, flowables, powders and granules by addition of surfactants, emulsifiers, dispersers, penetrants, spreaders, viscosity-increasing agents, antifreezes, solidification protectors, stabilizers and the like if desired.

Additionally, the compound of the present invention may be mixed for application with the other herbicides, varieties of insecticides, acaricides, nematicides, bactericides, plant-growth improving agents, synergists, fertilizers, soil improving agents and the like in manufacturing the preparations or in spreading as occasion demands.

Especially, the admixture with other agricultural chemicals or plant hormones may be expected to bring about a lowering of the cost by a decrease in the dosage used, enlargement of insecticidal spectra by the synergetic effect of the mixed agents, and a higher effect to control noxious organisms. In this case, simultaneous combinations with plural known agricultural chemicals are possible. The agricultural chemicals used in mixing with the compound of the present invention are exemplified by the compounds described in Farm Chemicals Handbook, 1994.

The dosage of the compound of the present invention used depends upon the place to be applied, the time to be used, the method of using, the cultivated crop and the like, and in general, however, it may suitably be from approximately 0.005 to 50 kg per hectare (ha) as the dosage of active ingredient.

The followings are the compounding examples of the preparations using the compound of the present invention, but are not to be construed to limit the invention to the examples. In the following examples, "part(s)" means "part (s) by weight.

[Wettable powder]
 Compound of the invention 5 to 80 parts
 Solid carrier 10 to 85 parts
 Surfactant 1 to 10 parts
 Others 1 to 5 parts
 The others include, for example, solidification protectors.

[Emulsifiable concentrate]
 Compound of the invention 1 to 30 parts
 Liquid carrier 30 to 95 parts
 Surfactant 5 to 15 parts

[Flowable]
 Compound of the invention 5 to 70 parts
 Liquid carrier 15 to 65 parts
 Surfactant 5 to 12 parts
 Others 5 to 30 parts
 The others include, for example, antifreezes and viscosity-increasing agents.

[Water dispersible granule (Dry Flowable)]
 Compound of the invention 20 to 90 parts
 Solid carrier 10 to 60 parts
 Surfactant 1 to 20 parts

[Granule]
 Compound of the invention 0.1 to 10 parts
 Solid carrier 90 to 99.99 parts
 Others 1 to 5 parts

[Dustable powder]
 Compound of the invention 0.01 to 30 parts
 Solid carrier 67 to 99.5 parts
 Others 0 to 3 parts

BEST MODE FOR CARRYING OUT THE INVENTION

In the following, detailed descriptions of the synthesis, preparation and test examples of the compound of the present invention are provided, but are not to be construed to limit the invention.

[Synthesis Example 1]
 Synthesis of 3-(1-methyl-3,5-dichloropyrazol-4-yl)-2-(4-phenyl-2,3-dihydrothiazol-2-ylidene)-3-oxopropionitrile (Compound No. 3)

In 2 ml of xylene was dissolved 0.8 g of 2-cyanomethyl-4-phenylthiazole, and the resulting solution was mixed with 40 mg of 4-dimethylaminopyridine. After adding 0.85 g of 1-methyl-3,5-dichloropyrazole-4-carbonyl chloride at room temperature, the resulting mixture was heated under reflux for 3 hours. After evaporating the xylene under reduced pressure, 3 ml of methanol was added, and the resulting mixture was heated under reflux for 10 minutes. The solvent was evaporated under reduced pressure and the residue was recrystallized from acetonitrile to give 0.68 g of the objective.

[Synthesis Example 2]

Synthesis of 3-(1-methyl-3,5-dichloropyrazol-4-yl)-2-(4-tert-butyl-2,3-dihydrothiazol-2-ylidene)-3-oxopropionitrile (Compound No. 9)

In 10 ml of benzene was dissolved 0.8 g of 2-cyanomethyl-4-tert-butylthiazole, and 0.11 g of 4-dimethylaminopyridine and 0.45 g of triethylamine were added to the resulting solution.

After adding 0.95 g of 1-methyl-3,5-dichloropyrazole-4-carbonyl chloride, the resulting mixture was stirred at room temperature for 3 days. After evaporating the benzene under reduced pressure, 3 ml of methanol was added, and the resulting mixture was heated under reflux for 10 minutes. After cooling, the reaction mixture was poured into ice-cold water and extracted with ethyl acetate, the ethyl acetate solution was washed with water and dried over anhydrous sodium sulfate, and the solvent was evaporated. The residue obtained was recrystallized from a mixed solvent of acetonitrile and diethyl ether to give 0.5 g of the objective.

[Synthesis Example 3]

Synthesis of 3-(1-methyl-3,5-dichloropyrazol-4-yl)-2-(4-phenyl-3-methylthiazol-2-ylidene)-3-oxopropionitrile (Compound No. 8)

In 5 ml of ethanol was dissolved 0.3 g of 3-methylamino-3-mercapto-2-(1-methyl-3,5-dichloro-4-pyrazolylcarbonyl)acrylonitrile, and 0.056 g of sodium methoxide was added at room temperature, and then the resulting mixture was stirred for 1 hour. Additionally, 0.205 g of phenacyl bromide was added and the mixture was stirred at room temperature overnight. The reaction mixture was poured into ice-cold water and extracted with ethyl acetate, the ethyl acetate solution was washed with water and dried over anhydrous sodium sulfate, and the solvent was evaporated. The residue obtained was dissolved in 10 ml of toluene, 20 mg of p-toluenesulfonic acid was added to it, and the resulting solution was stirred at 80° C. for 1 hour. After cooling, the reaction mixture was poured into ice-cold water and extracted with ethyl acetate, the ethyl acetate solution was washed with water and dried over anhydrous sodium sulfate, and the solvent was evaporated to give 0.27 g of the objective as a pale yellow solid.

[Synthesis Example 4]

Synthesis of 2-{4-(2,6-difluorophenyl)-2,3-dihydrothiazol-2-ylidene}-3-(4-trifluoromethylpyrimidin-5-yl)-3-oxopropionitrile (Compound No. 137)

In 20 ml of absolute tetrahydrofuran were dissolved 0.58 g of 2-cyanomethyl-4-(2,6-difluorophenyl)thiazole and 0.62 g of 5-(1-pyrazolylcarbonyl-4-trifluoromethylpyrimidine, and 0.22 g of 55% sodium hydride in limited amounts was added with ice-water cooling. After the end of bubbling up, the mixture was stirred at room temperature overnight. The reaction mixture was poured into ice-cold water, adjusted to pH 4 with diluted hydrochloric acid, and extracted with ethyl acetate, and the ethyl acetate solution was washed with a saturated sodium chloride solution, aqueous sodium hydrogencarbonate and saturated sodium chloride solution again, and dried over anhydrous sodium carbonate. The ethyl acetate was evaporated under reduced pressure, and the residue obtained was separated by TLC (ethyl acetate) to give 0.75 g of the objective.

[Synthesis Example 5]

Synthesis of 2-{4-(2,6-difluorophenyl)-2,3-dihydrothiazol-2-ylidene}-3-(3,5-dimethylpyrazol-1-yl)-3-oxopropionitrile (Compound No. 128)

To 2 g of 2-cyanomethyl-4-(2,6-difluorophenyl)thiazole and 4.8 g of dimethyl carbonate was added 30 ml of toluene, 0.6 g of sodium methoxide was added, and the resulting mixture was stirred and heated to the reflux temperature for 4 hours. After cooling, the reaction mixture was poured into 100 ml of ice-cold water, 1N-HCl was added to acidify the aqueous layer, and the mixture was extracted with ethyl acetate. The organic layer was washed with water and dried over anhydrous sodium sulfate, and the solvent was evaporated under reduced pressure, and the residue obtained was purified by column chromatography (ethyl acetate/n-hexane=2/1) to give 1.67 g of methyl 2-cyano-2-{4-(2,6-difluorophenyl)thiazol-2-yl}acetate.

To 0.4 g of methyl 2-cyano-2-{4-(2,6-difluorophenyl)thiazol-2-yl}acetate and 0.4 g of 3,5-dimethylpyrazole was added 10 ml of toluene, and the resulting mixture was stirred and heated to the reflux temperature for 36 hours. After cooling, the reaction mixture was poured into ice-cold water and extracted with ethyl acetate. The organic layer was washed with a saturated sodium chloride solution and dried over anhydrous sodium sulfate, the solvent was evaporated under reduced pressure, and the resulting solid was recrystallized from acetonitrile, and then from ethyl acetate to give 0.13 g of the title objective having a melting point of 219.0° to 224.0° C.

The structures and melting points of the compounds of the present invention synthesized by applying said scheme or examples will be shown in the table 4 to 7. The abbreviations in the tables have the same meanings as those in the table 1 to 3.

TABLE 4

| compound No. | $R^1$ | $R^2$ | $R^4$ | $Y^1$ | $Y^2$ | $Y^3$ | M.p. (°C.) |
|---|---|---|---|---|---|---|---|
| 1 | Ph | H | H | H | Cl | Me | 234–237 |
| 2 | Ph | H | H | H | S-tBu | Me | 165–167 |
| 3 | Ph | H | H | Cl | Cl | Me | 220–222 |
| 4 | Ph | H | H | Cl | S-tBu | Me | 180–182.5 |
| 5 | Ph | H | H | Ph | Ph | Me | 199–201 |
| 6 | Ph | H | H | $CF_8$ | Cl | Me | 174–178 |
| 7 | Ph | H | H | t-Bu | Cl | Me | 215–219 |
| 8 | Ph | H | Me | Cl | Cl | Me | 225–228 |
| 9 | t-Bu | H | H | Cl | Cl | Me | 184–186 |
| 10 | t-Bu | H | H | Ph | Cl | Me | 193–196 |
| 11 | t-Bu | H | H | $CF_8$ | Cl | Me | 227–230 |
| 12 | t-Bu | H | H | $CF_8$ | Cl | Ph | 89–91 |

M.P. = Melting Point

TABLE 5

| compound No. | R¹ | R² | R⁴ | Y⁴ | Y⁵ | Y⁶ | M.P. (°C.) |
|---|---|---|---|---|---|---|---|
| 13 | Ph | H | H | H | H | Et | 199–201 |
| 14 | Ph | H | H | H | H | i-Pro | 199–201 |
| 15 | Ph | H | H | H | Me | Me | 178–180 |
| 16 | Ph | H | H | H | Me | Et | 184–186 |
| 17 | Ph | H | H | Me | H | Me | 171–173 |
| 18 | Ph | H | H | Me | H | i-Pro | 181–183 |
| 19 | Ph | H | H | Me | Cl | Me | 217–222 |
| 20 | Ph | H | H | Me | Cl | i-Pro | 178–182 |
| 21 | Ph | H | H | Me | Br | Me | 204–208 |
| 22 | Ph | H | H | Et | Cl | Me | 245–248 |
| 23 | t-Bu | H | H | H | H | Et | 157.5–159.5 |
| 24 | t-Bu | H | H | H | H | i-Pro | 158.5–160.3 |
| 25 | t-Bu | H | H | H | Me | Me | 156–159 |
| 26 | t-Bu | H | H | H | Me | Et | 161.4–162.7 |
| 27 | t-Bu | H | H | Me | Cl | Me | 186–188.5 |

TABLE 6

| compound No. | R¹ | R² | R⁴ | Z¹ | Z² | Z³ | M.P. (°C.) |
|---|---|---|---|---|---|---|---|
| 28 | Ph | H | H | H | H | Cl | 206–209 |
| 29 | Ph | H | H | Cl | H | H | 174–176 |
| 30 | Ph | H | H | Cl | Me | H | 176.5–177.5 |
| 31 | Ph | H | H | Br | H | H | 191–194 |

TABLE 7

| No. | R¹ | R² | R³ | M.P. (°C.) |
|---|---|---|---|---|
| 32 | tBu | H | 3-Cl-thiophen-2-yl | 187.0–191.0 |
| 33 | tBu | H | 3-Cl-1-Et-pyrazol-5-yl | 218.2–219.0 |
| 34 | tBu | H | 3-tBu-5-Cl-1-Me-pyrazol-4-yl | 221.5–223.0 |
| 35 | tBu | H | 3-Cl-5-OH-1-Me-pyrazol-4-yl | 266.0–268.0 |
| 36 | tBu | H | 4-Cl-1-Me-pyrazol-5-yl | 203.0–205.0 |
| 37 | tBu | H | 2,4-Me₂-thiazol-5-yl | 188.5–184.5 |
| 38 | tBu | H | pyridin-4-yl | 185.0–187.0 |
| 39 | tBu | H | 4-Et-2-Me-thiazol-5-yl | 192.0–193.0 |
| 40 | tBu | H | 2-Me-4-CF₈-thiazol-5-yl | 223.0–228.4 |
| 41 | tBu | H | 2-Me-pyridin-3-yl | 164.5–170.0 |
| 42 | sBu | H | 3,5-Cl₂-1-Me-pyrazol-4-yl | 134.8–139.2 |
| 43 | sBu | H | 5-Cl-3-CF₈-1-Me-pyrazol-4-yl | 151.0–156.0 |
| 44 | Et | Me | 5-Cl-3-CF₈-1-Me-pyrazol-4-yl | 230.0–233.0 |
| 45 | Et | Me | 3,5-Cl₂-1-Me-pyrazol-4-yl | 211.0–213.0 |
| 46 | 1-Me-Bu | H | 3,5-Cl₂-1-Me-pyrazol-4-yl | 160.0–161.0 |
| 47 | iPr | H | 5-Cl-3-CF₈-1-Me-pyrazol-4-yl | 223.0–224.0 |
| 48 | iPrCH₂ | H | 5-Cl-3-CF₈-1-Me-pyrazol-4-yl | 205.0–206.0 |
| 49 | 1-Me-Bu | H | 5-Cl-3-CF₈-1-Me-pyrazol-4-yl | 166.0–167.0 |
| 50 | iPrCH₂ | H | 3,5-Cl₂-1-Me-pyrazol-4-yl | 223.4–225.6 |
| 51 | nHex | H | 3,5-Cl₂-1-Me-pyrazol-4-yl | 142.5–143.7 |
| 52 | nPen | H | 3,5-Cl₂-1-Me-pyrazol-4-yl | 150.0–157.0 |
| 53 | Et | H | 5-Cl-3-CF₈-1-Me-pyrazol-4-yl | 220.0–227.0 |
| 54 | iPr | H | 3,5-Cl₂-1-Me-pyrazol-4-yl | 186.0–189.0 |
| 55 | nHex | H | 5-Cl-8-CF₈-1-Me-pyrazol-4-yl | 144.5–146.0 |
| 56 | iPrCH₂CH₂ | H | 3,5-Cl₂-1-Me-pyrazol-4-yl | 152.0–153.0 |
| 57 | tBuCH₂ | H | 5-Cl-3-CF₈-1-Me-pyrazol-4-yl | 247.7–248.5 |
| 58 | tBuCH₂ | H | 3,5-Cl₂-1-Me-pyrazol-4-yl | 262.0–264.0 |
| 59 | cPr | R | 5-Cl-3-CF₈-1-Me-pyrazol-4-yl | 236.0–238.0 |
| 60 | cPr | H | 3,5-Cl₂-1-Me-pyrazol-4-yl | 198.6–199.2 |
| 61 | cHex | H | 3,5-Cl₂-1-Me-pyrazol-4-yl | 195.0–196.0 |
| 62 | cHex | H | 5-Cl-3-CF₈-1-Me-pyrazol-4-yl | 206.0–206.5 |
| 63 | 1-Me-cHex | H | 5-Cl-3-CF₈-1-Me-pyrazol-4-yl | 217.5–218.5 |
| 64 | 1-adamantyl | H | 3,5-Cl₂-1-Me-pyrazol-4-yl | 231.3–233.0 |
| 65 | 1-acamantyl | H | 5-Cl-3-CF₈-1-Me-pyrazol-4-yl | 253.5–257.0 |
| 66 | cHex | Me | 3,5-Cl₂-1-Me-pyrazol-4-yl | 173.1–174.6 |
| 67 | cHex | Me | 5-Cl-3-CF₈-1-Me-pyrazol-4-yl | 230.0–232.2 |
| 68 | cHex | H | 2-Me-4-CF₈-thiazol-5-yl | 175.0–178.0 |
| 69 | 1-adamantyl | H | 2-Cl-pyridin-3-yl | 208.0–212.0 |
| 70 | cHex | H | 2-Cl-pyridin-3-yl | 184.0–186.5 |
| 71 | cHex | H | 2-MeS-pyridin-3-yl | 167.0–168.5 |
| 72 | 1-adamantyl | H | 2-MeS-pyridin-3-yl | 227.0–230.0 |
| 73 | cHex | H | 2-MeO-pyridin-3-yl | 175.7–176.7 |
| 74 | 1-adamantyl | H | 2-MeO-pyridin-3-yl | 149.0–156.0 |
| 75 | 1-Me-cHex | H | 3,5-Cl₂-1-pyrazol-4-yl | 186.0–189.0 |
| 76 | CF₈ | H | 3,5-Cl₂-1-Me-pyrazol-4-yl | oil |
| 77 | ClCH₂C(Me)₂ | H | 3,5-Cl₂-1-Me-pyrazol-4-yl | 170.0–172.0 |
| 78 | Cl₂CHC(Me)₂ | H | 3,5-Cl₂-1-Me-pyrazol-4-yl | 210.0–211.0 |
| 79 | CH₂=C(Me) | H | 3,5-Cl₂-1-Me-pyrazol-4-yl | 198.0–199.0 |
| 80 | MeO₂CC(Me)₂ | H | 3,5-Cl₂-1-Me-pyrazol-4-yl | 132.0–134.0 |
| 81 | EtO₂CC(Me)₂ | H | 3,5-Cl₂-1-Me-pyrazol-4-yl | 141.0–143.0 |
| 82 | 4-CF₈-Ph | H | 5-Cl-3-CF₈-1-Me-pyrazol-4-yl | 195.0–198.0 |
| 83 | 4-CF₈-Ph | H | 3,5-Cl₂-1-Me-pyrazol-4-yl | 176.3–177.5 |
| 84 | 4-CF₈-Ph | H | 3-tBu-5-Cl-1-Me-pyrazol-4-yl | 160.0–163.0 |
| 85 | 4-Cl-Ph | H | 3,5-Cl₂-1-Me-pyrazol-4-yl | 261.0–264.0 |
| 86 | 4-Cl-Ph | H | 5-Cl-3-CF₈-1-Me-pyrazol-4-yl | 216.0–220.0 |
| 87 | 3-Cl-Ph | H | 5-Cl-3-CF₈-1-Me-pyrazol-4-yl | 156.0–158.0 |
| 88 | 3-Cl-Ph | H | 3,5-Cl₂-1-Me-pyrazol-4-yl | 206.0–210.0 |
| 89 | 2-Cl-Ph | H | 3,5-Cl₂-1-Me-pyrazol-4-yl | 187.0–189.0 |
| 90 | 2-Cl-Ph | H | 5-Cl-3-CF₈-1-Me-pyrazol-4-yl | 176.0–180.0 |
| 91 | 4-tBu-Ph | H | 5-Cl-3-CF₈-1-Me-pyrazol-4-yl | 286.0–291.0 |
| 92 | 3-MeO-Ph | H | 5-Cl-3-CF₈-1-Me-pyrazol-4-yl | 165.0–166.5 |
| 93 | 2-MeO-Ph | H | 5-Cl-3-CF₈-1-Me-pyrazol-4-yl | 187.0–189.5 |
| 94 | 3-CF₈-Ph | H | 5-Cl-3-CF₈-1-Me-pyrazol-4-yl | 174.0–175.5 |
| 95 | 2-Br-Ph | H | 5-Cl-3-CF₈-1-Me-pyrazol-4-yl | 193.0–195.0 |
| 96 | 2-F-Ph | H | 5-Cl-3-CF₈-1-Me-pyrazol-4-yl | 156.0–160.0 |
| 97 | 3,4-F₂-Ph | H | 3,5-Cl₂-1-Me-pyrazol-4-yl | 239.6–241.1 |
| 98 | 2-MeO-Ph | H | 3,5-Cl₂-1-Me-, pyrazol-4-yl | 208.0–206.0 |
| 99 | 2-Br-Ph | H | 3,5-Cl₂-1-Me-pyrazol-4-yl | 183.0–186.0 |
| 100 | 2,4-Cl₂-Ph | H | 3,5-Cl₂-1-Me-pyrazol-4-yl | 169.5–171.6 |
| 101 | 2,6-F₂-Ph | H | 5-Cl-3-CF₈-1-Me-pyrazol-4-yl | 173.0–176.0 |
| 102 | 2-Me-Ph | H | 5-Cl-3-CF₈-1-Me-pyrazol-4-yl | 165.0–166.5 |
| 103 | Ph | Me | 5-Cl-3-CF₈-1-Me-pyrazol-4-yl | 206.0–212.0 |
| 104 | Ph | Et | 5-Cl-3-CF₈-1-Me-pyrazol-4-yl | 206.5–208.0 |
| 105 | Ph | Me | 3,5-Cl₂-1-Me-pyrazol-4-yl | 185.0–190.0 |
| 106 | Ph | Et | 3,5-Cl₂-1-Me-pyrazol-4-yl | 173.4–174.3 |
| 107 | 2-CF₈-Ph | H | 5-Cl-3-CF₈-1-Me-pyrazol-4-yl | 218.0–221.0 |
| 108 | 2,6-F₂-Ph | H | 3,5-Cl₂-1-Me-pyrazol-4-yl | 171.0–173.0 |
| 109 | 2-CF₈-Ph | H | 3,5-Cl₂-1-Me-pyrazol-4-yl | 213.6–215.0 |
| 110 | 2-EtO-Ph | H | 3,5-Cl₂-1-Me-pyrazol-4-yl | 95.1–98.2 |
| 111 | 2-EtO-Ph | H | 5-Cl-3-CF₈-1-Me-pyrazol-4-yl | 142.0–146.0 |
| 112 | 2-Cl-6-F-Ph | H | 5-Cl-3-CF₈-1-Me-pyrazol-4-yl | 219.0–223.0 |

TABLE 7-continued $$\begin{array}{c}\text{R}^1\diagdown\text{C}=\text{C}\diagup\text{NH}-\text{C}(\text{CN})=\text{C}-\text{S(O)}-\text{R}^3\\\text{R}^2\diagup\qquad\diagdown\text{S}\end{array}$$

| No. | R¹ | R² | R³ | M.P. °C.) |
|---|---|---|---|---|
| 113 | 2,3-Cl$_2$-Ph | H | 3,5-Cl$_2$-1-Me-pyrazol-4-yl | 183.0–184.0 |
| 114 | 2-NO$_2$-Ph | H | 3,5-Cl$_2$-1-Me-pyrazol-4-yl | 222.0–223.0 |
| 115 | 2,3-Cl$_2$-Ph | H | 5-Cl-3-CF$_8$-1-Me-pyrazol-4-yl | 178.0–180.0 |
| 116 | 2,6-(MeO)$_2$Ph | H | 5-Cl-3-CF$_8$-1-Me-pyrazol-4-yl | 148.1–153.0 |
| 117 | 2,6-F$_2$-Ph | H | 2-Me-pyridin-3-yl | 215.6–219.8 |
| 118 | 2,6-F$_2$-Ph | H | 2-Me-4-CF$_8$-thiazol-5-yl | 198.0–203.0 |
| 119 | 2,6-F$_2$-Ph | H | 2,4-Cl$_2$-6-Me-pyridin-3-yl | 171.6–174.1 |
| 120 | 2,6-F$_2$-Ph | H | 2-MeO-pyridin-3-yl | 182.4–183.3 |
| 121 | 2,6-F$_2$-Ph | H | 2-Cl-pyridin-3-yl | 176.8–181.7 |
| 122 | 2,6-F$_2$-Ph | H | 2,4-Me$_2$-oxazol-5-yl | 216.0–219.0 |
| 123 | 2,6-F$_2$-Ph | H | 1-Me-pyrrol-2-yl | 188.0–190.0 |
| 124 | 2,6-F$_2$-Ph | H | 2-MeS-pyridin-3-yl | 150.0–154.0 |
| 125 | 2,6-F$_2$-Ph | H | 2-Et-4-Me-thiazol-5-yl | 164.0–170.0 |
| 126 | 2,6-F$_2$-Ph | H | 3,5-Me$_2$-isoxazol-4-yl | 232.0–235.5 |
| 127 | 2,6-F$_2$-Ph | H | 3-Cl-1-Me-5-MeS-pyrazol-4-yl | 220.0–222.0 |
| 128 | 2,6-F$_2$-Ph | H | 3,5-Me$_2$-pyrazol-1-yl | 219.0–224.0 |
| 129 | 2,6-F$_2$-Ph | H | 3,4-Cl$_2$-1-Me-pyrazol-5-yl | 211.4–213.4 |
| 130 | 2,6-F$_2$-Ph | H | 3,4-Cl$_2$-1-Et-pyrazol-5-yl | 197.8–200.2 |
| 131 | 2,6-F$_2$-Ph | H | 4-Cl-1,5-Me$_2$-pyrazol-3-yl | 168.0–190.0 |
| 132 | 2,6-F$_2$-Ph | H | 1,4-Me$_2$-imidazol-5-yl | 225.0–226.0 |
| 133 | 2,6-F$_2$-Ph | H | 4-MeO$_2$C-pyridin-3-yl | 144.0–146.0 |
| 134 | 2,6-F$_2$-Ph | H | 2-Me-furan-3-yl | 179.0–182.0 |
| 135 | 2,6-F$_2$-Ph | H | pyrazin-2-yl | 239.3–240.4 |
| 136 | 2,6-F$_2$-Ph | H | 5-Me-1-Ph-1,2,3-triazol-4-yl | 197.0–198.0 |
| 137 | 2,6-F$_2$-Ph | H | 1,3-Me$_2$-4-NO$_2$-pyrazol-5-yl | 200.0–201.0 |
| 138 | 2-furyl | H | 3,5-Cl$_2$-1-Me-pyrazol-4-yl | 223.0–225.0 |
| 139 | 5-Cl-1-Me-pyrazol-4-yl | H | 5-Cl-3-CF$_8$-1-Me-pyrazol-4-yl | 238.0–243.0 |
| 140 | 1-naphthyl | H | 3,5-Cl$_2$-1-Me-pyrazol-4-yl | 222.0–224.0 |
| 141 | 1-naphthyl | H | 5-Cl-3-CF$_8$-1-Me-pyrazol-4-yl | 197.0–198.0 |
| 142 | 2-AcO-Ph | H | 3,5-Cl$_2$-1-Me-pyrazol-4-yl | 274.1–276.8 |
| 143 | 2-F-Ph | Me | 5-Cl-3-CF$_8$-1-Me-pyrazol-4-yl | 218.0–221.0 |
| 144 | 2-MeO-Ph | Me | 5-Cl-3-CF$_8$-1-Me-pyrazol-4-yl | 230.0–232.5 |
| 145 | 2-F-Ph | H | 3,5-Cl$_2$-1-Me-pyrazol-4-yl | 188.0–190.5 |
| 146 | Ph | H | 3,5-Me$_2$-pyrazol-1-yl | 205.0–208.0 |
| 147 | 1-naphthyl | H | 2-Cl-pyridin-3-yl | 168.0–170.0 |
| 148 | 1-naphthyl | H | 2-MeS-pyridin-3-yl | 203.0–205.0 |
| 149 | 1-naphthyl | H | 2-MeO-pyridin-3-yl | 275.1–277.6 |
| 150 | 3-pyridyl | H | 2-Cl-pyridin-3-yl | 228.0–229.0 |
| 151 | 4-pyridyl | H | 2-Cl-pyridin-3-yl | 225.0–226.0 |
| 152 | Ph | H | 2,3-Cl$_2$-pyridin-5-yl | 200.0–203.0 |
| 153 | Ph | H | 2,6-Cl$_2$-pyridin-4-yl | 214.0–216.0 |
| 154 | Ph | H | 4-Me-1,2,3-thiadiazol-5-yl | 236.0–239.0 |
| 155 | Ph | H | 2,6-Cl$_2$-pyridin-3-yl | 230.0–234.0 |
| 156 | Ph | H | pyridin-3-yl | 184.0–189.0 |
| 157 | Ph | H | 5-Cl-1-Me-3-iPr-pyrazol-4-yl | 71.0–74.0 |
| 158 | tBu | H | 4-Cl-1-Et-pyrazol-5-yl | 211.4–213.6 |
| 159 | Ph | H | 4-Cl-1-Et-pyrazol-5-yl | 212.0–217.0 |
| 160 | Ph | H | 5-Cl-1-Me-3-Ph-pyrazol-4-yl | 215.0–219.0 |
| 161 | nPen | H | 5-Cl-3-CF$_8$-1-Me-pyrazol-4-yl | 180.0–182.0 |
| 162 | 2,6-F$_2$-Ph | H | 3-CF$_8$-1-Me-pyrazol-4-yl | 177.0–179.0 |
| 163 | 2,6-F$_2$-Ph | H | 5-CF$_8$-1-Me-pyrazol-4-yl | 175.0–177.0 |

The followings are the examples of the preparation of the noxious-organism controlling agent containing the compound of the present invention as the active ingredient, but are not to be construed to limit the invention to the examples. In the following examples, "part(s)" means "part(s) by weight".

[Preparation Example 1]
Wettable powder
Compound of the invention 50 parts Zeeculite PFP 43 parts (clay in kaolins; trade name of Zeeculite Co.)
Sorpol 5050 2 parts (anionic surfactant; trade name of TOHO CHEMICAL INDUSTRY CO., LTD.)
LUNOX 1000C 3 parts
Carplex #80 (solidification protector) 2 parts (white carbon; trade name of Shionogi & Co., LTD.)
Mix and grind the above ingredients homogeneously to give a wettable powder.

[Preparation Example 2]
emulsifiable concentrate
Compound of the invention 3 parts
Methylnaphthalene 76 parts
Isophorone 15 parts
Sorpol 3005X 6 parts (mixture of nonionic surfactant and anionic one; trade name of TOHO CHEMICAL INDUSTRY CO., LTD.)
Mix the above ingredients homogeneously to give an emulsifiable concentrate.

[Preparation Example 3]
Flowable
Compound of the invention 35 parts
Agrisol S-711 8 parts (nonionic surfactant; trade name of Kao Co.)
Lunox 1000C 0.5 part (anionic surfactant; trade name of TOHO CHEMICAL INDUSTRY CO,. LTD.)
1% aqueous Rodopol 20 parts (viscosity-increasing agent; trade name of RHONE-POULENC Co.)
Ethylene glycol (antifreeze) 8 parts
Water 28.5 parts
Mix the above ingredients homogeneously to give a flowable.

[Preparation Example 4]
Water dispersible granule (Dry Flowable)Compound of the invention 75 parts
Isoban No. 1 10 parts (anionic surfactant; trade name of Kurarey Isoprene chemical Co.)
Vanilex N 5 parts (anionic surfactant; trade name of NIPPON PAPER INDUSTRIES)
Carplex #80 2 parts (white carbon; trade name of Shionogi & Co., LTD.)
Mix and grind the above ingredients finely and homogeneously to give a dry flowable.

[Preparation Example 5]
Granule
Compound of the invention 0.1 part
Bentonite 55.0 parts
Talc 44.9 parts
Mix and grind the above ingredients homogeneously, stir, mix and knead with a small amount of water, granulate by an extrusion type granulation apparatus and dry to give a granule.

[Preparation Example 6]
Dustable powder
Compound of the invention 3.0 parts
Carplex #80 0.5 part (white carbon; trade name of Shionogi Seiyaku Co.)
Clay 95 parts
Diisopropyl phosphate 1.5 parts
Mix and grind the above ingredients homogeneously to give a dustable powder.

Before application, the wettable powder, emulsifiable concentrate, flowable and water dispersible granule described above are diluted from 50 to 20,000 times with water to apply at from 0.005 to 50 kg of active ingredient per hectare.

TEST EXAMPLE

The detailed descriptions with respect to usefulness of the compounds of the present invention as pest control agents are provided in the following test examples.

Test Example 1: Insecticidal Test on the 28-spotted ladybird, *Epilachna vigintioctopunctata*

An 5% emulsifiable concentrate (or a 25% wettable powder; it depends on physicochemical properties of compounds) of a compound of the present invention described in the specification was diluted with water containing a spreader to prepare the test solution in a concentration of 500 ppm, and a leaf-cut of tomato was soaked in the test solution for approximately 10 seconds, dried by air and placed in a petri dish, and ten 2nd-instar larvae *Epilachna vigintioctopunctata* per dish were released in the petri dish, and it was capped and maintained in a incubator at 25° C. for 6 days, and then, mortality was observed. Insecticidal activity was calculated by the following formula. All treatment and untreatment control were replicated two times.

Insecticidal activity (%)=(Number of dead insect/Number of released insect)×100

As a result, the compounds described below afforded the insecticidal activity of 80% or more.

The compound of the present invention No. 6, 19, 20, 21, 29, 30, 31, 49, 82, 93, 96, 101, 102, 108, 112, 113, 141

Test Example 2: Insecticidal Test on the cucumber leaf beetle, *Aulacophora femoralis*

An 5% emulsifiable concentrate (or a 25% wettable powder; it depends on physicochemical properties of compounds) of a compound of the present invention described in the specification was diluted with water containing a spreader to prepare the test solution in a concentration of 500 ppm, and a leaf-cut of cucumber was soaked in the test solution for approximately 10 seconds, dried by air and placed in a petri dish, and ten 2nd-instar larvae of *Aulaacophora femoralis* per dish were released in the petri dish, and it was capped and maintained in a incubator at 25° C. for 6 days, and then, mortality was observed. Insecticidal activity was calculated by the formula in the test example 1. All treatments and untreatment control were replicated two times. As a result, the compounds described below afforded the insecticidal activity of 80% or more. The compound of the present invention No. 1, 3, 5, 6, 9, 11, 12, 15, 16, 17, 19, 21, 24, 25, 27, 28, 29, 30, 31, 32, 33, 37, 39, 40, 41, 42, 43, 46, 47, 48, 49, 50, 51, 52, 54, 55, 56, 57, 59, 60, 61, 62, 63, 64, 65, 66, 67, 68, 69, 70, 71, 72, 73, 74, 75, 77, 78, 80, 86, 87, 89, 90, 92, 93, 95, 96, 98, 99, 101, 102, 103, 104, 105, 106, 107, 108, 109, 110, 111, 112, 113, 114, 115, 116, 117, 118, 120, 121, 122, 123, 124, 125, 126, 127, 128, 129, 132, 138, 139, 140, 141, 143, 144, 145, 146, 147, 148, 149, 150, 161, 162

Test Example 3: Insecticidal Examination on the brown planthopper, *Nilaparvata lugens*

An 5% emulsifiable concentrate (or a 25% wettable powder; it depends on physicochemical properties of compounds) of the compound of the present invention described in the specification was diluted with water containing a spreader to prepare the test solution in a concentration of 500 ppm.

The test solution was sprayed on a potted rice plant in a pot of 1/20,000 are to run-off. After drying by air, a circular cylinder was situated, and ten 2nd-instar nymphae of *Nilaparvata lugens* per pot were released, and then, the cylinder was capped and maintained in a incubator. After 6 days, mortality was observed and insecticidal activity was calculated by the formula in the test example 1. All treatment and untreatment control were replicated two times. As a result, the compounds described below afforded the insecticidal activity of 80% or more.

The compound of the present invention No. 3, 6, 15, 31, 43, 68, 89, 93, 95, 96, 101, 102, 107, 108, 109, 111 112, 117, 118, 120, 121, 124, 128, 140, 146, 162

Test Example 4: Insecticidal Examination on the green rice leafhopper, *Nephotettix cincticeps*

A stem of rice were soaked in an aqueous solution in a concentration of 500 ppm of a compound of the present invention for approximately 10 seconds, and the stem was placed in a glass tube adults of *Nephotettix cincticeps* that were resistant to organophosphorus insecticides were released, and the tube was covered with a cap and maintained in a incubator at 25° C. for 6 days, and then, mortality was observed. Insecticidal activity was calculated by the formula in the test example 1. All treatments and untreatment control were replicated two times. As a result, the compounds described below afforded the insecticidal activity of 80% or more.

The compound of the present invention No. 1, 3, 6, 9, 15, 19, 25, 27, 29, 31, 32, 37, 41, 42, 47, 54, 60, 61, 68, 77, 89, 90, 93, 94, 95, 96, 98, 99, 101, 102, 103, 107, 108, 109, 110, 111, 112, 113, 114, 115, 117, 118, 120, 121, 122, 124, 126, 128, 130, 132, 140, 141, 145, 146, 147, 159, 162

Test Example 5: Insecticidal Examination on *Myzus persicae*

A wet filter paper was placed in a glass petri dish of 3 cm inside diameter, and a leaf of cabbage of the same diameter was put on it. Four apterous female adults of *Myzus persicae* were released, and a test solution (2.5 mg/cm$^2$) was sprayed by a rotary spray tower after a day. As the test solution used, an 5% emulsified concentrate (or a 25% wettable powder; it depends on physicochemical properties of compounds) of a compound of the present invention was diluted with water containing a spreader to adjust the concentration to 500 ppm. Six days after the treatment, the insecticidal activity to the adult and nymph was calculated by the following formula. All treatments and untreatment control were replicated two times.

Insecticidal activity (%)=(Number of dead insect/ (Number of dead insect+Number of survival insect))×100

As a result, the compounds described below afforded the insecticidal activity of 80% or more.

The compound of the present invention No. 3, 6, 9, 15, 16, 19, 21, 25, 27, 40, 41, 42, 43, 46, 48, 49, 52, 54, 59, 60, 62, 63, 66, 73, 75, 77, 78, 79, 80, 87, 89, 90, 93, 95, 96, 98, 99, 101, 102, 103, 104, 106, 107, 108, 109, 110, 111, 112, 117, 118, 119, 120, 121, 122, 124, 126, 128, 129, 131, 133, 141, 143, 145, 146, 159, 161, 162, 163

Test Example 6: Contacting Insecticidal Test on the diamond-back moth *Plutella xylostella*

A leaf-cut of cabbage was soaked in an aqueous solution in a concentration of 500 ppm of a compound of the present invention for approximately 10 seconds, dried by air and placed in a petri dish, and ten 2nd-instar of *Plutella xylostella* per dish were released in the petri dish, and it was covered with a cap with vents and maintained in a thermostat at 25° C. for 6 days, and the number of the dead insect was counted, and then, the insecticidal activity was calculated by the formula in the test example 1. All treatments and untreatment control were replicated two times. As a result, the compounds described below afforded the insecticidal rate of 80% or more.

The compound of the present invention No. 3, 6, 9, 11, 15, 16, 17, 19, 21, 23, 24, 25, 26, 27, 29, 30, 31, 32, 33, 34, 36, 37, 38, 39, 40, 41, 42, 43, 46, 47, 48, 49, 50, 54, 56, 57, 58, 59, 60, 61, 62, 63, 64, 65, 66, 67, 68, 69, 70, 71, 72, 73, 74, 75, 77, 78, 79, 84, 88, 89, 93, 95, 96, 98, 99, 101, 102, 103, 104, 105, 106, 107, 108, 109, 110, 111, 112, 113, 114, 115, 117, 118, 120, 121, 122, 123, 124, 125, 126, 128, 129, 130, 132, 134, 135, 138, 140, 141, 143, 144, 145, 146, 147, 148, 149, 150, 158, 162, 163

Test Example 7: Acaricidal Test on *Tetranychus urticae*

A leaf of kidney bean was cut out by a leaf punch in a round of 3.0 cm diameter, and it was put on a wet filter paper placed on a styrol cup of 7 cm diameter. On it, 10 larvae of *Tetranychus urticae* per leaf were inoculated. An 5% emulsifiable concentrate (or a 25% wettable powder, it depends on physicochemical properties of compounds) of the compound of the present invention described in the specification was diluted with water containing a spreader to prepare the test solution in a concentration of 500 ppm, and 2 ml of the test solution per cup was sprayed by a rotary spray tower, and the cup was maintained in a incubator at 25° C. for 96 hours, and then, mortality was observed. Insecticidal activity was calculated by the formula in the test example 1. All treatments and untreatment control were replicated two times. As a result, the compounds described below afforded the insecticidal rate of 80% or more.

The compound of the present invention No. 6, 9, 11, 24, 25, 26, 27, 37, 39, 40, 42, 43, 46, 47, 48, 49, 50, 52, 53, 54, 55, 56, 58, 59, 60, 61, 62, 63, 64, 66, 67, 68, 69, 73, 74, 75, 77, 78, 80, 81, 92, 93, 95, 96, 98, 99, 100, 101, 102, 103, 104, 105, 106, 107, 108, 109, 110, 111, 112, 113, 115, 120, 124, 125, 128, 139, 143, 144, 145, 161, 162

INDUSTRIAL APPLICABILITY

The compounds of the present invention have excellent insecticidal and acaricidal activity against a number of agricultural pest, and hardly exert any adverse effects upon mammals, fishes and beneficial insects.

Therefore, the compounds of the present invention provide useful pest control agents.

What is claimed is:
1. An oxopropionitrile derivative of the formula (1):

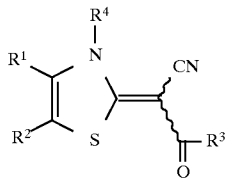

wherein
$R^1$ represents a hydrogen or halogen atom, an alkyl group of 2 to 8 carbon atoms, a haloalkyl group of 1 to 6 carbon atoms, an alkenyl group of 2 to 4 carbon atoms, a cycloalkyl group of 3 to 10 carbon atoms optionally substituted with an alkyl group of 1 to 3 carbon atoms, an alkyl group of 1 to 4 carbon atoms substituted with an alkoxycarbony group of which the alkoxyl moiety comprises from 1 to 4 carbon atoms, a pyridyl, naphthyl or thienyl group, or a phenyl group optionally substituted with X;

$R^2$ represents a hydrogen atom, halogen atom, an alkyl group of 1 to 8 carbon atoms, a haloalkyl group of 1 to 6 carbon atoms, a cycloalkyl group of 3 to 10 carbon atoms optionally substituted with an alkyl group of 1 to 3 carbon atoms, or a phenyl group optionally substituted with X;

X represents one or more substituent groups optionally selected from a halogen atom, an alkyl group of 1 to 4 carbon atoms, an alkoxyl group of 1 to 4 carbon atoms, an alkylsulfenyl group of 1 to 4 carbon atoms, an alkylsulfinyl group of 1 to 4 carbon atoms, an alkylsulfonyl group of 1 to 4 carbon atoms, a haloalkyl group of 1 to 4 carbon atoms, a $NO_2$, CN group, an alkylcarbonyloxy group of which the alkyl moiety comprises from 1 to 4 carbon atoms, or a dialkylamino group of which the alkyl moieties independently comprise from 1 to 4 carbon atoms, where X may be same or different when the number of X is two or more;

$R^3$ represents a heterocyclic group containing from 1 to 4 heteroatoms as the cyclic members optionally selected from a oxygen, sulfur or nitrogen atom besides the carbon atoms, which is optionally substituted with Y is selected from a furan-2-yl, furan-3-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, imidazol-1-yl, imidazol-2-yl, imidazol-4-yl, imidazol-5-yl, isoxazol-3-yl, isoxazol-4-yl, isoxazol-5-yl, isothiazol-3-yl, isothiazol-4-yl, isothiazol-5-yl, pyrazol-1-yl, pyrazol-3-yl, pyrazol-4-yl, pyrazol-5-yl, 1,3,4-oxadiazol-2-yl, 1,3,4-thiadiazol-2-yl, 1,3,4-triazol-1-yl, 1,3,4-triazol-2-yl, 1,2,4-oxadiazol-3-yl, 1,2,4-oxadiazol-5-yl, 1,2,4-thiadiazol-3-yl, 1,2,4-thiadiazol-5-yl, 1,2,4-triazol-1-yl, 1,2,4-triazol-3-yl, 1,2,4-triazol-5-yl, 1,2,3-oxadiazol-4-yl, 1,2,3-oxadiazol-5-yl, 1,2,3-thiadiazol-4-yl, 1,2,3-thiadiazol-5-yl, 1,2,3-triazol-1-yl, 1,2,3-triazol-4-yl, 1,2,3-triazol-5-yl, 1,2,3,4-tetrazol-1-yl, 1,2,3,4-tetrazol-5-yl, 1,2,3,5-tetrazol-1-yl, 1,2,3,5-tetrazol-4-yl, pyridin-2-yl, pyridin-3-yl, pyridin-4-yl, pyrazin-2-yl, pyridazin-3-yl, pyridazin-4-yl, 1,3,5-triazin-2-yl, 1,2,4-triazin-3-yl, 1,2,4-triazin-5-yl, 1,2,4-triazin-6-yl, pyrazolin-1-yl, pyrazolin-3-yl, pyrazolin-4-yl, pyrazolin-5-yl, imidazolin-1-yl, imidazolin-2-yl, imidazolin-4-yl, imidazolin-5-yl, oxazolin-2-yl, oxazolin-4-yl, oxazolin-5-yl, isoxazolin-3-yl, isoxazolin-4-yl, isoxazolin-5-yl, thiazolin-2-yl, thiazolin-4-yl, thiazolin-5-yl, 3(2H)-pyridazinon-2-yl, 3(2H)-pyridazinon-4-yl, 3(2H)-pyridazinon-5-yl or 3(2H)-pyridazinon-6-yl group, a thiophen-2-yl group substituted with Z, or a thiophen-3-yl group substituted with Z;

Y represents one or more substituent groups optionally selected from a halogen atom, an alkyl group of 1 to 4 carbon atoms, an alkoxyl group of 1 to 4 carbon atoms, a haloalkyl group of 1 to 4 carbon atoms, an alkylsulfenyl group of 1 to 4 carbon atoms, an alkylsulfinyl group of 1 to 4 carbon atoms, an alkylsulfonyl group of 1 to 4 carbon atoms, a phenyl, benzyl, phenoxy, $NO_2$, CN, OH, an alkoxyalkyl group of 2 to 4 carbon atoms, an alkylcarbonyl group of 2 to 4 carbon atoms, an alkoxycarbonyl group of which the alkoxyl moiety comprises from 1 to 4 carbon atoms, or a dialkylamino group of which the alkyl moieties independently comprise from 1 to 4 carbon atoms, where Y may be same or different when the number of Y is two or more;

Z represents one or more substituent groups optionally selected from a halogen atom, an alkyl group of 1 to 4 carbon atoms, an alkoxyl group of 1 to 4 carbon atoms, a haloalkyl group of 1 to 4 carbon atoms, an alkylsulfenyl group of 1 to 4 carbon atoms, an alkylsulfinyl group of 1 to 4 carbon atoms, an alkylsulfonyl group of 1 to 4 carbon atoms, a phenyl, benzyl, phenoxy, $NO_2$, CN, an alkoxycarbonyl group of which the alkoxyl moiety comprises from 1 to 4 carbon atoms, or a dialkylamino group of which the alkyl moieties independently comprise from 1 to 4 carbon atoms, where Z may be same or different when the number of Z is two or more; and $R^4$ represents a hydrogen atom, an alkyl group of 1 to 4 carbon atoms, a haloalkyl group of 1 to 4 carbon atoms, an alkoxyalkyl group of 2 to 4 carbon atoms, an alkylcarbonyl of 2 to 4 carbon atoms, an alkoxycarbonyl of which the alkoxyl moiety comprises from 1 to 4 carbon atoms, or a phenyl or benzyl group.

2. The oxopropionitrile derivative of the formula (1) as claimed in claim 1, wherein $R^2$ represents a hydrogen atom or an alkyl group of 1 to 8 carbon atoms;

$R^3$ represents a furan-3-yl group optionally substituted with Y, a pyrrol-2-yl group optionally substituted with Y, a pyrazol-1-yl group optionally substituted with Y, a pyrazol-3-yl group optionally substituted with Y, a pyrazol-4-yl group optionally substituted with Y, a pyrazol-5-yl group optionally substituted with Y, an imidazol-5-yl group optionally substituted with Y, a thiazol-5-yl group optionally substituted with Y, an oxazol-5-yl group optionally substituted with Y, an isoxazol-4-yl group optionally substituted with Y, a 1,2,3-triazol-5-yl group optionally substituted with Y, a 1,2,3-thiadiazol-5-yl group optionally substituted with Y, a pyridin-3-yl group optionally substituted with Y, a pyridin-4-yl group optionally substituted with Y, a pyrazin-2-yl group optionally substituted with Y, a thiophen-2-yl group substituted with Z, or a thiophen-3-yl group substituted with Z;

Y represents one, two or three substituent groups optionally selected from a halogen atom, an alkyl group of 1 to 4 carbon atoms, an alkoxyl group of 1 to 4 carbon atoms, a haloalkyl group of 1 to 4 carbon atoms, an alkylsulfenyl group of 1 to 4 carbon atoms, an alkylsulfinyl group of 1 to 4 carbon atoms, an alkylsulfonyl group of 1 to 4 carbon atoms, a phenyl, benzyl, phenoxy, $NO_2$, CN, OH, an alkoxycarbonyl group of which the alkoxyl moiety comprises from 1 to 4 carbon atoms, or a dialkylamino group of which the alkyl moieties independently comprise from 1 to 4 carbon atoms, where Y may be same or different when the number of Y is two or more;

Z represents one or two substituent groups optionally selected from a halogen atom, or an alkyl group of 1 to 4 carbon atoms, where Z may be same or different when the number of Z is two; and $R^4$ represents a hydrogen atom, or an alkyl group of 1 to 4 carbon atoms.

3. The oxopropionitrile derivative of the formula (1) as claimed in claim 2, wherein $R^1$ represents a phenyl group optionally substituted with X; and $R^4$ represents a hydrogen atom.

4. The oxopropionitrile derivative of the formula (1) as claimed in claim 2, wherein $R^3$ represents a pyrazol-1-yl group optionally substituted with Y, a pyrazol-3-yl group optionally substituted with Y, a pyrazol-4-yl group optionally substituted with Y, or a pyrazol-5-yl group optionally substituted with Y.

5. The oxopropionitrile derivative of the formula (1) as claimed in claim 3, wherein $R^3$ represents a pyridin-3-yl group optionally substituted with Y, or a pyridin-4-yl group optionally substituted with Y.

6. The oxopropionitrile derivative of the formula (1) as claimed in claim 3, wherein $R^3$ represents a thiazol-5-yl group optionally substituted with Y.

7. The oxopropionitrile derivative of the formula (1) as claimed in claim 3, wherein $R^3$ represents an imidazol-5-yl group optionally substituted with Y.

8. The oxopropionitrile derivative of the formula (1) as claimed in claim 1, wherein $R^1$ and $R^2$ each independently represents a hydrogen or halogen atom, an alkyl group of 2 to 6 carbon atoms, a haloalkyl group of 1 to 6 carbon atoms, a cycloalkyl group of 3 to 6 carbon atoms optionally substituted with an alkyl group of 1 to 3 carbon atoms, or

where X represents a halogen atom, a $C_{1-4}$ alkyl group, a $C_{1-4}$ alkoxyl group, a $C_{1-4}$ alkylsulfenyl group, a $C_{1-4}$ haloalkylgroup, a $NO_2$, CN, or $(C_{1-4}$ alkyl$)_2$N of which the alkyl moieties are same or different; m is an integer from 0 to 5; and X may be same or different when m is an integer from 2 to 5;

$R^3$ represents

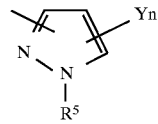

where Y represents a halogen atom, a $C_{1-4}$ alkyl group, a $C_{1-4}$ alkoxyl group, a $C_{1-4}$ haloalkyl group, a $C_{1-4}$ alkylsulfenyl group, a $C_{1-4}$ alkylsulfinyl group, a $C_{1-4}$ alkylsulfonyl group, a phenyl, benzyl, phenoxy, $NO_2$, CN, a $C_{2-4}$ alkoxycarbonyl group, or a $(C_{1-4}$ alkyl$)_2$N of which the alkyl moieties are same or different; n is an integer from 0 to 2; Y may be same or different when n is 2; and $R^5$ represents a hydrogen atom, a $C_{1-4}$ alkyl group, a $C_{1-4}$ haloalkyl group, a $C_{2-4}$ alkoxyalkyl group, a $C_{2-4}$ alkylcarbonyl group, or a phenyl or benzyl group; or

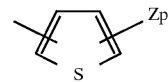

where Z represents a halogen atom, a $C_{1-4}$ alkyl group, a $C_{1-4}$ alkoxyl group, a $C_{1-4}$ haloalkyl group, a $C_{1-4}$ alkylsulfenylgroup, a $C_{1-4}$ alkylsulfinyl group, a $C_{1-4}$ alkylsulfonyl group, a phenyl, benzyl, phenoxy, $NO_2$, CN, a $C_{2-4}$ alkoxycarbonyl group, or a $(C_{1-4}$ alkyl$)_2$N of which the alkyl moieties are same or different; p is an integer from 1 to 2; and Z may be same or different when p is 2; and $R^4$ represents a hydrogen atom, a $C_{1-4}$ alkyl group, a $C_{1-4}$ haloalkyl group, a $C_{2-4}$ alkoxyalkyl group, a $C_{2-4}$ alkylcarbonyl group, a phenyl, or benzyl group.

9. The oxopropionitrile derivative of the formula (1) as claimed in claim 8, wherein $R^3$ represents:

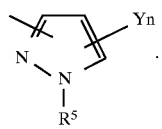

10. The oxopropionitrile derivative of the formula (1) as claimed in claim 8, wherein $R^3$ represents:

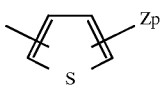

11. The oxopropionitrile derivative of the formula (1) as claimed in claim 8, wherein $R^2$ represents a hydrogen atom.

12. The oxopropionitrile derivative of the formula (1) as claimed in claim 11, wherein $R^3$ represents:

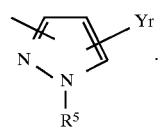

13. The oxopropionitrile derivative of the formula (1) as claimed in claim 11, wherein $R^3$ represents:

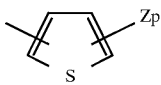

14. The oxopropionitrile derivative as claimed in claim 1, selected from the compound group described below consisting of
(1) 2-(4-tert-butyl-2,3-dihydrothiazol-2-ylidene)-3-(5-chloro-1-methyl-3-trifluoromethylpyrazol-4-yl)-3-oxopropionitrile,
(2) 2-(4-tert-butyl-2,3-dihydrothiazol-2-ylidene)-3-(3,5-dichloro-1-methylpyrazol-4-yl)-3-oxopropionitrile,
(3) 2-{4-(2,6-difluorophenyl)-2,3-dihydrothiazol-2-ylidene}-3-(5-chloro-1-methyl-3-trifluoromethylpyrazol-4-yl)-3-oxopropionitrile,
(4) 2-{4-(2,6-difluorophenyl)-2,3-dihydrothiazol-2-ylidene}-3-(3,5-dichloro-1-methylpyrazol-4-yl)-3-oxopropionitrile,
(5) 2-{4-(2-chloro-6-fluorophenyl)-2,3-dihydrothiazol-2-ylidene}-3-(5-chloro-1-methyl-3-trifluoromethylpyrazol-4-yl)-3-oxopropionitrile,
(6) 2-{4-(1-naphthyl)-2,3-dihydrothiazol-2-ylidene}-3-(5-chloro-1-methyl-3-trifluoromethylpyrazol-4-yl)-3-oxopropionitrile,
(7) 2-{4-(1-naphthyl)-2,3-dihydrothiazol-2-ylidene}-3-(3,5-dichloro-1-methylpyrazol-4-yl)-3-oxopropionitrile,
(8) 2-{4-(2,6-difluorophenyl)-2,3-dihydrothiazol-2-ylidene}-3-(2-chloropyridin-3-yl)-3-oxopropionitrile,
(9) 2-{4-(2,6-difluorophenyl)-2,3-dihydrothiazol-2-ylidene}-3-(2-methoxypyridin-3yl)-3-oxopropionitrile,
(10) 2-{4-(2,6-difluorophenyl)-2,3-dihydrothiazol-2-ylidene}-3-(2-methylthiopyridin-3-yl)-3-oxopropionitrile, and
(11) 2-{4-(2,6-difluorophenyl)-2,3-dihydrothiazol-2-ylidene}-3-(3,5-dimethylpyrazol-1-yl)-3-oxopropionitrile.

15. A pest controlling agent characterized by containing at least one kind of the derivative as claimed in any one of claims 1 to 14.

* * * * *